United States Patent
Mitra et al.

(10) Patent No.: US 10,441,630 B2
(45) Date of Patent: *Oct. 15, 2019

(54) TOPICAL FORMULATIONS AND USES THEREOF

(71) Applicant: OCULAR TECHNOLOGIES SARL, Epalinges (CH)

(72) Inventors: Ashim K. Mitra, Overland Park, KS (US); Sidney L. Weiss, Randolph, NJ (US); Eugene J. McNally, Fitchburg, WI (US)

(73) Assignee: SUN PHARMA GLOBAL FZE, Sharjah (AE)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,640

(22) Filed: May 12, 2016

(65) Prior Publication Data

US 2016/0256521 A1 Sep. 8, 2016

Related U.S. Application Data

(63) Continuation of application No. 14/629,883, filed on Feb. 24, 2015, now abandoned, which is a continuation of application No. PCT/US2013/056513, filed on Aug. 23, 2013.

(60) Provisional application No. 61/693,189, filed on Aug. 24, 2012.

(51) Int. Cl.
| | | |
|---|---|---|
| *A61K 38/13* | (2006.01) | |
| *A61K 47/44* | (2017.01) | |
| *A61K 9/00* | (2006.01) | |
| *A61K 47/10* | (2017.01) | |
| *A61K 9/107* | (2006.01) | |
| *A61K 31/202* | (2006.01) | |

(52) U.S. Cl.
CPC ............ *A61K 38/13* (2013.01); *A61K 9/0048* (2013.01); *A61K 9/1075* (2013.01); *A61K 31/202* (2013.01); *A61K 47/10* (2013.01); *A61K 47/44* (2013.01)

(58) Field of Classification Search
CPC .... A61K 38/13; A61K 9/0048; A61K 9/1075; A61K 31/202; A61K 47/10; A61K 47/44
See application file for complete search history.

(56) References Cited

U.S. PATENT DOCUMENTS

| | | |
|---|---|---|
| 5,484,597 A | 1/1996 | Slavtcheff et al. |
| 5,843,891 A | 12/1998 | Sherman |
| 5,951,971 A | 9/1999 | Kawashima et al. |
| 5,998,365 A | 12/1999 | Sherman |
| 6,071,958 A | 6/2000 | Jimenez-Bayardo |
| 7,060,672 B2 | 6/2006 | Naicker et al. |
| 7,087,237 B2 | 8/2006 | Peyman |
| 7,833,966 B2 | 11/2010 | Peyman |
| 8,435,544 B2 | 5/2013 | Mitra et al. |
| 8,535,694 B2 | 9/2013 | Mitra et al. |
| 8,980,839 B2 | 3/2015 | Mitra et al. |
| 9,017,725 B2 | 4/2015 | Mitra et al. |
| 9,770,447 B2 | 9/2017 | Ostrow et al. |
| 9,937,225 B2 | 4/2018 | Mitra et al. |
| 2002/0045601 A1 | 4/2002 | Kawashima et al. |
| 2003/0176356 A1 | 9/2003 | Yorio et al. |
| 2005/0042198 A1 | 2/2005 | Smith et al. |
| 2006/0205639 A1 | 9/2006 | Domb et al. |
| 2006/0217309 A1 | 9/2006 | Naicker et al. |
| 2007/0015691 A1 | 1/2007 | Chang et al. |
| 2007/0248645 A1 | 10/2007 | Bague et al. |
| 2007/0249632 A1 | 10/2007 | Zentner et al. |
| 2008/0299206 A1 | 12/2008 | Lee et al. |
| 2009/0092665 A1 | 4/2009 | Mitra et al. |
| 2009/0209599 A1 | 8/2009 | Endo et al. |
| 2009/0234004 A1 | 9/2009 | Kabra et al. |
| 2009/0286718 A1 | 11/2009 | Stringer |
| 2009/0298956 A1 | 12/2009 | Chowhan et al. |
| 2010/0310462 A1 | 12/2010 | Sberg et al. |
| 2010/0310642 A1 | 12/2010 | Mitra et al. |
| 2011/0021443 A1 | 1/2011 | Lambert et al. |
| 2011/0040113 A1 | 2/2011 | Wu et al. |
| 2011/0152264 A1 | 6/2011 | Reunamaki et al. |
| 2011/0300195 A1 | 12/2011 | Mitra et al. |
| 2011/0311592 A1 | 12/2011 | Birbara et al. |
| 2013/0045927 A1 | 2/2013 | Dana et al. |

(Continued)

FOREIGN PATENT DOCUMENTS

| | | |
|---|---|---|
| EP | 2036538 A1 | 3/2009 |
| EP | 2193795 A1 | 6/2010 |

(Continued)

OTHER PUBLICATIONS

Definition of "lipids" from the IUPAC Compendium of Chemical Terminology (Gold Book) downloaded on Jun. 2, 2017 from http://goldbook.iupac.org/src_PAC1995671307.html.*
"Vitamin E" from Medline Plus downloaded on Jun. 2, 2017 from https://medlineplus.gov/ency/article/002406.htm.*
PCT/US2016/029602, "International Search Report and Written Opinion", dated Jul. 15, 2016, 11 pages.
"Cremophor RH 40", Technical Information, BASF, Oct. 2010.
U.S. Appl. No. 13/975,175, "Final Office Action", dated Apr. 1, 2014, 18 Pages.
U.S. Appl. No. 13/975,175, "Non-Final Office Action", dated Dec. 19, 2013, 10 pages.

(Continued)

*Primary Examiner* — Christina Bradley
(74) *Attorney, Agent, or Firm* — Medler Ferro Woodhouse & Mills PLLC

(57) ABSTRACT

Provided herein include formulations for topical administration, such as ophthalmic formulations, and methods of using such formulations. In some aspects and embodiments the formulations may include a polyoxyl lipid or fatty acid, and or a polyalkoxylated alcohol and may include nanomicelles. Also include methods of treating or preventing diseases or conditions, such as ocular diseases or conditions.

7 Claims, No Drawings

(56) References Cited

U.S. PATENT DOCUMENTS

| | | |
|---|---|---|
| 2013/0065888 A1 | 3/2013 | Cetina-Cizmek et al. |
| 2013/0267591 A1 | 10/2013 | Khopade et al. |
| 2014/0057854 A1 | 2/2014 | Mitra et al. |
| 2015/0125494 A1 | 5/2015 | Wang et al. |
| 2015/0148299 A1 | 5/2015 | Mitra et al. |
| 2015/0165048 A1 | 6/2015 | Mitra et al. |
| 2015/0366953 A1 | 12/2015 | Danias et al. |
| 2016/0256520 A1 | 9/2016 | Mitra et al. |
| 2017/0065611 A1 | 3/2017 | Weiss |
| 2018/0133217 A1 | 5/2018 | Weiss |

FOREIGN PATENT DOCUMENTS

| | | |
|---|---|---|
| EP | 2478906 | 7/2012 |
| JP | 2004-238346 | 8/2004 |
| WO | WO2004/069181 A2 | 8/2004 |
| WO | 2004096261 | 11/2004 |
| WO | 2009048929 | 4/2009 |
| WO | WO2013/167865 A1 | 11/2013 |
| WO | 2014032026 | 2/2014 |
| WO | WO2015/179527 A1 | 11/2015 |
| WO | WO2016/178881 A1 | 11/2016 |
| WO | WO2017/083167 A1 | 5/2017 |
| WO | WO2017/083410 A1 | 5/2017 |
| WO | WO2017/151657 A1 | 9/2017 |
| WO | WO2017/152129 A2 | 9/2017 |

OTHER PUBLICATIONS

U.S. Appl. No. 13/975,175, "Non-Final Office Action", dated Jul. 22, 2014, 17 pages.
U.S. Appl. No. 13/975,175, "Notice of Allowance", dated Jan. 2, 2015, 7 pages.
U.S. Appl. No. 14/611,993, "Non-Final Office Action", dated Nov. 10, 2015, 15 pages.
U.S. Appl. No. 14/611,993, "Non-Final Office Action", dated Nov. 18, 2015, 16 pages.
U.S. Appl. No. 14/629,883, "Non-Final Office Action", dated Nov. 13, 2015, 22 pages.
Donnenfeld et al., "Topical Ophthalmic Cyclosporine: Pharmacology and Clinical Uses", Survey of Ophthalmology, vol. 54, No. 3, 2009, pp. 321-338.
EP13831463.8 , "Extended European Search Report", dated Feb. 26, 2016, 8 pages.
NA et al., "Resolvin E1 Improves Tear Production and Decreases Inflammation in a Dry Eye Mouse Model", Journal of Ocular Pharmacology and Therapeutics, vol. 26, No. 5, Oct. 2010, pp. 431-439.
Schmidts et al., "Influence of hydrophilic surfactants on the properties of multiple W/O/W emulsions", Journal of Colloid and Interface Science, vol. 338, No. 1, 2009, pp. 184-192.
International Search Report dated Nov. 18, 2013, in International Application No. PCT/US2013/056513.
J.D. Quintana-Hau et al., "Characterization of the Novel Ophthalmic Drug Carrier Sophisen in Two of Its Derivatives: 3A Ofteno™ and Modusik-A Ofteno™," Drug Development and Industrial Pharmacy, 2005, vol. 31, pp. 263-269.
Restasis Prescribing Information, Allergan, Inc., downloaded Mar. 23, 2014.
Acheampong et al., "Distribution of cyclosporin A in ocular tissues after topical administration to albino rabbits and beagle dogs", Current Eye Research, 18(2):91-103 (1999).
Berge et al., "Pharmaceutical Salts," Journal of Pharmaceutical Science 66(1):1-19 (1977).
Cholkar et al., "Topical, Aqueous, Clear Cyclosporine Formulation Design for Anterior and Posterior Ocular Delivery," Translational Vision Science & Technology 4(3):1 (2015).
"DuoTrav 40," Product Summary Annexes I, II, & III, first published Feb. 12, 2009 on European Medicines Agency. https://www.ema.europa.eu/documents/product-information/duotrav-epar-product-information_en.pdf.
Guo et al., "Nanomicelle formulation for topical delivery of cyclosporine A into the cornea: in vitro mechanism and in vivo permeation evaluation," Scientific Reports 5:12968 (2015).
Hackett et al., "Ophthalmic Toxicology and Assessing Ocular Irritation," Dermatoxicology, 5th Edition. Ed. F. N. Marzulli and H. I. Maibach. Washington, D.C.: Hemisphere Publishing Corporation. 1996; 299-305 and 557-566.
Howell et al., "Combinatorial targeting of early pathways profoundly inhibits neurodegeneration in a mouse model of glaucoma," Neurobiology of Disease 71:44-52 (2014).
Hoyng et al., "Iloprost, a stable prostacyclin analog, reduces intraocular pressure," Investigative Ophthalmology & Visual Science 28(3):470-476 (1987).
Perez-Santonja et al., "Inhibition of Corneal Neovascularization by Topical Bevacizumab (Anti-VEGF) and Sunitinib (Anti-VEGF and Anti-PDGF) in an Animal Model," American Journal of Ophthalmology 150:519-528 (2010).
Resch et al., "Effect of Dual Endothelin Receptor Blockade on Ocular Blood Flow in Patients with Glaucoma and Healthy Subjects," Invest Ophthalmol Vis Sci 50(1):358-363 (2009).
"Travatan," Drug Label Information, updated Jul. 20, 2011 on Daily Med, U.S. National Library of Medicine. https://dailymed.nlm.nih.gov/dailymed/drugInfo.cfm?setid=db08d5f3-6713-4372-a66c-fad3018ef5c6.
International Search Report issued in International Appl. No. PCT/US2015/031788, dated Aug. 26, 2015.
International Search Report issued in International Appl. No. PCT/US2016/061167, dated Dec. 27, 2016.
International Search Report issued in International Appl. No. PCT/US2017/020008, dated May 23, 2017.
International Search Report issued in International Appl. No. PCT/US2017/020795, dated Jun. 16, 2017.
Non-final Office Action issued in co-pending U.S. Appl. No. 15/153,510, dated Jan. 23, 2017.
Final Office Action issued in co-pending U.S. Appl. No. 15/153,510, dated Jun. 9, 2017.
Non-final Office Action issued in co-pending U.S. Appl. No. 15/354,568, dated Jun. 6, 2017.
Non-final Office Action issued in co-pending U.S. Appl. No. 15/571,482, dated Aug. 3, 2018.
Non-final Office Action issued in co-pending U.S. Appl. No. 15/833,699, dated May 29, 2018.
Final Office Action in U.S. Appl. No. 15/571,482, dated Dec. 18, 2018.
PCT/US2016/060391, "International Search Report and Written Opinion", dated Jan. 10, 2017, 9 pages.

\* cited by examiner

TOPICAL FORMULATIONS AND USES THEREOF

CROSS-REFERENCES TO RELATED APPLICATIONS

This application is a continuation of U.S. application Ser. No. 14/629, filed on Feb. 24, 2015, and entitled TOPICAL FORMULATIONS AND USES THEREOF, which is a continuation of International Application No. PCT/US2013/056513, filed on Aug. 23, 2013, and entitled OPHTHALMIC FORMULATION OF POLYOXYL LIPID OR POLYOXYL FATTY ACID AND TREATMENT OF OCULAR CONDITIONS, which is a non-provisional of U.S. Provisional Application No. 61/693,189, filed on Aug. 24, 2012, and entitled TOPICAL FORMULATIONS AND USES THEREOF, the entirety of which are incorporated by reference herein.

FIELD OF THE INVENTION

The present disclosure relates to the field of formulations for topical administration, such as ophthalmic formulations, and methods of using such formulations.

BACKGROUND OF THE INVENTION

The information provided herein and references cited are provided solely to assist the understanding of the reader, and does not constitute an admission that any of the references or information is prior art to the present invention.

United States Patent Application Nos US2010/0310462 and US2009/0092665 disclose drug delivery systems for ophthalmic use that have nanomicelles that include vitamin E TPGS.

Travoprost involves a formulation for glaucoma or ocular hypertension that includes HCO-40 and a prostaglandin analog as the active ingredient. See dailymed.nlm.nih.gov/dailymed/lookup.cfm?setid=338e7ff4-0d91-4208-a45d-bfa2be52334d on the world-wide web. The active ingredient is present at 0.004%. The formulation includes propylene glycol and does not include nanomicelles. HCO-40 is present in Travoprost at 0.5%. See ema.europa.eu/docs/en_GB/document_library/EPAR_-_Product_Information/human/000665/WC500038389.pdf on the world-wide web.

SUMMARY OF THE INVENTION

The present disclosure relates to topical formulations such as formulations suitable for ophthalmic administration of an active ingredient. In certain aspects and embodiments, the formulations of the present disclosure may include a polyoxyl lipid or fatty acid, and or a polyalkoxylated alcohol and may include nanomicelles.

In certain aspects and embodiments as described herein, the formulations as described herein may have certain surprising features and advantages that could not have been predicted prior to the present disclosure. For example, formulations of the instant disclosure may be able to support a dose of an active ingredient such as a hydrophobic active ingredient that is surprisingly higher than many prior art formulations. The dose of an active ingredient or agent used in the formulations described herein may be selected based on various criteria, including the amount that the formulation can support, the desired dose for various therapeutic applications, etc. In this regard, in some embodiments the active ingredient (such as for ophthalmic administration) the active agent may be at least about 0.05%, or at least about 0.08%, or at least about 0.09%, or at least about 0.1%, or at least about 0.15%; or at least about 0.2%: or at least about 0.3%: or at least about 0.4%; or at least about 0.5%; or at least about 0.6%; or at least about 0.7%; or at least about 0.8%; or at least about 0.9%; or at least about 1.0%; or at least about 1.5%; or at least about 2%; or at least about 3%; or at least about 4%; or at least about 5%; or between 0.05 and 5%; or between 0.05 and 0.5%; or between 0.05 and 0.2%, or between 0.08 and 0.12%; or between 0.1 and 0.5%, or between 0.5 and 1%, or between 0.5 and 1.5%; or between 1 and 5%; or between 2 and 4%; or between 4 and 6% of the formulation. In some embodiments the formulation has nanomicelles with a relatively increased entrapment efficiency; in such embodiments the active agent (such hydrophobic active agents for ophthalmic administration) may be at least about 0.05%, or at least about 0.08%, or at least about 0.09%, or at least about 0.1%, or at least about 0.15%; or at least about 0.2%: or at least about 0.3%: or at least about 0.4%; or at least about 0.5%; or at least about 0.6%; or at least about 0.7%; or at least about 0.8%; or at least about 0.9%; or at least about 1.0%; or at least about 1.5%; or at least about 2%; or at least about 3%; or at least about 4%; or at least about 5%; or between 0.05 and 5%; or between 0.05 and 0.5%; or between 0.05 and 0.2%, or between 0.08 and 0.12%; or between 0.1 and 0.5%, or between 0.5 and 1%, or between 0.5 and 1.5%; or between 1 and 5%; or between 2 and 4%; or between 4 and 6% of the formulation and is present in nanomicelles of the formulation. In certain aspects and embodiments, the formulations of the disclosure are surprisingly effective in dissolving and/or delivering active ingredients (such as hydrophobic active ingredients) without a need for organic solvents (such as propylene glycol) that can be an irritant when included in ophthalmic formulations. In some embodiments, the formulations of the present disclosure are surprisingly stable at high temperatures, for example, temperatures above about 40 degrees C. In some aspects and embodiments the nanomicellular nature of some formulations described herein allow for improved ocular tissue distribution. In certain aspects and embodiments, formulations as described herein are particularly suitable for anterior eye delivery, or posterior eye delivery, or anterior and posterior eye delivery. Moreover, the formulations of certain aspects and embodiments of the disclosure may have the surprising advantage of being adaptable to facilitate delivery of active agents having various sizes or properties; for example, in certain embodiments in formulations that include a polyoxyl castor oil, HCO-60 could be used for active agents having relatively small molecule sizes and HCO-80 and/or HCO-100 could be used for relatively larger sized active agents.

Accordingly, in a first aspect provided is an ophthalmic formulation that includes an active agent, a polyoxyl lipid or fatty acid and a polyalkoxylated alcohol. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-60. In some embodiments the polyoxyl lipid is HCO-80. In some embodiments the polyoxyl lipid is HCO-100. In some embodiments, the formulation includes a polyalkoxylated alcohol that is octoxynol-40. In some embodiments, the formulation includes a polyalkoxylated alcohol (such as octoxynol-40) present between 0.002 and 4%; or between 0.005 and 3%; or 0.005 and 2%; or 0.005 and 1%; or 0.005 and 0.5%; or 0.005 and 0.1%; or 0.005 and 0.05%; or 0.008 and 0.02%; or about 0.01% by weight of the formulation.

As used herein, the term "polyoxyl lipid or fatty acid" refers to mono- and diesters of lipids or fatty acids and polyoxyethylene diols. Polyoxyl lipids or fatty acids may be numbered ("n") according to the average polymer length of the oxyethylene units (e.g., 40, 60, 80, 100) as is well understood in the art. The term "n≥40 polyoxyl lipid" means that the ployoxyl lipid or fatty acid has an average oxyethylene polymer length equal to or greater than 40 units. Stearate hydrogenated castor oil and castor oil are common lipids/fatty acids commercially available as polyoxyl lipids or fatty acid, however, it is understood that any lipid or fatty acid could polyoxylated to become a polyoxyl lipid or fatty acid as contemplated herein. Examples of polyoxyl lipid or fatty acids include without limitation HCO-40, HCO-60, HCO-80, HCO-100, polyoxyl 40 stearate, polyoxyl 35 castor oil.

In some embodiments of any of the compositions and methods described herein, the average polymer length of the oxyethylene units of a polyoxyl lipid or fatty acid is longer for a relatively larger active ingredient and is shorter for a relatively smaller active ingredient; for example in some embodiments in which the active ingredient is a resolvin or resolvin-like compound the polyoxyl lipid is HCO-60 and in some embodiments where the active ingredient is cyclosporine A (which is larger than a resolvin) the polyoxyl lipid is HCO-80 or HCO-100.

As used herein, the term "micelle" or "nanomicelle" refers to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a mixed micelle. The in some embodiments, ophthalmic compositions of the present disclosure include an aqueous, clear, mixed micellar solution In a second aspect, provided is an ophthalmic formulation, comprising an active agent, and a n≥40 polyoxyl lipid or fatty acid. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.5 and 2%, or 0.7 and 2%, or 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a third aspect, provided is an ophthalmic formulation, that includes an active ingredient (such as a hydrophobic active ingredient) and a polyoxyl lipid or fatty acid; wherein said polyoxyl lipid or fatty acid is present in an amount equal to or greater than 1% of said formulation. In a similar aspect, provided is an ophthalmic formulation, that includes an active ingredient (such as a hydrophobic active ingredient) and a polyoxyl lipid or fatty acid; wherein said polyoxyl lipid or fatty acid is present in an amount equal to or greater than 0.05% of said formulation. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-60, HCO-80 or HCO-100) is present between 0.5 and 2%, or 0.7 and 2%, or between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a fourth aspect, provided is an ophthalmic formulation, that includes an active agent and a polyoxyl lipid or fatty acid; wherein said formulation comprises nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.5 and 2%, or 0.7 and 2%, or between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40)

present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a further aspect provided is an ophthalmic formulation, comprising an active agent, 1-5% of one or more selected from the group consisting of HCO-40, HCO-60, HCO-80 and HCO-100; and about 0.01% octoxynol-40.

In another aspect, provided is ophthalmic formulation, comprising an active agent, 1-5% of one or more selected from the group consisting of HCO-40, HCO-60, HCO-80 and HCO-100; and about 0.01% octoxynol-40.

In yet another aspect, provided is an ophthalmic formulation, comprising an active agent, 1-5% of one or more selected from the group consisting of HCO-40, HCO-60, HCO-80 and HCO-100; and about 0.01% octoxynol-40.

In one aspect, provided is an ophthalmic formulation, comprising an active agent, 1-5% of one or more selected from the group consisting of HCO-40, HCO-60, HCO-80 and HCO-100; and about 0.01% octoxynol-40.

In a further aspect provided is an ophthalmic formulation, comprising an active agent, about 4% of HCO-60 and about 0.01% octoxynol-40.

In another aspect provided is an ophthalmic formulation, comprising an active agent, 0.7-1.5% of one or more selected from the group consisting of HCO-40, HCO-60, HCO-80 and HCO-100; and about 0.05% octoxynol-40.

In another aspect, provided is ophthalmic formulation, comprising an active agent, 0.7-1.5% of one or more selected from the group consisting of HCO-40, HCO-60, HCO-80 and HCO-100; and about 0.05% octoxynol-40.

In yet another aspect, provided is an ophthalmic formulation, comprising an active agent, 0.7-1.5% of one or more selected from the group consisting of HCO-40, HCO-60, HCO-80 and HCO-100; and about 0.05% octoxynol-40.

In one aspect, provided is an ophthalmic formulation, comprising an active agent, 0.7-1.5% of one or more selected from the group consisting of HCO-40, HCO-60, HCO-80 and HCO-100; and about 0.05% octoxynol-40.

In a further aspect provided is an ophthalmic formulation, comprising an active agent, about 1% of HCO-60 and about 0.05% octoxynol-40.

In various embodiments of any of the aspects and embodiments described herein, the formulation includes nanomicelles.

In some embodiments of the aspects and embodiments described herein, the formulation includes a polyoxyl lipid or fatty acid. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-60, HCO-80 or HCO-100) is present between 0.5 and 2%, or 0.7 and 2%, or 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100.

In some embodiments of the aspects and embodiments disclosed herein, includes a polyalkoxylated alcohol. In some embodiments, the formulation includes a polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In certain aspects and embodiments disclosed herein, the active agent is one or more selected from the group consisting of calcineurin inhibitors, mTOR inhibitors, peptides, eicosanoids (e.g. prostacyclins and prostaglandins), anti-inflammatory drugs (such as NSAIDS), autonomic drugs (e.g. beta-blockers, alpha-blockers, beta-agonists, and alpha-agonists), biologics, gene therapy agents (e.g. viral vectors), anti-infectives (e.g. antifungals, antibiotics, and antivirals), retinoids, RNAi, photo sensitizers, steroids (e.g., estrogens and derivatives thereof, and corticosteroids), mixture drugs, immuno-modulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists, resolvins (resolvin-like compounds), lipoxins, neuroprotectins, maresins and oxylipins.

In some embodiments, the active ingredient is one or more selected from the group consisting of cyclosporine A, voclosporin, ascomycin, tacrolimus, pimecrolimus, an analog thereof, or a pharmaceutically acceptable salt thereof. In one embodiment, the active agent is cyclosporine A. In one embodiment, the active agent is voclosporin.

In some embodiments, the active ingredient is one or more selected from the group consisting of sirolimus (rapamycin), temsirolimus, everolimus, an analog thereof, or a pharmaceutically acceptable salt thereof.

In certain aspects and embodiments disclosed herein, the active agent is a resolvin or a resolvin-like compound. As used herein a resolvin-like compound includes resolvins and compounds with similar structures and/or features. Resolvins and resolvin-like compounds include a compound of formula A, a compound of any one of formulae 1-49, a compound of any one of formulae I-IX, a lipoxin compound, an oxylipin compound, a prodrug of any of the foregoing, or a pharmaceutically acceptable salt of any of the foregoing. In some embodiments the active agent is a compound selected from a compound of any one of Formulae 1 to 115.

In some embodiments of any of the aspects and embodiments disclosed herein, the active agent is a compound of formula I, (I)

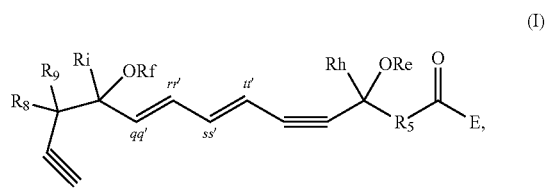

and pharmaceutically acceptable salts thereof, wherein:
the stereochemistry of the carbon qq' to carbon rr' double bond is cis or trans;

the stereochemistry of the carbon ss' to carbon tt' double bond is cis or trans;

Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl;

E is a branched alkoxy such as isopropoxy, isobutoxy, sec-butoxy, tert-butoxy, 3-methylbutoxy, 2,2-dimethylpropoxy, or 1,1,2-trimethylpropoxy;

Rh and Ri are independently selected from hydrogen, alkyl, alkenyl, alkynyl, perfluoroalkyl, aryl or heteroaryl;

$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, or $CH_2CH_2$; or iv) $R_5$ is a carbocyclic, heterocyclic, aryl or heteroaryl ring; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring.

In certain embodiments, a compound of formula I is represented by formula II,

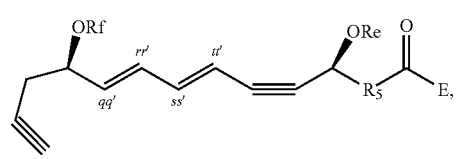

(II)

and pharmaceutically acceptable salts thereof, wherein:
the stereochemistry of the carbon qq' to carbon rr' double bond is cis or trans;
the stereochemistry of the carbon ss' to carbon tt' double bond is cis or trans; and
Re, Rf, $R_5$, and E are as defined above.

In certain embodiments, a compound of formula I or II is represented by formula III,

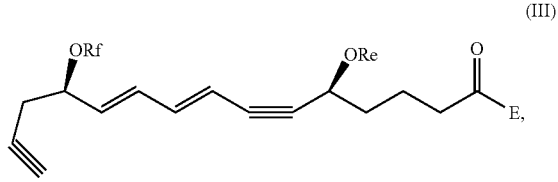

(III)

and pharmaceutically acceptable salts thereof, wherein:
Re, Rf, and E are as defined above.

In some embodiments of any of the aspects disclosed herein, the active agent is a compound of formula I, wherein: Re, Rf, Rh, Ri, $R_8$ and $R_9$ are hydrogen; E is branched alkoxy (such as isopropyl); and $R_5$ is $CH_2CH_2CH_2$.

In some embodiments of any of the aspects disclosed herein, the active agent is a compound 1001 or a pharmaceutically acceptable salt thereof.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

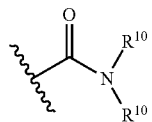

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

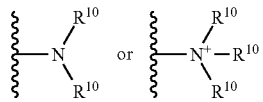

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

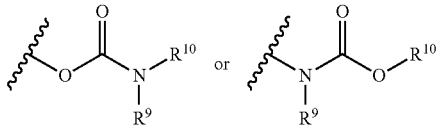

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

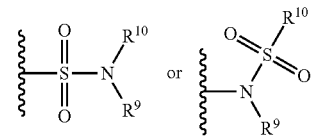

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

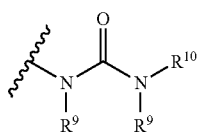

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The instant disclosure further relates to treating or preventing ocular diseases or disorders, for example by local administration of the formulations as described herein.

A patient or subject to be treated by any of the compositions or methods of the present disclosure can mean either a human or a non-human animal. In an embodiment, the present disclosure provides methods for the treatment of an ocular disease in a human patient in need thereof. In an embodiment, the present disclosure provides methods for the treatment of an inflammatory ocular disease in a human patient in need thereof. In another embodiment, the present disclosure provides methods for the treatment of an ocular disease in a veterinary patient in need thereof, including, but not limited to dogs, horses, cats, rabbits, gerbils, hamsters, rodents, birds, aquatic mammals, cattle, pigs, camelids, and other zoological animals.

In some embodiments of the compositions and methods disclosed herein, the active agent includes a combination of two or more different active ingredients. In some embodiments the active agent includes two or more active agents selected from the group consisting of a resolvin or resolvin-like compound, a steroid (such as a corticosteroid), cyclosporine A, and voclosporin. In some embodiments the active agent includes a resolvin and cyclosporine A. In some embodiments the active agent includes a resolvin and a corticosteroid. In some embodiments the active agent includes cyclosporine A and a corticosteroid. In some embodiments, the active agent includes a resolvin, cyclosporine A and a corticosteroid. In some embodiments, the active agent includes two or more active agents and one of said active agents is an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the active agent includes two or more active agents and one of the active agents is an antibiotic, for example one or more antibiotics selected from the group consisting of azythromycin, ciprofloxacin, ofloxacin, gatifloxacin, levofloxacin, moxifloxacin, besifloxacin, and levofloxacin; and a second of such agents is a resolvin such as described herein (including without limitation compound 1001). In some embodiments, the active agent includes two or more active agents and one of said active agents is an antiviral, for example one or more antivirals selected from the group consisting of ganciclovir, trifluridine, acyclovir, famciclovir, valacyclovir, penciclovir and cidofovir. In some embodiments, the active agent includes two or more active agents and one of the active agents is an antibiotic, for example one or more antivirals selected from the group consisting of ganciclovir, trifluridine, acyclovir, famciclovir, valacyclovir, penciclovir and cidofovir; and a second of the active agents is a resolvin such as described herein (including without limitation compound 1001).

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the terms "ocular disease," "ocular condition," "eye disease," and "eye condition" refer to diseases/conditions of the eye(s) that can be sight threatening, lead to eye discomfort, and may signal systemic health problems.

As used herein, the term "anterior segment disease" refers to all disorders that affect the eye surface, anterior chamber, iris and ciliary body and lens of the eye. The eye surface is composed of the cornea, conjunctiva, eyelids, lacrimal and meibomian glands, and the interconnecting nerves.

As used herein, the terms "posterior segment eye disease" and "back-of-the-eye disease" refer to all disorders that affect the posterior segment of the eye. A posterior eye disease is a disease which primarily affects a posterior ocular site such as choroid or sclera, vitreous, vitreous chamber, retina, optic nerve, and blood vessels and nerves which vascularize or innervate a posterior ocular site.

Accordingly, in one aspect, provided is a method treating or preventing an ocular disease or condition, that includes locally administering a formulation of any of the aspects or embodiments as disclosed herein. In some embodiments, the ocular disease is an anterior segment disease. In some embodiments, the ocular disease is a posterior segment disease. In some embodiments, the ocular disease is one or more selected from the group consisting of dry eye syndrome, Sjogren's syndrome, uveitis, anterior uveitis (iritis), chorioretinitis, posterior uveitis, conjunctivitis, allergic conjunctivitis, keratitis, keratoconjunctivitis, vernal keratoconjunctivitis (VKC), atopic keratoconjunctivitis, systemic immune mediated diseases such as cicatrizing conjunctivitis and other autoimmune disorders of the ocular surface, blepharitis, scleritis, age-related macular degeneration (AMD), diabetic retinopathy (DR), diabetic macular edema (DME), ocular neovascularization, age-related macular degeneration (ARMD), proliferative vitreoretinopathy (PVR), cytomegalovirus (CMV) retinitis, optic neuritis, retrobulbar neuritis, and macular pucker. In one embodiment, the ocular disease is dry eye. In one embodiment, the ocular disease is allergic conjunctivitis. In one embodiment the ocular disease is age-related macular degeneration (AMD). In one embodiment the ocular disease is diabetic retinopathy.

DETAILED DESCRIPTION OF THE PREFERRED EMBODIMENTS

Active Agents

In accordance various aspects and embodiments of the methods and compositions provided herein, an active agent can be any agent capable of affecting a biological process. Active agents (the term active ingredient is used herein interchangably with the term active agent) include drugs, hormones, cytokines, toxins, therapeutic agents, vitamins and the like. In some embodiments an active agent in accordance with the aspects and embodiments disclosed herein is an agent capable of, or approved for, treating or preventing an disease or condition, for example in some embodiments an active agent is capable of, or approved for, treating or preventing an ocular disease or condition.

The compositions of the present disclosure can be used as a topically applied or locally injected drug delivery platform for delivery of a variety of active agents including hydrophobic, water-insoluble drugs. Active agents may include calcineurin inhibitors or mTOR inhibitors, peptides, eicosanoids (e.g. prostacyclins and prostaglandins), anti-inflammatory drugs, autonomic drugs (e.g. beta-blockers, alpha-blockers, beta-agonists, and alpha-agonists), biologics, gene therapy agents (e.g. viral vectors), anti-infectives (e.g. anti-fungals, antibiotics, and antivirals), retinoids, RNAi, photo sensitizers, steroids (e.g., estrogens and derivatives thereof), mixture drugs, immuno-modulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists, resolvins, lipoxins, oxylipins and the like. In some embodiments, the active agent is a corticosteroid, including prednisolone, hydrocortisone, triamcinolone and budesonide. In certain embodiments the active ingredient may be a non-steroidal anti-inflammatory drug (NSAID), for example Cox-2 inhibitors such as celecoxib, ruboxistaurin and nimesulide. In certain embodiments an active agent may be an anti-growth factor molecules include, but are not limited to, vascular endothelial growth factor (VEGF) inhibitors such as, pegaptanib (macugen), ranibizumab (lucentis), and bevacizumab (avastin). In some embodiments, the active agent is an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the active agent is an antiviral, for example one or more antivirals selected from the group consisting of ganciclovir, trifluridine, acyclovir, famciclovir, valacyclovir, penciclovir and cidofovir.

In some embodiments a combination of two active agents may be used, including but not limited to a vascular endothelial growth factor (VEGF) inhibitor and an antagonist of platelet-derived growth factor (PDGF).

In some embodiments of any of the aspects and embodiments disclosed herein, the active agent may be a calcineurin inhibitor such as cyclosporine A, voclosporin, ascomycin, tacrolimus, pimecrolimus, an analog thereof, or a pharmaceutically acceptable salt thereof.

In some embodiments of any of the aspects and embodiments disclosed herein, the active agent may be a mTOR inhibitor such as sirolimus (rapamycin), temsirolimus, everolimus, an analog thereof, or a pharmaceutically acceptable salt thereof.

A calcineurin inhibitor of the present disclosure is preferably an immunophilin-binding compound having calcineurin inhibitory activity. Immunophilin-binding calcineurin inhibitors are compounds forming calcineurin inhibiting complexes with immunophilins, e.g. cyclophilin and macrophilin. Examples of cyclophilin-binding calcineurin inhibitors are cyclosporines or cyclosporine derivatives (hereinafter cyclosporines) and examples of macrophilin-binding calcineurin inhibitors are ascomycin (FR 520) and ascomycin derivatives (hereinafter ascomycins). A wide range of ascomycin derivatives are known, which are either naturally occurring among fungal species or are obtainable by manipulation of fermentation procedures or by chemical derivatization. Ascomycin-type macrolides include ascomycin, tacrolimus (FK506), sirolimus and pimecrolimus.

Cyclosporine, originally extracted from the soil fungus *Potypaciadium infilatum*, has a cyclic 11-amino acid structure and includes e.g. Cyclosporines A through I, such as Cyclosporine A, B, C, D and G. Cyclosporine binds to the cytosolic protein cyclophilin of immunocompetent lymphocytes, especially T-lymphocytes, forming a complex. The complex inhibits calcineurin, which under normal circumstances induces the transcription of interleukin-2 (IL-2). Cyclosporine also inhibits lymphokine production and interleukin release, leading to a reduced function of effector T-cells.

Voclosporin is a next-generation calcineurin inhibitor that is a more potent and less toxic semi-synthetic derivative of cyclosporine A. Like other molecules of this class, voclosporin reversibly inhibits immunocompetent lymphocytes, particularly T-lymphocytes, and also inhibits lymphokine production and release. This action is primarily mediated through inhibition of calcineurin, a phosphatase enzyme found in the cytoplasm of cells. Voclosporin has a single carbon extension with double bond that has been shown to extend deeper into the latch/regulatory region of calcineurin. In an embodiment, the compositions of the present disclosure comprise the trans-version of voclosporin, trans-ISA247 CAS RN 368455-04-3 which is described in, for example, US Patent Publication No.: 2006/0217309, which is hereby incorporated herein by reference. Further compositions of voclosporin are described, for example, in U.S. Pat. No. 7,060,672, which is hereby incorporated herein by reference.

Tacrolimus (FK506) is another calcineurin inhibitor which is also a fungal product, but has a macrolide lactone structure. Tacrolimus has been used as an immunosuppressant in conjunction with liver, kidney, heart, lung and heart/lung transplants. Tacrolimus has also been shown to inhibit the production of IL-2. Tacrolimus binds to an immunophilin (FK-binding protein 12, FKBP12), followed by binding of the complex to calcineurin to inhibit its phosphatase activity.

Sirolimus (rapamycin) is a microbial product isolated from the actinomycete *Streptomyces hygroscopicus*. Sirolimus binds to an immunophilin (FK-binding protein 12, FKBP12) forming a complex, which inhibits the mammalian target of rapamycin (mTOR) pathway through directly binding the mTOR Complex1 (mTORC1). Sirolimus inhibits the response to interleukin-2 (IL-2) and thereby blocks activation of T- and B-cells. By contrast, tacrolimus and cyclosporine inhibit the production of IL-2.

Pimecrolimus is a new calcineurin inhibitor which has been found to have antifungal properties against *Malassezia* spp., as does tacrolimus.

Calcineurin inhibitors such as cyclosporine A, voclosporin, ascomycin, tacrolimus, pimecrolimus, an analog thereof, or a pharmaceutically acceptable salt thereof, can be utilized in a mixed micellar composition of the present disclosure. In an embodiment, the calcineurin inhibitor is voclosporin.

mTOR inhibitors such as sirolimus (rapamycin), temsirolimus, everolimus, an analog thereof, or a pharmaceutically acceptable salt thereof, can be utilized in a mixed micellar composition of the present disclosure.

Resolvins, Lipoxins and the Like

In some aspects and embodiments as described herein, the active agent is a resolvin. In certain aspects and embodiments the active ingredient is a compound of formula A, a compound of any one of formulae 1-49, a compound of any one of formulae I-IX, a lipoxin compound, an oxylipin compound, a prodrug of any of the foregoing, or a pharmaceutically acceptable salt of any of the foregoing Compounds suitable for use as active agents in accordance with the aspects and embodiments of the present disclosure include those of Formula A,

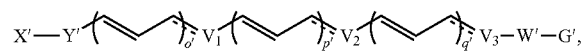

wherein:
each of W' and Y' is a bond or a linker independently selected from a ring containing up to 20 atoms or a chain of up to 20 atoms, provided that W' and Y' can independently include one or more nitrogen, oxygen, sulfur or phosphorous atoms, further provided that W' and Y' can independently include one or more substituents independently selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, or sulfonyl, further provided that W' and Y' can independently contain one or more fused carbocyclic, heterocyclic, aryl or heteroaryl rings, and further provided that when o' is 0, and $V_1$ is

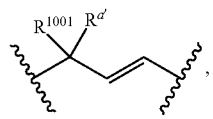

Y' is connected to $V_1$ via a carbon atom;
$V_1$ is selected from

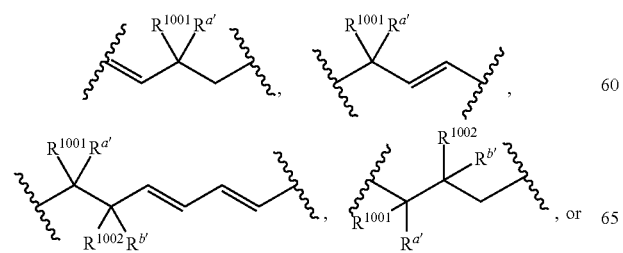

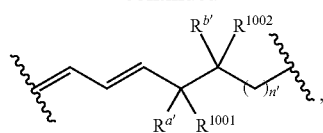

wherein when q' is 0 and $V_3$ is a bond, n' is 0 or 1; otherwise n' is 1;
$V_2$ is selected from a bond,

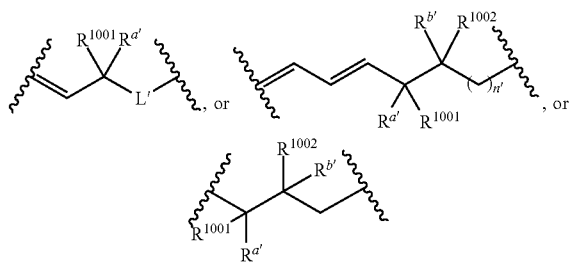

wherein:
L' is selected from —C($R^{1003}$)($R^{1004}$)—, wherein each of $R^{1003}$ and $R^{1004}$ is independently selected from hydrogen, alkyl, alkenyl, alkynyl, perfluoroalkyl, alkoxy, aryl or heteroaryl, or $R^{1003}$ and $R^{1004}$ are connected together to form a carbocyclic or heterocyclic ring; when $V_3$ is

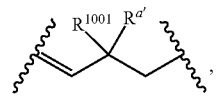

L' is additionally selected from W'; and n' is 0 or 1;
$V_3$ is selected from a bond or

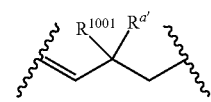

wherein:
each $R^{1001}$ and $R^{1002}$ is independently for each occurrence selected from hydrogen, alkyl, alkenyl, alkynyl, aryl, heteroaryl, alkylaryl, alkoxy, or halo, wherein said alkyl- or aryl-containing moiety is optionally substituted with up to 3 independently selected substituents;
each of $R^{a'}$ and $R^{b'}$ is independently for each occurrence selected from —OR' or —N(R')$_2$, or adjacent $R^{a'}$ and $R^{b'}$ are taken together to form an epoxide ring having a cis or trans configuration, wherein each R' is independently selected from hydrogen, alkyl, alkenyl, alkynyl, aryl, heteroaryl, acyl, silyl, alkoxyacyl, aminoacyl, aminocarbonyl, alkoxycarbonyl, or a protecting group;

or when $V_1$ is

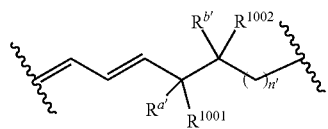

and $V_2$ is

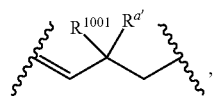

$R^{1002}$ and $R^{b'}$ are both hydrogen;

X' is selected from —CN, —C(NH)N(R")(R"), —C(S)-A', —C(S)R", —C(O)-A', —C(O)—R", —C(O)—SR", —C(O)—NH—S(O)$_2$—R", —S(O)$_2$-A', —S(O)$_2$—R", S(O)$_2$N(R")(R"), —P(O)$_2$-A', —PO(OR")-A', -tetrazole, alkyltetrazole, or —CH$_2$OH, wherein A' is selected from —OR", —N(R")(R") or —OM';

each R" is independently selected from hydrogen, alkyl, aryl, arylalkyl, heteroaryl, heteroarylalkyl or a detectable label molecule, wherein any alkyl-, aryl- or heteroaryl-containing moiety is optionally substituted with up to 3 independently selected substituents; and M' is a cation;

G' is selected from hydrogen, halo, hydroxy, alkyl, aryl, arylalkyl, heteroaryl, heteroarylalkyl, alkoxy, aryloxy, carboxy, amino, alkylamino, dialkylamino, acylamino, carboxamido or a detectable label molecule, wherein any alkyl-, aryl- or heteroaryl-containing moiety is optionally substituted with up to 3 independently selected substituents;

o' is 0, 1, 2, 3, 4, or 5;

p' is 0, 1, 2, 3, 4, or 5;

q' is 0, 1, or 2; and o'+p'+q' is 1, 2, 3, 4, 5 or 6;

wherein:

if $V_2$ is a bond, then q' is 0, and $V_3$ is a bond;

if $V_3$ is

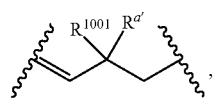

then o' is 0, $V_1$ is

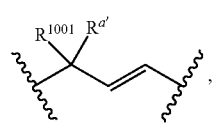

p' is 1 and $V_2$ is

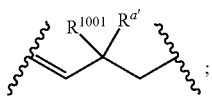

any acyclic double bond may be in a cis or a trans configuration or is optionally replaced by a triple bond; and either one

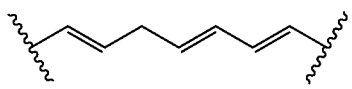 [SMILES: */C=C/C=C/C/C=C/*]

portion of the compound, if present, is optionally replaced by

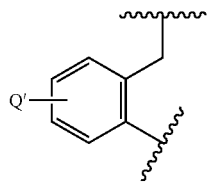

or one

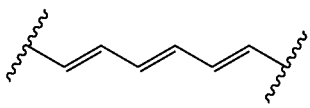 [SMILES: */C=C/C=C/C=C/*]

portion of the compound, if present, is optionally replaced by

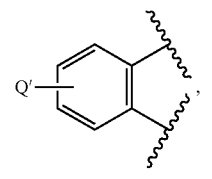

wherein Q' represents one or more substituents and each Q' is independently selected from halo, alkyl, alkenyl, alkynyl, cycloalkyl, aryl, heteroaryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl.

In certain embodiments, $V_1$ is selected from

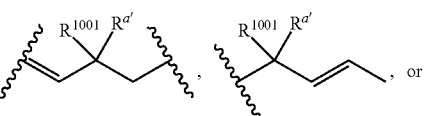

-continued

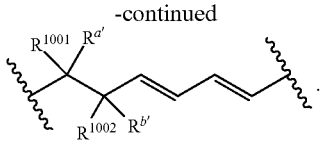

In certain embodiments, V$_2$ is selected from a bond,

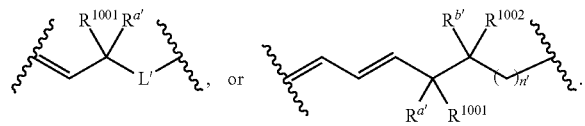

In certain embodiments, when q' is 0 and V$_3$ is a bond, n' is 0 or 1; otherwise n' is 1.

In certain embodiments, p' is 0, 1, 2, 3, or 5.

In certain embodiments, q' is 0 or 1.

In certain embodiments, if V$_1$ is

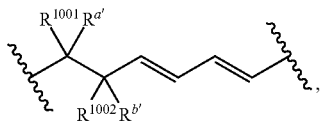

then o' is 0 or 1, p' is 1 or 2, o'+p' is 1 or 2, V$_2$ is

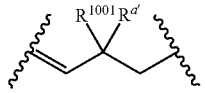

and V$_3$ is a bond.

In certain embodiments, if V$_1$ is

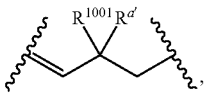

then o' is 3, 4 or 5, p' is 0, 1 or 2, o'+p' is 4 or 5, and V$_2$ is a bond.

In certain embodiments, if V$_2$ is a bond, then o' is 0, 3, 4 or 5; p' is 0, 1, 2 or 5, o'+p' is 4 or 5, q' is 0, and V$_3$ is a bond.

In certain embodiments, each of W' and Y' is independently selected from a bond or lower alkyl or heteroalkyl optionally substituted with one or more substituents independently selected from alkenyl, alkynyl, aryl, chloro, iodo, bromo, fluoro, hydroxy, amino, or oxo.

In certain embodiments, the compound of formula A is other than a compound of formulae 48, 48a, 48b, 48c, or 48d.

In certain embodiments of Formula A, when o' is 2, V$_1$ is

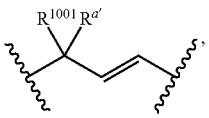

p' is 1, V$_2$ is

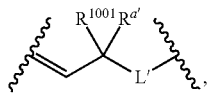

q' is 1, and V$_3$ is a bond, at least one occurrence of R$^{1001}$ is other than hydrogen.

Compounds suitable for use as active agents of the disclosure include those of Formula 1,

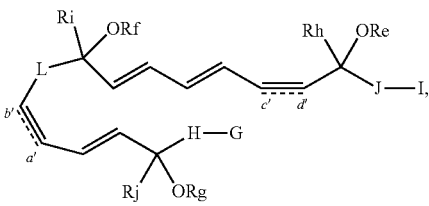

wherein:

Carbons a' and b' are connected by a double bond or a triple bond;

Carbons c' and d' are connected by a double bond or a triple bond;

Re, Rf, and Rg are independently selected from hydrogen, alkyl, alkenyl, alkynyl, aryl, heteroaryl, acyl (e.g., alkoxyacyl, aminoacyl), aminocarbonyl, alkoxycarbonyl, or silyl;

Rh, Ri and Rj are independently selected from hydrogen, alkyl, alkenyl, alkynyl, perfluoroalkyl, aryl or heteroaryl;

I is selected from —C(O)-E, —SO$_2$-E, —PO(OR)-E, where E is hydroxy, alkoxy, aryloxy, amino, alkylamino, dialkylamino, or arylamino; and R is hydrogen or alkyl;

J, L and H are linkers independently selected from a ring containing up to 20 atoms or a chain of up to 20 atoms, provided that J, L and H can independently include one or more nitrogen, oxygen, sulfur or phosphorous atoms, and further provided that J, L and H can independently include one or more substituents selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that J, L and H can also contain one or more fused carbocyclic, heterocyclic, aryl or heteroaryl rings, and provided that linker J is connected to the adjacent C(R) OR group via a carbon atom;

G is selected from hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, or carboxamido;

or pharmaceutically acceptable salts thereof.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

In certain embodiments, a compound of formula 1 is represented by formula 2, (2)

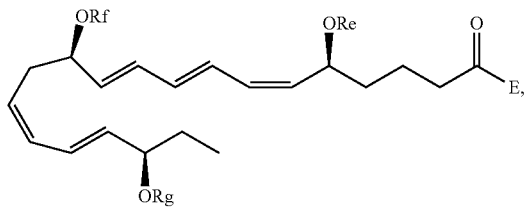

wherein:

E, Re, Rf, and Rg are as defined above.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

Exemplary compounds of formula 2 include compound 2a, (2a)

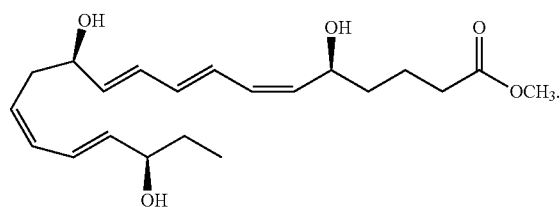

In certain embodiments, a compound of formula 1 is represented by formula 3, (3)

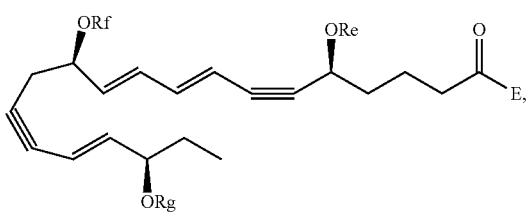

wherein:

E, Re, Rf, and Rg are as defined above.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

Exemplary compounds of formula 3 include compound 3a, (3a)

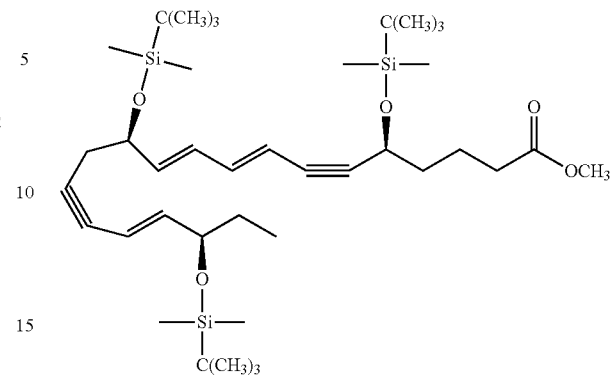

and compound 3b, (3b)

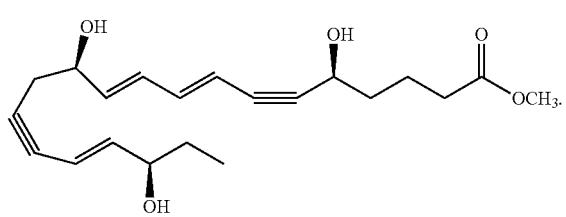

Further exemplary compounds of formula 1 include Compound X, (X)

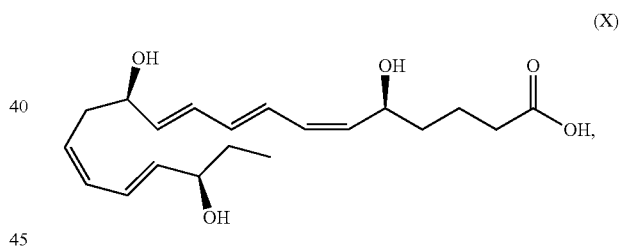

and pharmaceutically acceptable salts and esters thereof.

Other compounds suitable for use as active ingredients include those of Formula 4,

4

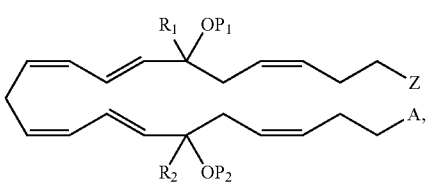

wherein:

A is H or —OP$_4$;

P$_1$, P$_2$ and P$_4$ each individually is a protecting group or hydrogen atom;

R$_1$ and R$_2$ each individually is a substituted or unsubstituted, branched or unbranched alkyl, alkenyl, or alkynyl group, substituted or unsubstituted aryl group, substituted or unsubstituted, branched or unbranched alkylaryl group, halogen atom, hydrogen atom;

Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, —CN, preferably a carboxylic acid, ester, amide, thioester, thiocarboxamide or a nitrile;

each R$^a$, if present, is independently selected from hydrogen, (C1-C6) alkyl, (C2-C6) alkenyl, (C2-C6) alkynyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered heterocyclyl, morpholinyl, piperazinyl, homopiperazinyl, piperidinyl, 4-11 membered heterocyclylalkyl, 5-10 membered heteroaryl and 6-16 membered heteroarylalkyl;

each R$^b$, if present, is a suitable group independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^c$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, [NHC(O)]$_n$NR$^c$R$^c$, —[NR$^a$C(O)]$_n$NR$^c$R$^c$, —[NHC(NH)]$_n$NR$^c$R$^c$ and —[NR$^a$C(NR$^a$)]$_n$NR$^c$R$^c$;

each R$^c$, if present, is independently a protecting group or R$^a$, or, alternatively, two R$^c$ taken together with the nitrogen atom to they are bonded form a 5 to 8-membered heterocyclyl or heteroaryl which optionally including one or more additional heteroatoms and optionally substituted with one or more of the same or different R$^a$ or suitable R$^b$ groups;

each n independently is an integer from 0 to 3;

each R$^d$ independently is a protecting group or R$^a$;

or pharmaceutically acceptable salts thereof.

Exemplary compounds of formula 4 include compound 4a,

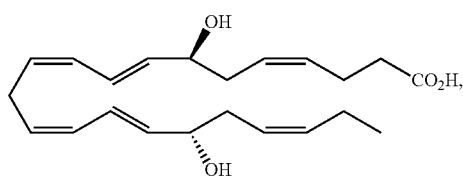

(4a)

compound 4b,

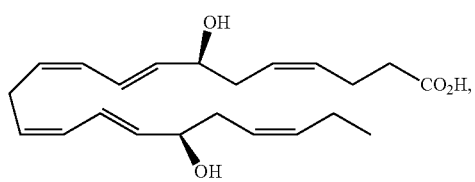

(4b)

and pharmaceutically acceptable salts and esters thereof.

Other compounds suitable for use as active agents include those of Formula 5,

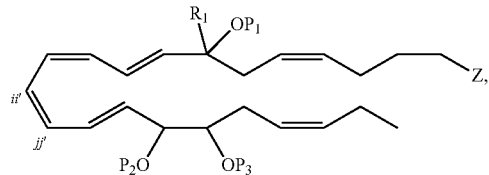

(5)

or pharmaceutically acceptable salts thereof, wherein:

the stereochemistry of the carbon ii' to carbon jj' bond is cis or trans;

P$_3$ is a protecting group or hydrogen atom; and

P$_1$, P$_2$, R$_1$ and Z are as defined above in formula 4.

In certain embodiments, the stereochemistry of the carbon ii' to carbon jj' bond is trans.

Exemplary compounds of formula 5 include compound 5a,

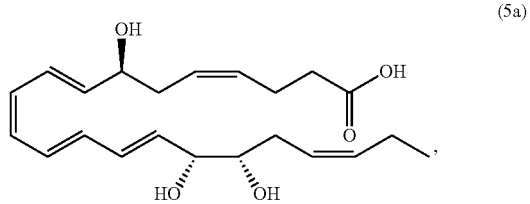 [SMILES: CC/C=C\C[C@H](O)[C@H](O)/C=C/C=C/C=C\C=C\[C@@H](O)C/C=C\CCC(=O)O]

(5a)

compound 5b,

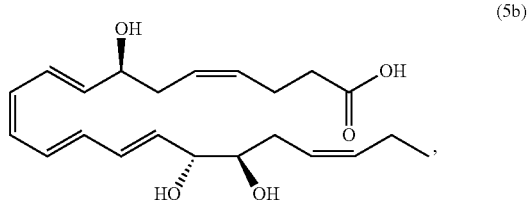 [SMILES: CC/C=C\C[C@@H](O)[C@H](O)/C=C/C=C/C=C\C=C\[C@@H](O)C/C=C\CCC(=O)O]

(5b)

and pharmaceutically acceptable salts and esters thereof.

Other compounds suitable for use as active agents include those of Formula 6,

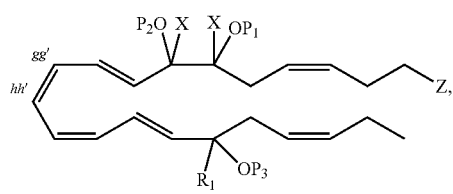

(6)

or pharmaceutically acceptable salts thereof, wherein:

the stereochemistry of the carbon gg' to carbon hh' bond is cis or trans;

each X represents hydrogen or taken together both X groups represent one substituted or unsubstituted methylene, an oxygen atom, a substituted or unsubstituted N atom, or a sulfur atom such that a three-membered ring is formed; and P$_1$, P$_2$, P$_3$, R$_1$ and Z are as defined above.

In certain embodiments, the stereochemistry of the carbon gg' to carbon hh' bond is trans.

Exemplary compounds of formula 6 include compound 6a,

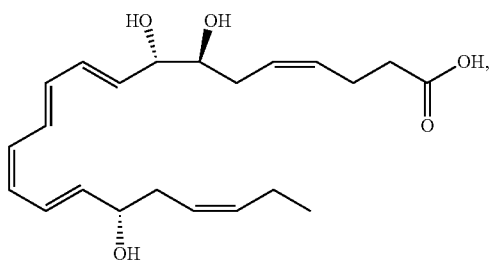

(6a)

compound 6b,

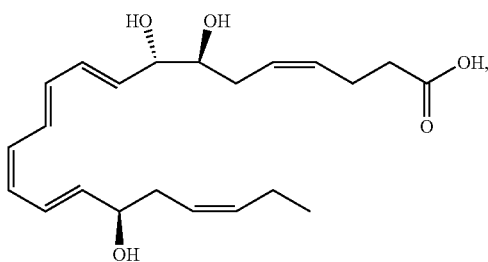

(6b)

and pharmaceutically acceptable salts and esters thereof.

Other compounds suitable for use for use as active agents include those of Formula 7,

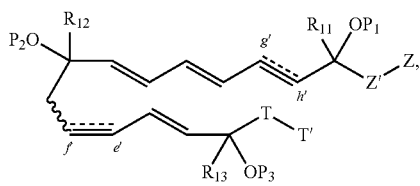

7 or pharmaceutically acceptable salts thereof, wherein:
Carbons e' and f' are connected by a double bond or a triple bond, and when carbon e' is connected to carbon f' through a double bond the stereochemistry is cis or trans;
Carbons g' and h' are connected by a double bond or a triple bond and when carbon g' is connected to carbon h' through a double bond the stereochemistry is cis or trans;
m is 0 or 1;
T' is hydrogen, (C1-C6) alkyl, (C2-C6) alkenyl, (C2-C6) alkynyl, (C5-C14) aryl, (C6-C16) arylalkyl, 5-14 membered heteroaryl, 6-16 membered heteroarylalkyl, or —CH═CHCH$_2$CH$_3$;
T' is —(CH$_2$)$_q$— or —(CH$_2$)$_q$—O—, where q is an integer from 0 to 6;
Z' is (C1-C6) alkylene optionally substituted with 1, 2, 3, 4, 5 or 6 of the same or different halogen atoms, —(CH$_2$)$_p$—O—CH$_2$— or —(CH$_2$)$_m$—S—CH$_2$—, where p is an integer from 0 to 4;
$R_{11}$, $R_{12}$ and $R_{13}$ each individually is substituted or unsubstituted, branched or unbranched alkyl, alkenyl, or alkynyl group, substituted or unsubstituted aryl group, substituted or unsubstituted, branched or unbranched alkylaryl group, $C_{14}$alkoxy, halogen atom, —CH$_2$R$_{14}$, —CHR$_{14}$R$_{14}$, —CR$_{14}$R$_{14}$R$_{14}$, or a hydrogen atom;
$R_{14}$ is independently for each occurrence selected from —CN, —NO$_2$ or halogen; and
$P_1$, $P_2$, $P_3$, and Z are as defined above.

In certain embodiments, carbons e' and f are connected by a cis double bond.

In certain embodiments, carbons g' and h' are connected by a double bond.

In certain embodiments, carbons e' and f are connected by a cis double bond and carbons g' and h' are connected by a double bond.

Exemplary compounds of formula 7 include compound 7a,

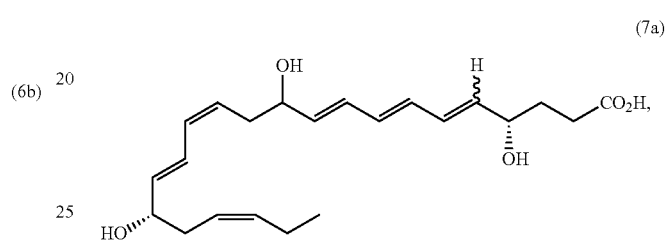

(7a)

compound 7b,

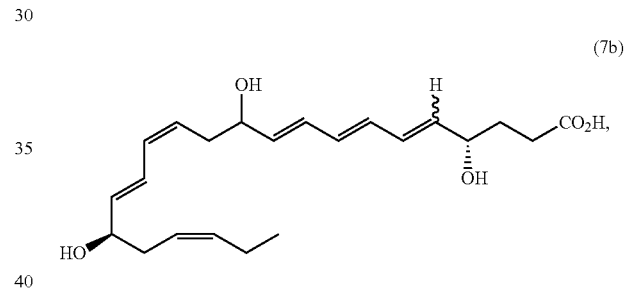

(7b)

and pharmaceutically acceptable salts and esters thereof.

Other compounds suitable for use as active agents include those of Formula 8,

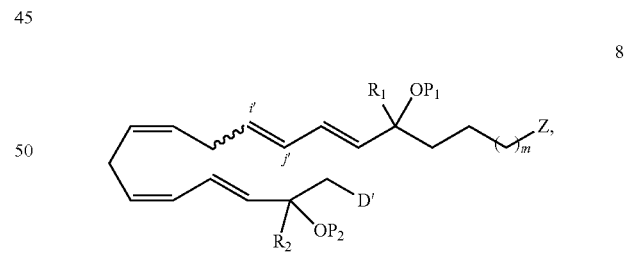

8 or pharmaceutically acceptable salts thereof, wherein:
the stereochemistry of the carbon i' to carbon j' bond is cis or trans;
m is 0 or 1;
D' is CH$_3$, —CH═CHCH$_2$U or —CH═CHCH$_2$CH$_2$A;
U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;
A is H or —OP$_4$;
$P_1$, $P_2$, $P_4$, $R_1$, $R_2$ and Z are as defined above.

In certain embodiments, the stereochemistry of the carbon i' to carbon j' bond is cis.

Exemplary compounds of formula 8 include compound 8a,

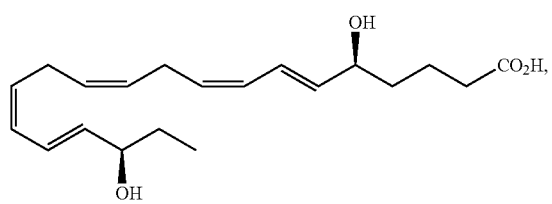

compound 8b,

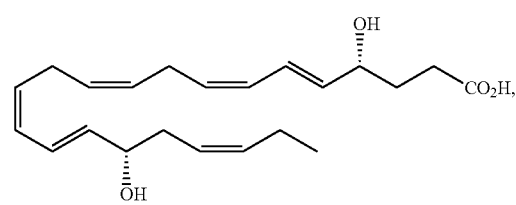

compound 8c,

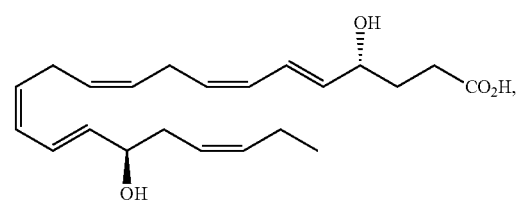

and pharmaceutically acceptable salts and esters thereof.

Other compounds suitable for use as active agents include those of Formula 9,

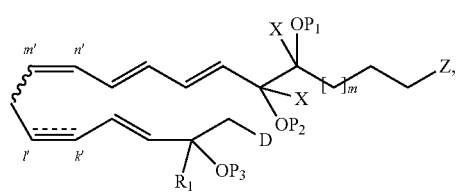

or pharmaceutically acceptable salts thereof, wherein:
Carbons k' and l' are connected by a double bond or a triple bond, and when carbon k' is connected to carbon l' through a double bond the stereochemistry is cis or trans;
the stereochemistry of the carbon m' to carbon n' double bond is cis or trans;
m is 0 or 1;
D is —CH$_3$ or —CH=CHCH$_2$CH$_3$;
P$_1$, P$_2$, P$_3$, R$_1$, X, and Z are as defined above.

In certain embodiments, the stereochemistry of the carbon m' to carbon n' double bond is cis.

In certain embodiments, carbons k' and l' are connected by a cis double bond.

In certain embodiments, the stereochemistry of the carbon m' to carbon n' double bond is cis and carbons k' and l' are connected by a cis double bond.

Exemplary compounds of formula 9 include compound 9a,

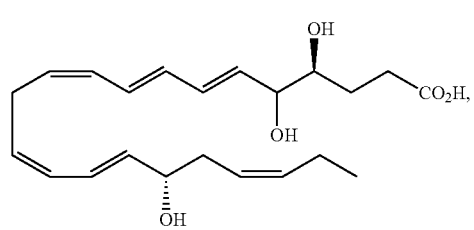

compound 9b,

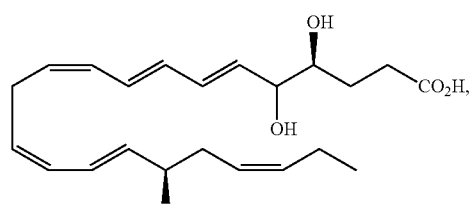

and pharmaceutically acceptable salts and esters thereof.

Other compounds suitable for use for use as active agents include those of Formula 10,

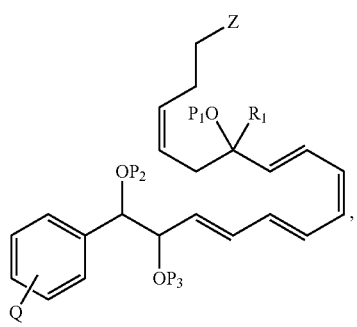

or pharmaceutically acceptable salts thereof, wherein:
P$_1$, P$_2$, P$_3$, R$_1$ and Z are as defined above; and
Q represents one or more substituents and each Q individually, if present, is a halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group.

Other compounds suitable for use for use as active agents include those of Formula 11,

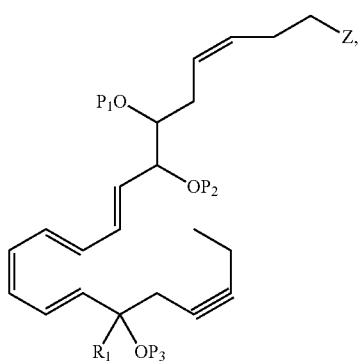

or pharmaceutically acceptable salts thereof, wherein:
$P_1$, $P_2$, $P_3$, $R_1$, and Z are as defined above.

Other compounds suitable for use as active agents include those of Formula 12,

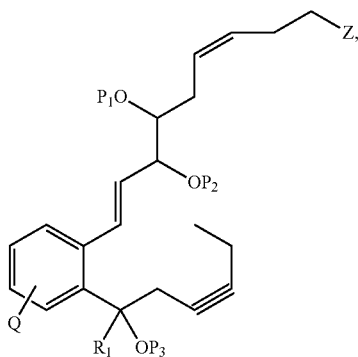

or pharmaceutically acceptable salts thereof, wherein
$P_1$, $P_2$, $P_3$, Q, $R_1$, and Z are as defined above.

Other compounds suitable for use as active agents include those of Formula 13,

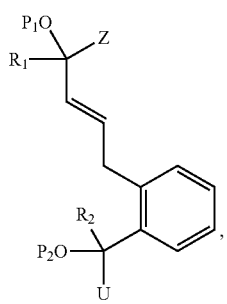

or pharmaceutically acceptable salts thereof, wherein:
$P_1$, $P_2$, $R_1$, $R_2$, U, and Z are as defined above.

Other compounds suitable for use as active agents include those of Formula 14,

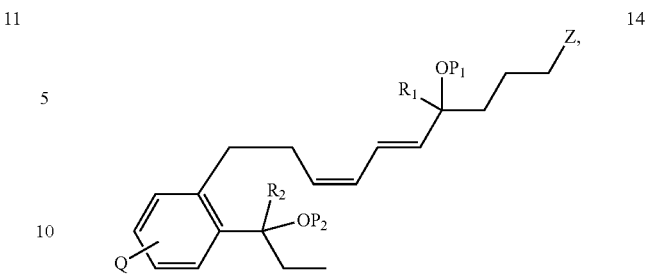

or pharmaceutically acceptable salts thereof, wherein:
$P_1$, $P_2$, $R_1$, $R_2$, Q, and Z are as defined above.

Other compounds suitable for use as active aents include those of Formula 15,

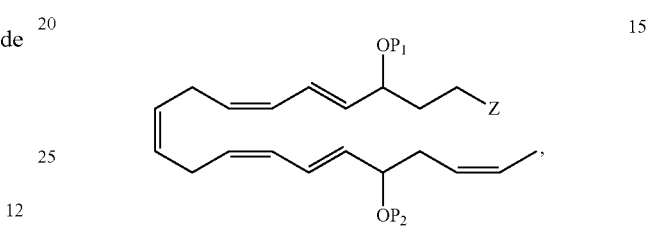

or pharmaceutically acceptable salts thereof, wherein:
$P_1$, $P_2$, and Z are as defined above.

Other compounds suitable for use as active agents include those of Formula 16,

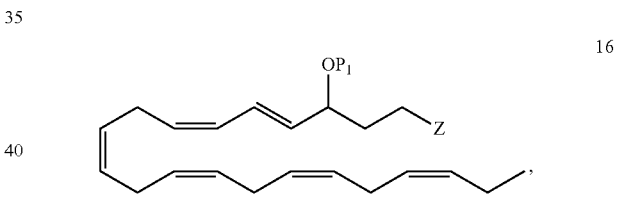

or pharmaceutically acceptable salts thereof, wherein:
$P_1$ and Z are as defined above.

Other compounds suitable for use as active agents include those of Formula 17,

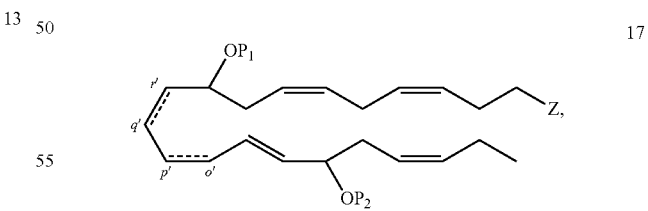

or pharmaceutically acceptable salts thereof, wherein:
Carbons o' and p' are connected by a single or a double bond (e.g., a cis or trans double bond);
Carbons q' and r' are connected by a single or a double bond (e.g., a cis or trans double bond); and
$P_1$, $P_2$, and Z are as defined above.

Other compounds suitable for use as active agents include those of Formula 18,

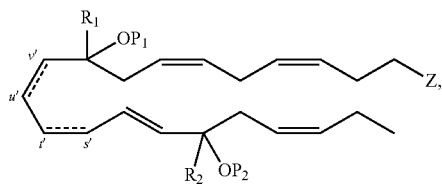

or pharmaceutically acceptable salts thereof, wherein:

the stereochemistry of the carbon s' to carbon t' double bond is cis or trans;

the stereochemistry of the carbon u' to carbon v' double bond is cis or trans; and $P_1$, $P_2$, $R_1$, $R_2$, and Z are as defined above.

Other compounds suitable for use as active agents include those of Formula 19,

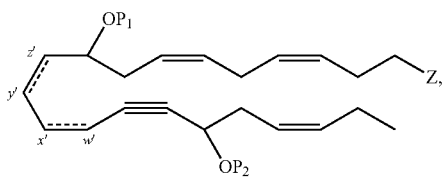

or pharmaceutically acceptable salts thereof, wherein:

Carbons w' and x' are connected by a single or a double bond;

Carbons y' and z' are connected by a single or a double bond; and $P_1$, $P_2$, and Z are as defined above.

In certain embodiments of formulae 4 to 19, each $R^b$, if present, is a suitable group independently selected from =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)R^cR^c$, —$[NHC(O)]_nR^d$, —$[NR^aC(O)]_nR^d$, —$[NHC(O)]_nOR^d$, —$[NHC(O)]_nNR^cR^c$, —$[NR^aC(O)]_nNR^cR^c$, —$[NHC(NH)]_nNR^cR^c$ and —$[NR^aC(NR^a)]_nNR^cR^c$.

Other compounds suitable for use as active agents include those or

Formula 20,

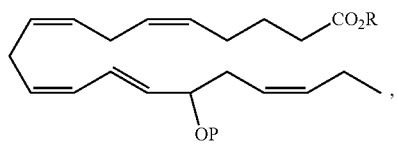

Formula 21,

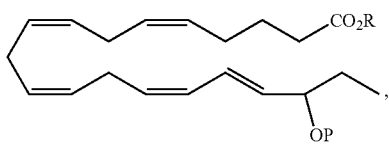

Formula 22,

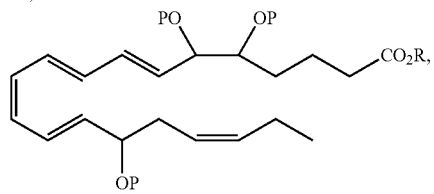

Formula 23,

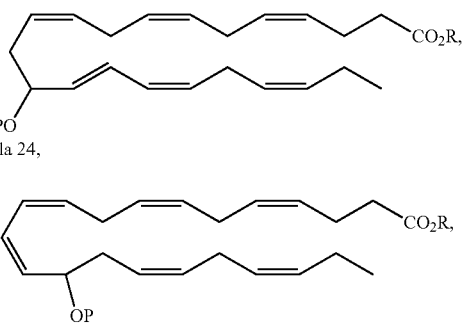

Formula 24,

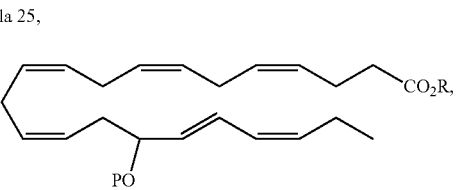

Formula 25,

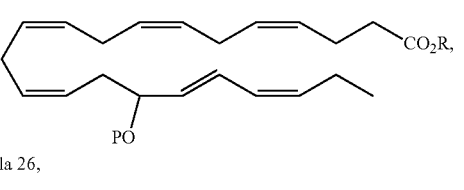

Formula 26,

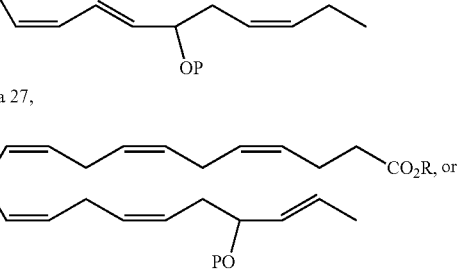

Formula 27,

Formula 28,

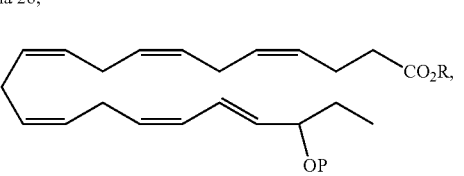

or pharmaceutically acceptable salts of any of the above, wherein each P is individually selected from H or a protecting group; and R is H, $C_{1-6}$alkyl (e.g., methyl, ethyl, glycerol), $C_{2-6}$alkenyl or $C_{2-6}$alkynyl.

Exemplary compounds of formula 21 include compound 21a,

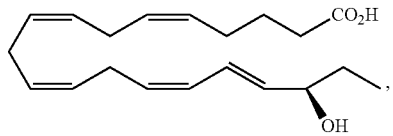
(21a)

and pharmaceutically acceptable salts and esters thereof.

Other compounds suitable for use as active agents include those of Formula 29,

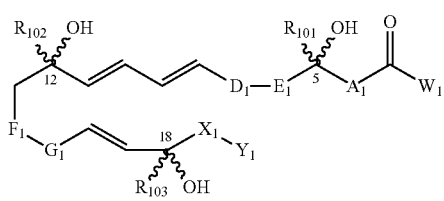
29 and pharmaceutically acceptable salts, hydrates and solvates thereof, wherein:

$D_1$-$E_1$ and $F_1$-$G_1$ are independently are cis or trans —C=C— or —C≡C—;

$R_{101}$, $R_{102}$ and $R_{103}$ are independently selected from hydrogen, (C1-C4) straight-chained or branched alkyl, (C2-C4) alkenyl, (C2-C4) alkynyl, (C1-C4) alkoxy, $CH_2R_{104}$, —$CHR_{104}R_{104}$ and —$CR_{104}R_{104}R_{104}$;

each $R_{104}$ is independently selected from CN, —$NO_2$ and halogen;

$W_1$ is selected from —$R_{105}$, —$OR_{105}$, —$SR_{105}$ and —$NR_{105}R_{105}$;

each $R_{105}$ is independently selected from hydrogen, (C1-C6) alkyl, (C2-C6) alkenyl or (C2-C6) alkynyl optionally substituted with one or more of the same or different R groups, (C5-C14) aryl optionally substituted with one or more of the same or different R groups, phenyl optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

$A_1$ is selected from (C1-C6) alkylene optionally substituted with 1, 2, 3, 4, 5 or 6 of the same or different halogen atoms, —$(CH_2)_m$—O—$CH_2$— and —$(CH_2)_m$—S—$CH_2$—, where m is an integer from 0 to 4;

$X_1$ is selected from —$(CH_2)_n$— and —$(CH_2)_n$—O—, where n is an integer from 0 to 6;

$Y_1$ is selected from hydrogen, (C1-C6) alkyl, (C2-C6) alkenyl, or (C2-C6) alkynyl, optionally substituted with one or more of the same or different $R_{100}$ groups, (C5-C14) aryl optionally substituted with one or more of the same or different $R_{100}$ groups, phenyl, optionally substituted with one or more of the same or different $R_{100}$ groups, (C6-C16) arylalkyl optionally substituted with one or more of the same or different $R_{100}$ groups, 5-14 membered heteroaryl optionally substituted with one or more of the same or different $R_{100}$ groups, 6-16 membered heteroarylalkyl optionally substituted with one or more of the same or different $R_{100}$ groups and a detectable label molecule;

each $R_{100}$ is independently selected from an electronegative group, =O, —$OR^{a1}$, (C1-C3) haloalkyloxy, =S, —$SR^{a1}$, =$NR^{a1}$, =$NONR^{a1}$, —$NR^{c1}R^{c1}$ halogen, —$CF_3$, —CN, —NC, —OCN, —SCN, —NO, —$NO_2$, =$N_2$, —$N_3$, —$S(O)R^{a1}$, —$S(O)_2R^{a1}$, —$S(O)_2OR^{a1}$, —$S(O)_2NR^{c1}R^{c1}$, —$OS(O)R^{a1}$, —$OS(O)_2R^{a1}$, —$OS(O)_2OR^{a1}$, —$OS(O)_2NR^{c1}R^{c1}$, —$C(O)R^{a1}$, —$C(O)OR^{a1}$, —$C(O)NR^{c1}R^{c1}$, —$OC(O)R^{a1}$, —$OC(O)OR^{a1}$, —$OC(O)NR^{c1}R^{c1}$, —$OC(NH)NR^{c1}R^{c1}$, —$NHC(O)R^{a1}$, —$NHC(O)OR^{a1}$, —$NHC(O)NR^{c1}R^{c1}$ and —$NHC(NH)NR^{c1}R^{c1}$;

each $R^{a1}$ is independently selected from hydrogen, (C1-C4) alkyl, (C2-C4) alkenyl or (C2-C4) alkynyl; and each $R^{c1}$ is independently an $R^{a1}$ or, alternatively, $R^{c1}R^{c1}$ taken together with the nitrogen atom to which it is bonded forms a 5 or 6 membered ring.

In certain embodiments of Formula 29, when $X_1$—$Y_1$ is —$CH_2CH_3$, then at least one of $R_{101}$, $R_{102}$ or $R_{103}$ is other than hydrogen.

In certain embodiments, a compound of Formula 29 is represented by Formula 30,

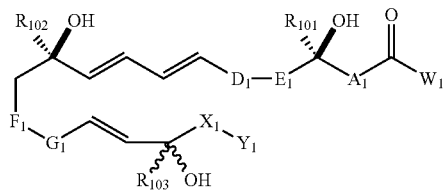
30 and pharmaceutically acceptable salts, hydrates and solvates thereof, wherein: $D_1$-$E_1$ and $F_1$-$G_1$ are independently are cis or trans —C=C— or —C≡C—; and $R_{101}$, $R_{102}$, $R_{103}$, $R_{104}$, $W_1$, $R_{105}$, $A_1$, $X_1$, n, $Y_1$, $R_{100}$, $R^{a1}$, and $R^{c1}$ are as defined above.

Other compounds suitable for use as active agents include those of Formulae 31 to 37

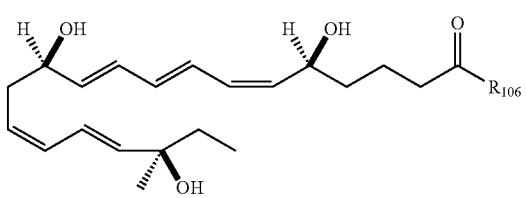
31

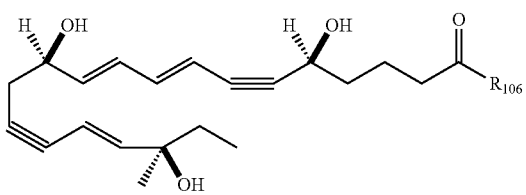
32

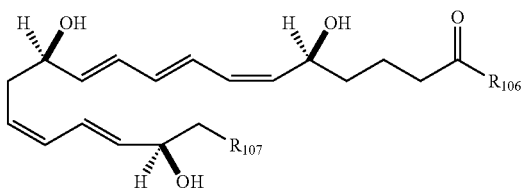
33

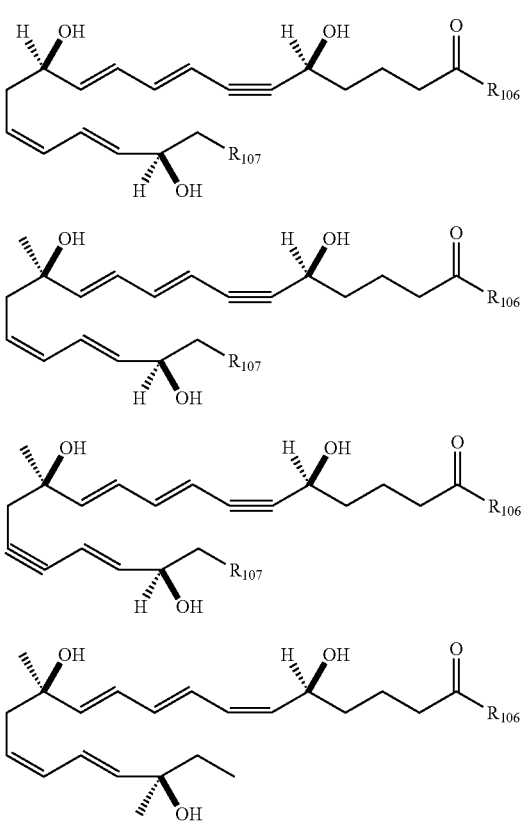

and pharmaceutically acceptable salts, hydrates and solvates thereof,
wherein:
$R_{106}$ is —OH, —OCH$_3$, —OCH(CH$_3$)$_2$ or —NHCH$_2$CH$_3$; and
$R_{107}$ is

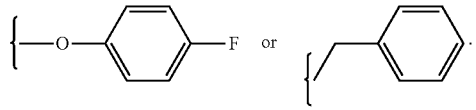

Other compounds suitable for use as active agents include those of Formula 38,

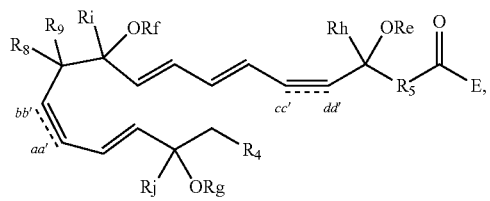

wherein:
Carbons aa' and bb' are connected by a double bond or a triple bond;
Carbons cc' and dd' are connected by a double bond or a triple bond;

Re, Rf, and Rg are independently selected from hydrogen, alkyl, alkenyl, alkynyl, aryl, heteroaryl, acyl (e.g., alkoxyacyl, aminoacyl), aminocarbonyl, alkoxycarbonyl, or silyl;

E is hydroxyl, alkoxy, aryloxy, amino, alkylamino, dialkylamino, or arylamino;

Rh, Ri and Rj are independently selected from hydrogen, alkyl, alkenyl, alkynyl, perfluoroalkyl, aryl or heteroaryl;

$R_4$ is selected from hydrogen, alkyl, perfluoroalkyl, alkenyl, alkynyl, aryl, heteroaryl, fluoro, hydroxyl, alkoxy, aryloxy;

$R_5$ is selected from i-iv as follows: i) CH$_2$CH(R$_6$)CH$_2$, where $R_6$ is hydrogen, alkyl, alkenyl, alkynyl, perfluoroalkyl, aryl, heteroaryl, fluoro, hydroxyl or alkoxy; ii) CH$_2$C(R$_6$R$_7$)CH$_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) CH$_2$OCH$_2$, CH$_2$C(O)CH$_2$, or CH$_2$CH$_2$; or iv) $R_5$ is a carbocyclic, heterocyclic, aryl or heteroaryl ring; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring;

or pharmaceutically acceptable salts thereof.

In certain embodiments $R_8$ and $R_9$ are hydrogen.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

Other compounds suitable for use as active agents include those of Formulae 39-44,

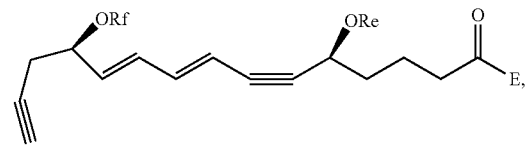

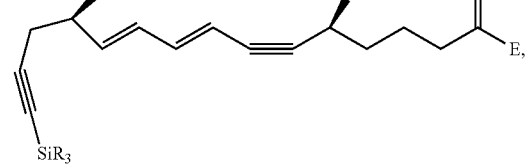

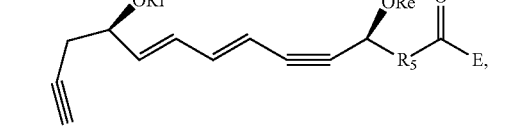

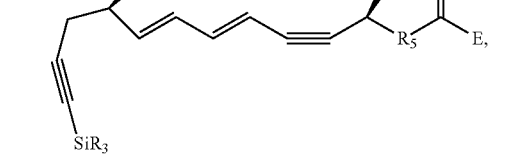

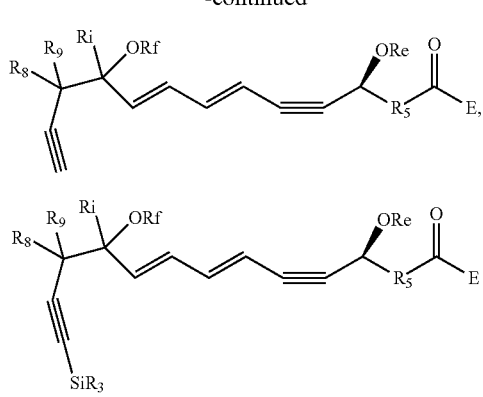

and pharmaceutically acceptable salts thereof, wherein:
Re, Rf, E, Ri, $R_5$, $R_8$ and $R_9$ are as defined above.

Exemplary compounds of formulae 39, 41, and 43 include:

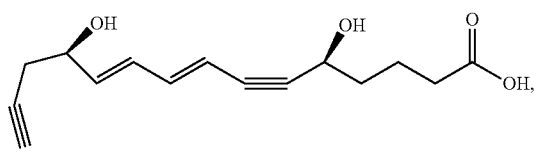

and pharmaceutically acceptable salts and esters thereof.

In certain embodiments, a pharmaceutically acceptable salt of the compound is formed by derivatizing E, wherein E is —OM, where M is a cation selected from ammonium, tetra-alkyl ammonium, Na, K, Mg, and Zn. Examples of such compounds include compound Z,

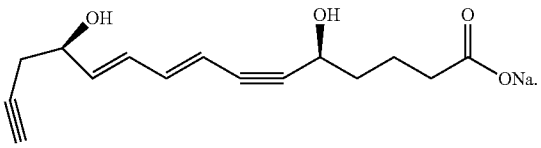

Other compounds suitable for use as active agents include those of Formula 46,

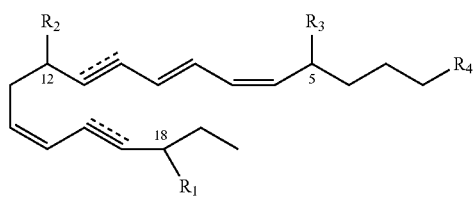

or a pharmaceutically acceptable salt or prodrug thereof, wherein:
each ═══ independently designates a double or triple bond;

$R^1$, $R^2$, and $R^3$ are each independently OR, $OX^1$, SR, $SX^2$, $N(R)_2$, $NHX^3$, NRC(O)R, $NRC(O)N(R)_2$, C(O)OR, $C(O)N(R)_2$, $SO_2R$, $NRSO_2R$, C(O)R, or $SO_2N(R)_2$;

each R is independently selected from hydrogen or an optionally substituted group selected from $C_{1-6}$ aliphatic, a 3-8 membered saturated, partially unsaturated, or aryl ring having 0-4 heteroatoms independently selected from nitrogen, oxygen, or sulfur, or;

two R on the same nitrogen are taken together with the nitrogen to form a 5-8 membered heterocyclyl or heteroaryl ring having 1-3 heteroatoms independently selected from nitrogen, oxygen, or sulfur;

each $X^1$ is independently a suitable hydroxyl protecting group;
each $X^2$ is independently a suitable thiol protecting group;
each $X^3$ is independently a suitable amino protecting group; and $R^4$ is NRC(O)R, $NRC(O)N(R)_2$, C(O)OR, $C(O)N(R)_2$, $SO_2R$, $NRSO_2R$, C(O)R, or $SO_2N(R)_2$.

Other compounds suitable for use as active agents include those of Formula 47,

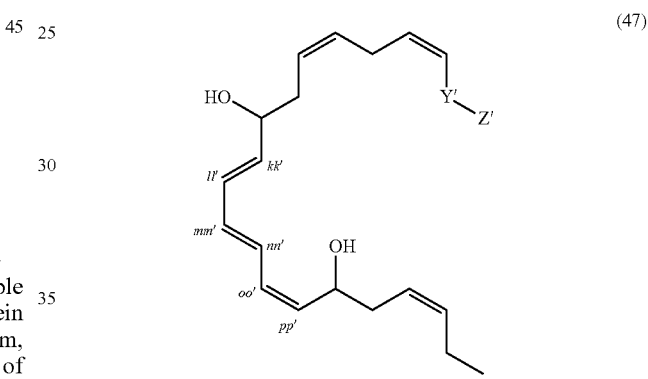

or a pharmaceutically acceptable salt or prodrug thereof, wherein:
the stereochemistry of the carbon kk' to carbon ll' double bond is cis or trans;
the stereochemistry of the carbon mm' to carbon nn' double bond is cis or trans;
the stereochemistry of the carbon oo' to carbon pp' double bond is cis or trans;
Y' is a bond or a linker selected from a ring containing up to 20 atoms or a chain of up to 20 atoms, provided that Y' can include one or more nitrogen, oxygen, sulfur or phosphorous atoms, further provided that Y' can include one or more substituents independently selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, or sulfonyl, further provided that Y' can contain one or more fused carbocyclic, heterocyclic, aryl or heteroaryl rings;
Z' is selected from —CN, —C(NH)N(R")(R"), —C(S)-A', —C(S)R", —C(O)-A', —C(O)—R", —C(O)—SR", —C(O)—NH—S(O)$_2$—R", —S(O)$_2$-A', —S(O)$_2$—R", S(O)$_2$N(R")(R"), —P(O)$_2$-A', —PO(OR")-A', -tetrazole, alkyltetrazole, or —CH$_2$OH, wherein
A' is selected from —OR", —N(R")(R") or —OM';
each R" is independently selected from hydrogen, alkyl, aryl, arylalkyl, heteroaryl, heteroarylalkyl or a detectable label molecule, wherein any alkyl-, aryl- or heteroaryl-containing moiety is optionally substituted with up to 3 independently selected substituents; and M' is a cation.

In certain embodiments, a compound of formula 47 is represented by formula 48,

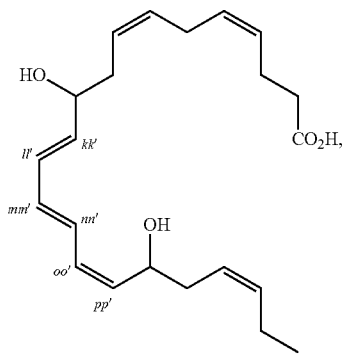

(48)

or pharmaceutically acceptable salts and esters thereof, wherein:

the stereochemistry of the carbon kk' to carbon ll' double bond is cis or trans;

the stereochemistry of the carbon mm' to carbon nn' double bond is cis or trans;

the stereochemistry of the carbon oo' to carbon pp' double bond is cis or trans.

In certain embodiments, the stereochemistry of the carbon kk' to carbon ll' double bond is trans.

In certain embodiments, the stereochemistry of the carbon mm' to carbon nn' double bond trans.

In certain embodiments, the stereochemistry of the carbon oo' to carbon pp' double bond is cis.

In certain embodiments, the stereochemistry of the carbon kk' to carbon ll' double bond is trans, the stereochemistry of the carbon mm' to carbon nn' double bond trans, and the stereochemistry of the carbon oo' to carbon pp' double bond is cis.

In certain embodiments, a compound of formula 47 is represented by compound 48a,

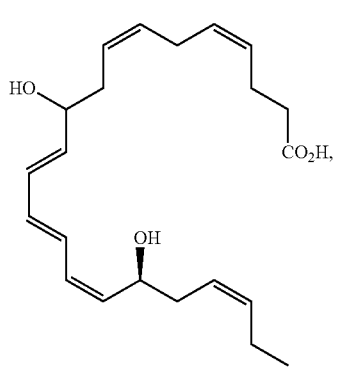

(48a)

compound 48b,

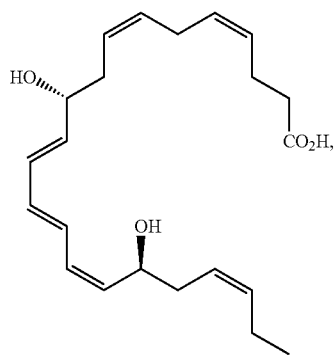

(48b)

compound 48c,

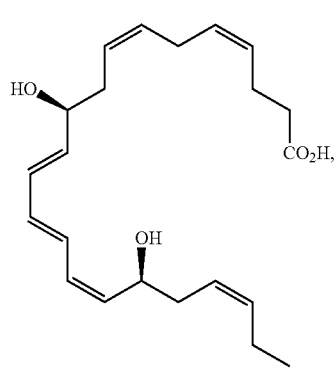

(48c)

or pharmaceutically acceptable salts and esters thereof.

In certain embodiments, a compound of formula 47 is represented by formula 48d,

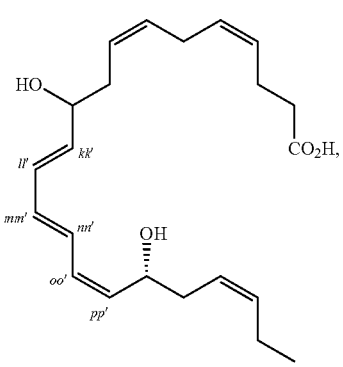

(48d)

or pharmaceutically acceptable salts and esters thereof, wherein:

the stereochemistry of the carbon kk' to carbon ll' double bond is cis or trans;

the stereochemistry of the carbon mm' to carbon nn' double bond is cis or trans;

the stereochemistry of the carbon oo' to carbon pp' double bond is cis or trans.

In certain embodiments, the compound of formula 47 is other than a compound of formula 48, 48a, 48b, 48c, or 48d.

Other compounds suitable for use as active agents include those of Formula 49, (49)

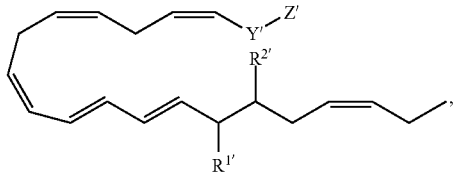

or a pharmaceutically acceptable salt or prodrug thereof, wherein:

Y' is a bond or a linker selected from a ring containing up to 20 atoms or a chain of up to 20 atoms, provided that Y' can include one or more nitrogen, oxygen, sulfur or phosphorous atoms, further provided that Y' can include one or more substituents independently selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, or sulfonyl, further provided that Y' can contain one or more fused carbocyclic, heterocyclic, aryl or heteroaryl rings;

Z' is selected from —CN, —C(NH)N(R")(R"), —C(S)-A', —C(S)R", —C(O)-A', —C(O)—R", —C(O)—SR", —C(O)—NH—S(O)$_2$—R", —S(O)$_2$-A', —S(O)$_2$—R", S(O)$_2$N(R")(R"), —P(O)$_2$-A', —PO(OR")-A', -tetrazole, alkyltetrazole, or —CH$_2$OH, wherein
A' is selected from —OR", —N(R")(R") or —OM';
each R" is independently selected from hydrogen, alkyl, aryl, arylalkyl, heteroaryl, heteroarylalkyl or a detectable label molecule, wherein any alkyl-, aryl- or heteroaryl-containing moiety is optionally substituted with up to 3 independently selected substituents; and
M' is a cation; and each of $R^{a'}$ and $R^{b'}$ is independently for each occurrence selected from —OR', or adjacent $R^{a'}$ and $R^{b'}$ are taken together to form an epoxide ring having a cis or trans configuration, wherein each R' is independently selected from hydrogen, alkyl, alkenyl, alkynyl, aryl, heteroaryl, acyl, silyl, alkoxyacyl, aminoacyl, aminocarbonyl, alkoxycarbonyl, or a protecting group.

Exemplary compounds of formula 49 include compound 49a, (49a)

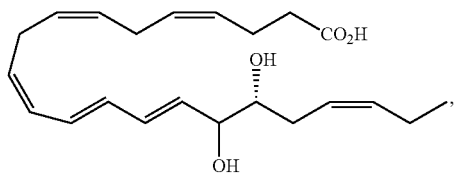

compound 49b, (49b)

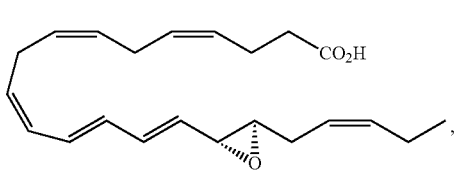

or pharmaceutically acceptable salts and esters thereof.

The compounds above (e.g., compounds of formula A or formulae 1 to 49) are known to be useful in the treatment or prevention of inflammation or inflammatory disease. Examples of such compounds are disclosed in the following patents and applications: US 2003/0191184, WO 2004/014835, WO 2004/078143, U.S. Pat. No. 6,670,396, US 2003/0236423, US 2005/0228047, US 2005/0238589 and US2005/0261255. These compounds are suitable for use in methods of the present invention.

Other compounds useful as active agents are compounds that are chemically similar variants to any of the compounds of formula A or formulae 1-49 set forth above. The term "chemically similar variants" includes, but is not limited to, replacement of various moieties with known biosteres; replacement of the end groups of one of the compounds above with a corresponding end group of any other compound above, modification of the orientation of any double bond in a compound, the replacement of any double bond with a triple bond in any compound, and the replacement of one or more substituents present in one of the compounds above with a corresponding substituent of any other compound.

Lipoxin compounds suitable for use as active agents include those of formula 50:

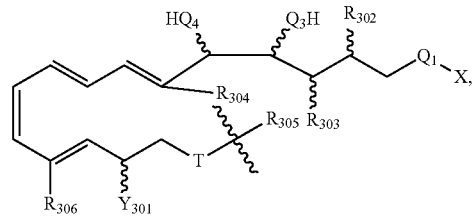

wherein:
X is $R_{301}$, $OR_{301}$, or $SR_{301}$;
$R_{301}$ is
(a) a hydrogen atom;
(b) an alkyl of 1 to 8 carbons atoms, inclusive, which may be straight chain or branched;
(c) a cycloalkyl of 3 to 10 carbon atoms;
(d) an aralkyl of 7 to 12 carbon atoms;
(e) phenyl;
(f) substituted phenyl

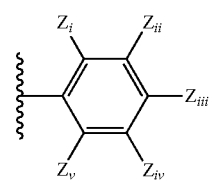

wherein $Z_i$, $Z_{ii}$, $Z_{iii}$, $Z_{iv}$, and $Z_v$ are each independently selected from —NO$_2$, —CN, —C(=O)—R$_{301}$, —SO$_3$H, a hydrogen atom, halogen, methyl, —OR$_x$, wherein R$_x$ is 1 to 8 carbon atoms, inclusive, which may be a straight chain or branched, and hydroxyl, wherein when any of $Z_i$, $Z_{ii}$, $Z_{iii}$, $Z_{iv}$ or $Z_v$ is C(=O)—R$_{301}$, said $Z_i$, $Z_{ii}$, $Z_{iii}$, $Z_{iv}$ or $Z_v$ is not substituted with another C(=O)—R$_{301}$.

(g) a detectable label molecule; or
(h) a straight or branched chain alkenyl of 2 to 8 carbon atoms, inclusive;

$Q_1$ is (C=O), $SO_2$ or (CN), provided when $Q_1$ is CN, then X is absent;

$Q_3$ and $Q_4$ are each independently O, S or NH;

one of $R_{302}$ and $R_{303}$ is a hydrogen atom and the other is:
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_kQ_2R_1$ wherein $Q_2$ is —O— or —S—; wherein $R_k$ is alkylene of 0 to 6 carbons atoms, inclusive, which may be straight chain or branched and wherein $R_1$ is alkyl of 0 to 8 carbon atoms, inclusive, which may be straight chain or branched, provided when $R_1$ is 0, then $R_1$ is a hydrogen atom;

$R_{304}$ is
(a) H;
(b) an alkyl of 1 to 6 carbon atoms, inclusive, which may be a straight chain or branched;

$R_{305}$ is

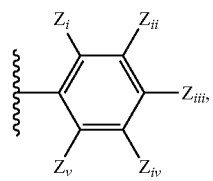

wherein $Z_i$, $Z_{ii}$, $Z_{iii}$, $Z_{iv}$ and $Z_v$ are defined as above;

$R_{306}$ is
(a) H;
(b) an alkyl from 1 to 4 carbon atoms, inclusive, straight chain or branched;

wherein $Y_{301}$ is —OH, methyl, —SH, an alkyl of 2 to 4 carbon atoms, inclusive, straight chain or branched, an alkoxy of 1 to 4 carbon atoms, inclusive, or $(CH)_p(Z)_q$, where p+q=3, p=0 to 3, q=0 to 3 and Z is cyano, nitro or a halogen; and T is O or S, and pharmaceutically acceptable salts thereof.

Lipoxin compounds suitable for use as active agents include those of formulae 51, 52, 53 or 54:

(51)
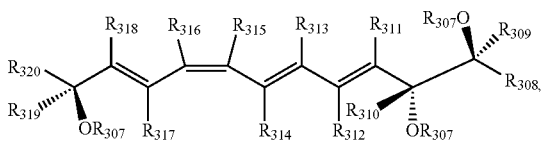

(52)
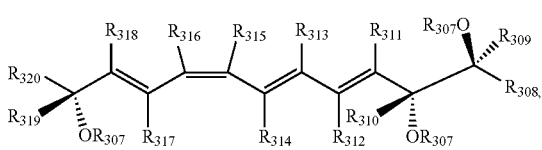

(53)
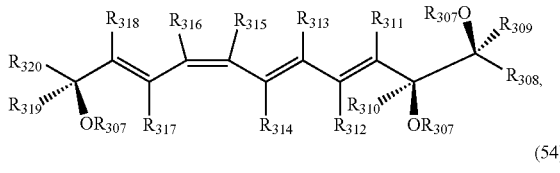

(54)
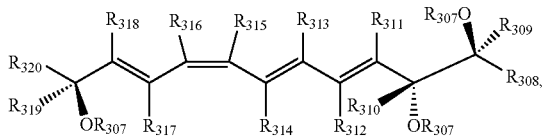

wherein:

each $R_{307}$ is independently selected from hydrogen and straight, branched, cyclic, saturated, or unsaturated alkyl having from 1 to 20 carbon atoms;

$R_{308}$, $R_{309}$, $R_{310}$, $R_{319}$, and $R_{320}$ are independently selected from:
(a) hydrogen;
(b) straight, branched, cyclic, saturated, or unsaturated alkyl having from 1 to 20 carbon atoms;
(c) substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;
(d) substituted aryl or heteroaryl, wherein the aryl or heteroaryl is substituted with one or more substituents selected from alkyl, cycloalkyl, alkoxy, halo, aryl, heteroaryl, carboxyl, and carboxamido; and
(e) Z—Y, wherein:
Z is selected from a straight, branched, cyclic, saturated, or unsaturated alkyl having from 1 to 20 carbon atoms; substituted lower alkyl, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; and substituted aryl or heteroaryl, wherein the aryl or heteroaryl is substituted with one or more substituents selected from alkyl, cycloalkyl, alkoxy, halo, aryl, heteroaryl, carboxyl, and carboxamido; and
Y is selected from hydrogen; alkyl; cycloalkyl; carboxyl; carboxamido; aryl; heteroaryl; substituted aryl or heteroaryl, wherein the aryl or heteroaryl is substituted with one or more substituents selected from alkyl, cycloalkyl, alkoxy, halo, aryl, heteroaryl, carboxyl, and carboxamido; and $R_{311}$ to $R_{318}$ are independently selected from:
(a) hydrogen;
(b) halo;
(c) straight, branched, cyclic, saturated, or unsaturated alkyl having from 1 to 20 carbon atoms;
(d) substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;
(e) substituted aryl or heteroaryl, wherein the aryl or heteroaryl is substituted with one or more substituents selected from alkyl, cycloalkyl, alkoxy, halo, aryl, heteroaryl, carboxyl, and carboxamido; or $R_{308}$ to $R_{320}$ are independently a bond that forms a carbon-carbon double bond, a carbon-carbon triple bond, or a ring with the lipoxin backbone; or any two of $R_{307}$ to $R_{320}$ are taken together with the atoms to which they are bound and optionally to 1 to 6 oxygen atoms, 1 to 6 nitrogen atoms, or both 1 to 6 oxygen atoms and 1 to 6 nitrogen atoms, to form a ring containing 3 to 20 atoms.

Lipoxin compounds suitable for use as active agents include those of formula 55:

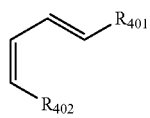

wherein:
$R_{401}$ is selected from:

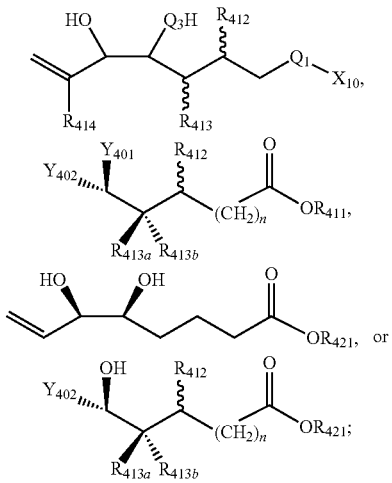

$R_{402}$ is selected from:

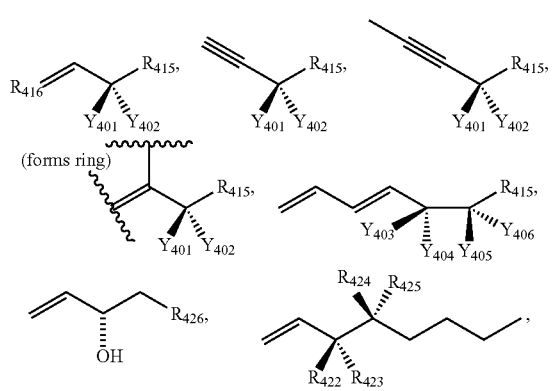

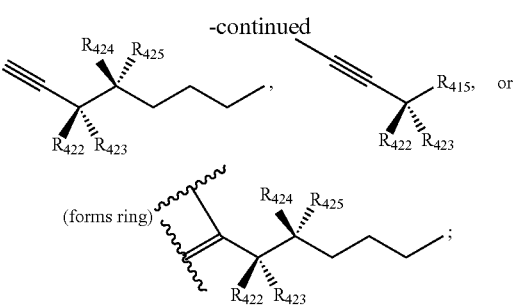

$X_{10}$ is $R_{411}$, $OR_{411}$, or $SR_{411}$;
$R_{411}$ is
(a) a hydrogen atom;
(b) an alkyl of 1 to 8 carbons atoms, inclusive, which may be straight chain or branched;
(c) a cycloalkyl of 3 to 10 carbon atoms;
(d) an aralkyl of 7 to 12 carbon atoms;
(e) phenyl;
(f) substituted phenyl

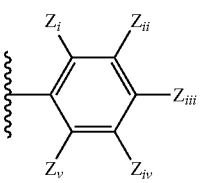

wherein $Z_i$, $Z_{ii}$, $Z_{iii}$, $Z_{iv}$ and $Z_v$ are each independently selected from —$NO_2$, —CN, —C(=O)—$R_{411}$, —$SO_3H$, a hydrogen atom, halogen, methyl, —$OR_x$, wherein $R_x$ is 1 to 8 carbon atoms, inclusive, which may be a straight chain or branched, and hydroxyl; wherein when any of $Z_i$, $Z_{ii}$, $Z_{iii}$, $Z_{iv}$ or $Z_v$ is C(=O)—$R_{411}$, said $Z_i$, $Z_{ii}$, $Z_{iii}$, $Z_{iv}$ or $Z_v$ is not substituted with another C(=O)—$R_{411}$.
(g) a detectable label molecule; or
(h) a straight or branched chain alkenyl of 2 to 8 carbon atoms, inclusive;
$Q_1$ is (C=O), $SO_2$ or (CN);
$Q_3$ is O, S or NH;
one of $R_{412}$ and $R_{413}$ is a hydrogen atom and the other is selected from:
(a) H;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_{431}Q_2R_{432}$ wherein $Q_2$ is —O— or —S—; wherein $R_{431}$ is alkylene of 0 to 6 carbons atoms, inclusive, which can be straight chain or branched and wherein $R_{431}$ is alkyl of 0 to 8 carbon atoms, inclusive, which can be straight chain or branched;
$R_{413a}$ and $R_{413b}$ are each independently:
(a) H;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_{431}Q_2R_{432}$ wherein $R_{431}$, $Q_2$, and $R_{432}$ are as defined above;

$R_{414}$ is
(a) H;
(b) an alkyl of 1 to 6 carbon atoms, inclusive, can be straight chain or branched;

$R_{415}$ is
(a) an alkyl of 1 to 9 carbon atoms which can be straight chain or branched;
(b) —(CH$_2$)—R$_i$,
wherein n=0 to 4 and R$_i$ is
(i) a cycloalkyl of 3 to 10 carbon atoms, inclusive;
(ii) a phenyl; or
(iii) substituted phenyl

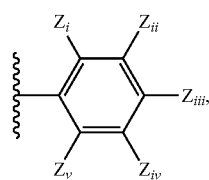

wherein $Z_i$ through $Z_v$ are as defined above;
(c) $R_{431}Q_2R_{432}$, wherein $R_{431}$, $Q_2$, and $R_{432}$ are as defined above;
(d) —C(R$_{iii}$)(R$_{iv}$)—R$_i$,
wherein R$_{iii}$ and R$_{iv}$ are each independently:
(i) a hydrogen atom;
(ii) (CH)$_p$(Z)$_q$, wherein Z, p, and q are as defined above;
(e) a haloalkyl of 1 to 8 carbon atoms, inclusive, and 1 to 6 halogen atoms, inclusive, straight chain or branched;

$R_{416}$ is
(a) H;
(b) an alkyl from 1 to 4 carbon atoms, inclusive, straight chain or branched;
(c) a halogen;

one of $Y_{401}$ or $Y_{402}$ is —OH, methyl, or —SH, and wherein the other is selected from:
(a) H;
(b) (CH)$_p$(Z)$_q$ where p+q=3, p=0 to 3, q=0 to 3 and each Z, independently, is cyano, nitro or a halogen;
(c) an alkyl of 2 to 4 carbon atoms, inclusive, straight chain or branched; or
(d) an alkoxy of 1 to 4 carbon atoms, inclusive,
or $Y_{401}$ and $Y_{402}$ taken together are:
(a) =NH; or
(b) =O;

one of $Y_{403}$ or $Y_{404}$ is —OH, methyl, or —SH, and wherein the other is selected from:
(a) H;
(b) (CH)$_p$(Z)$_q$ wherein Z, p, and q are as defined above;
(c) an alkyl of 2 to 4 carbon atoms, inclusive, straight chain or branched; or
(d) an alkoxy of 1 to 4 carbon atoms, inclusive,
or $Y_{401}$ and $Y_{402}$ taken together are:
(a) =NH; or
(b) =O;

one of $Y_{405}$ or $Y_{406}$ is —OH, methyl, or —SH, and wherein the other is selected from:
(a)
(b) (CH)$_p$(Z)$_q$ wherein Z, p, and q are as defined above;
(c) an alkyl of 2 to 4 carbon atoms, inclusive, straight chain or branched; or
(d) an alkoxy of 1 to 4 carbon atoms, inclusive, or $Y_{401}$ and $Y_{402}$ taken together are:
(a) =NH; or
(b) =O;

$R_{421}$ is
(a) H; or
(b) alkyl of 1 to 8 carbon atoms;

$R_{422}$ and $R_{423}$ are each independently:
(a) H;
(b) a hydroxyl, or a thiol;
(c) a methyl or a halomethyl;
(d) a halogen; or
(e) an alkoxy of 1 to 3 carbon atoms;

$R_{424}$ and $R_{425}$ are each independently:
(a) H;
(b) a hydroxyl, or a thiol;
(c) a methyl or a halomethyl;
(d) a halogen;
(e) an alkoxy of 1 to 3 carbon atoms; or
(f) an alkyl or haloalkyl of 2 to 4 carbon atoms inclusive, which can be straight chain or branched; and $R_{426}$ is
(a) a substituted phenyl

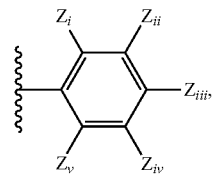

wherein $Z_i$ through $Z_v$ are as defined above;
(b) a substituted phenoxy

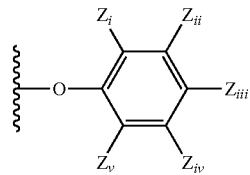

wherein $Z_i$ through $Z_v$ are as defined above; or
(c)

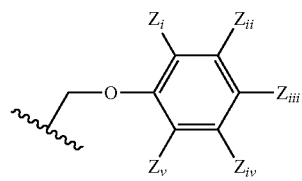

wherein $Z_i$ through $Z_v$ are as defined above.

Lipoxin compounds suitable for use as active agents include those of formula 56:

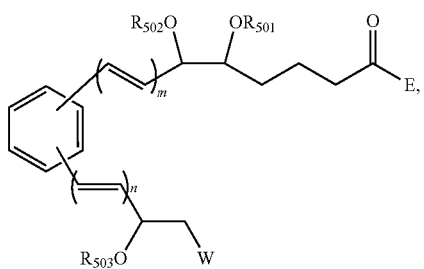
(56)

wherein:

E is hydroxy, alkoxy, aryloxy, amino, alkylamino, dialkylamino or —OM, where M is a cation selected from ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

each of $R_{501}$-$R_{503}$ are independently selected from hydrogen, alkyl, aryl, acyl or alkoxyacyl;

n is 0, 1 or 2;

m is 1 or 2; and the two substituents on the phenyl ring are ortho, meta, or para.

Lipoxin compounds suitable for use as active agents include those of formula 57:

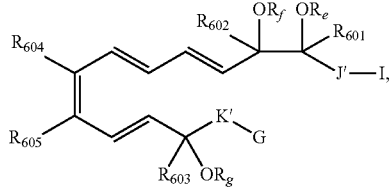
(57)

wherein:

I is selected from: —C(O)-E, —SO$_2$-E, —PO(OR)-E, where E is hydroxy, alkoxy, aryloxy, amino, alkylamino, dialkylamino, or —OM, where M is a cation selected from ammonium, tetra-alkyl ammonium, Na, K, Mg, and Zn; and R is hydroxyl or alkoxy J' and K' are linkers independently selected from a chain of up to 20 atoms and a ring containing up to 20 atoms, provided that J' and K' can independently include one or more nitrogen, oxygen, sulfur or phosphorous atoms, and further provided that J' and K' can independently include one or more substituents selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that J' and K' can also contain one or more fused carbocyclic, heterocyclic, aryl or heteroaryl rings, and provided that linkers J' and K' are connected to the adjacent C(R)OR group via a carbon atom or a C-heteroatom bond where the heteroatom is oxygen, sulfur, phosphorous or nitrogen;

G is selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

Re, Rf and Rg, are independently selected from hydrogen, alkyl, aryl, heteroaryl, acyl, silyl, alkoxyacyl and aminoacyl;

$R_{601}$, $R_{602}$ and $R_{603}$ are independently selected from hydrogen, alkyl, aryl and heteroaryl, provided that $R_{601}$, $R_{602}$ and $R_{603}$ can independently be connected to linkers J' or K';

$R_{604}$ and $R_{605}$ are independently selected from hydrogen, alkyl, alkenyl, alkynyl, aryl, heteroaryl, fluoro, and provided that $R_{604}$ and $R_{605}$ can be joined together to form a carbocyclic, heterocyclic or aromatic ring, and further provided that $R_{604}$ and $R_{605}$ can be replaced by a bond to form a triple bond.

Other compounds suitable for use as active agents are the oxylipins described in international applications WO 2006055965, WO 2007090162, and WO2008103753 the compounds in which are incorporated herein by reference. Examples of such compounds are those of formulae 58-115, as shown in Table 1. These compounds include long chain omega-6 fatty acids, docosapentaenoic acid (DPAn-6) (compounds 58-73) and docosatetraenoic acid (DTAn-6) (compounds 74-83), and the omega-3 counterpart of DPAn-6, docosapentaenoic acid (DPAn-3) (compounds 84-97). Further compounds are the docosanoids 98-115, the α-linolenic acids (GLA) (compounds 116-122), and the stearidonic acids (SDA) (compounds 123-132).

TABLE 1

10,17-Dihydroxy DPAn-6 (58)

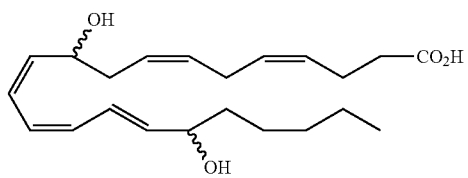 [SMILES: CCCCCC(O)/C=C/C=C\C=C/C(O)C/C=C\C/C=C\CCC(=O)O]

16,17-Dihydroxy DPAn-6 (59)

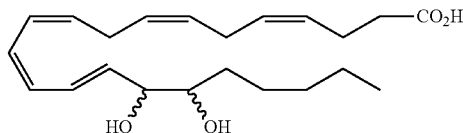 [SMILES: CCCCCC(O)C(O)/C=C/C=C\C=C/C/C=C\C/C=C\CCC(=O)O]

TABLE 1-continued
| | |
|---|---|
| 4,5-Dihydroxy DPAn-6 (60) | 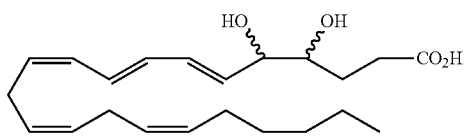 [SMILES: CCCCC/C=C\C/C=C\C\C=C/C=C/C=C/C(O)C(O)CCC(=O)O] |
| 7,17-Dihydroxy DPAn-6 (61) | 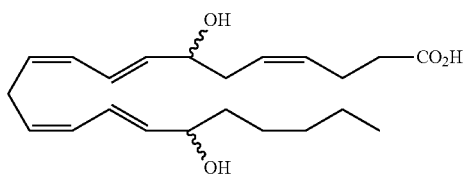 [SMILES: CCCCCC(O)/C=C/C=C\C/C=C\C=C\C(O)C/C=C\CCC(=O)O] |
| 7-Hydroxy DPAn-6 (62) | 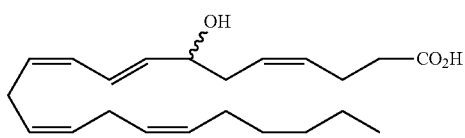 |
| 10-hydroxy DPAn-6 (63) | 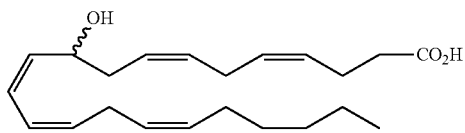 [SMILES: CCCCC/C=C\C/C=C\C=C/C(O)C/C=C\C/C=C\CCC(=O)O] |
| 13-Hydroxy DPAn-6 (64) | 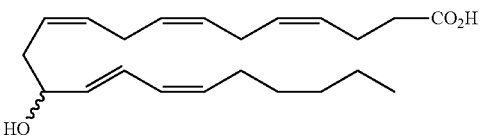 [SMILES: CCCCC/C=C\C=C\C(O)C/C=C\C/C=C\C/C=C\CCC(=O)O] |
| 17-hydroxy DPAn-6 (65) | 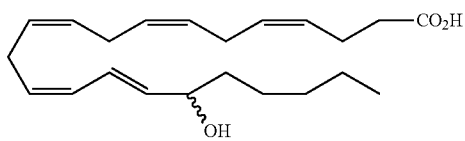 [SMILES: CCCCCC(O)/C=C/C=C\C/C=C\C/C=C\C/C=C\CCC(=O)O] |
| 4,5,17-Trihydroxy DPAn-6 (66) | 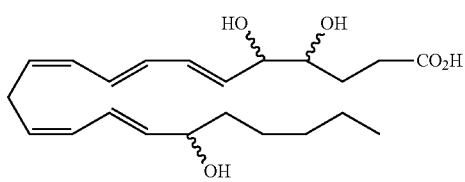 [SMILES: CCCCCC(O)/C=C/C=C\C\C=C/C=C/C=C/C(O)C(O)CCC(=O)O] |
| 7,16,17-Trihydroxy DPAn-6 (67) | 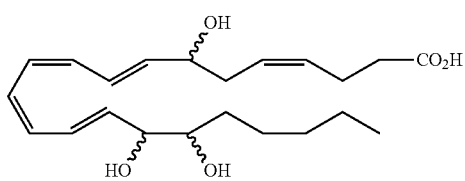 [SMILES: CCCCCC(O)C(O)/C=C/C=C\C=C/C=C/C(O)C/C=C\CCC(=O)O] |
| 8-Hydroxy DPAn-6 (68) | 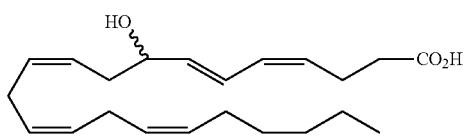 |
| 14-Hydroxy DPAn-6 (69) | 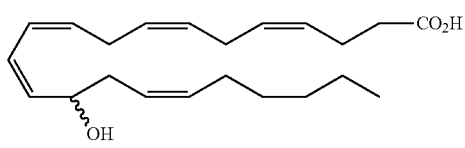 [SMILES: CCCCC/C=C\CC(O)/C=C\C=C/C/C=C\C/C=C\CCC(=O)O] |

TABLE 1-continued
13,17-Dihydroxy DPAn-6 (70)
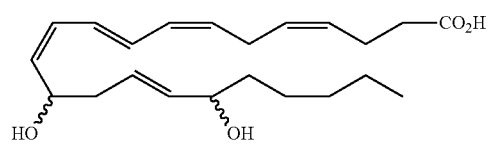 [SMILES: CCCCCC(O)/C=C/CC(O)\C=C/C=C/C=C\C/C=C\CCC(=O)O]
7,14-Dihydroxy DPAn-6 (71)
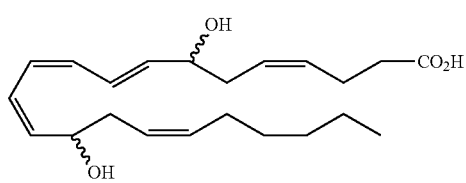 [SMILES: CCCCC/C=C\CC(O)\C=C/C=C\C=C\C(O)C/C=C\CCC(=O)O]
8,14-Dihydroxy DPAn-6 (72)
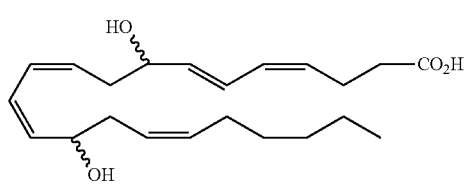 [SMILES: CCCCC/C=C\CC(O)/C=C\C=C/CC(O)/C=C/C=C\CCC(=O)O]
11-Hydroxy DPAn-6 (73)
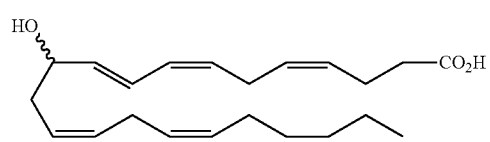
10,17-Dihydroxy-DTAn-6 (74)
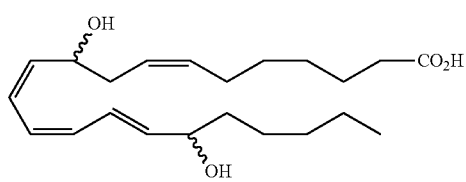 [SMILES: CCCCCC(O)/C=C/C=C\C=C/C(O)C/C=C\CCCCCC(=O)O]
16,17-Dihydroxy-DTAn-6 (75)
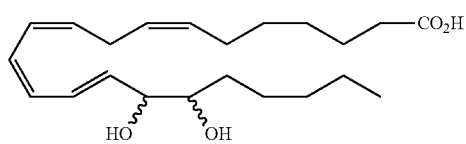 [SMILES: CCCCCC(O)C(O)/C=C/C=C\C=C/C/C=C\CCCCCC(=O)O]
4,5-Dihydroxy-DTAn-6 (76)
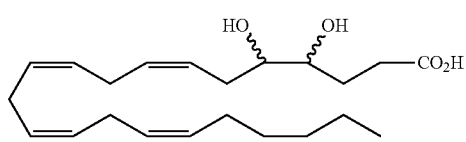
7,17-Dihydroxy-DTAn-6 (77)
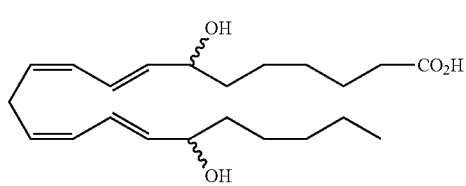 [SMILES: CCCCCC(O)/C=C/C=C\C/C=C\C=C\C(O)CCCCCC(=O)O]
7-Hydroxy-DTAn-6 (78)
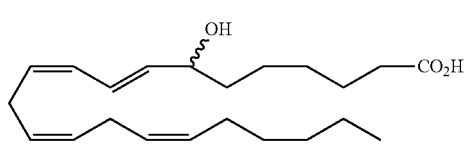 [SMILES: CCCCC/C=C\C/C=C\C/C=C\C=C\C(O)CCCCCC(=O)O]

TABLE 1-continued
10-Hydroxy-DTAn-6 (79)  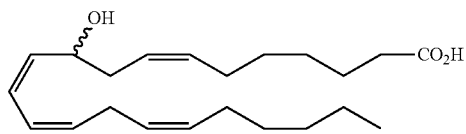 [SMILES: CCCCC/C=C\C/C=C\C=C/C(O)C/C=C\CCCCCC(=O)O]
13-Hydroxy-DTAn-6 (80)  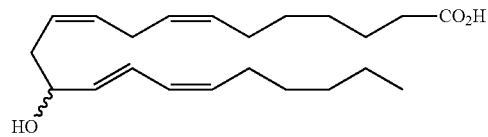 [SMILES: CCCCC/C=C\C=C\C(O)C/C=C\C/C=C\CCCCCC(=O)O]
17-Hydroxy-DTAn-6 (81)  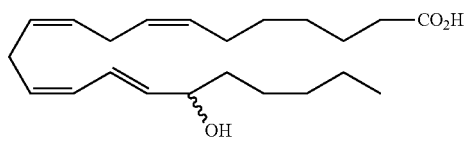 [SMILES: CCCCCC(O)/C=C/C=C\C/C=C\C/C=C\CCCCCC(=O)O]
4,5,17-Trihydroxy-DTAn-6 (82)  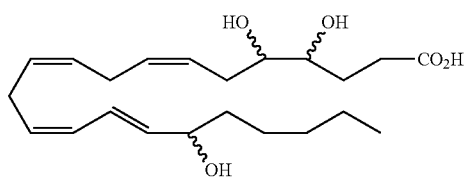 [SMILES: CCCCCC(O)/C=C/C=C\C/C=C\C/C=C\CC(O)C(O)CCC(=O)O]
7,16,17-Trihydroxy-DTAn-6 (83)  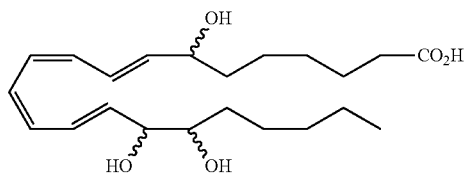 [SMILES: CCCCCC(O)C(O)/C=C/C=C\C=C/C=C/C(O)CCCCCC(=O)O]
10,17-Dihydroxy DPAn-3 (84)  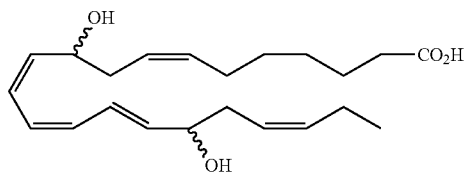 [SMILES: CC/C=C\CC(O)/C=C/C=C\C=C/C(O)C/C=C\CCCCCC(=O)O]
10,20-Dihydroxy DPAn-3 (85)  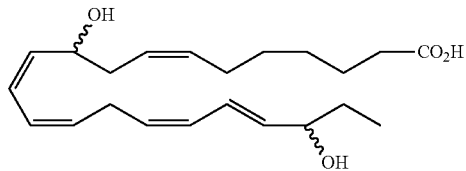 [SMILES: CCC(O)/C=C/C=C\C/C=C\C=C/C(O)C/C=C\CCCCCC(=O)O]
13,20-Dihydroxy DPAn-3 (86)  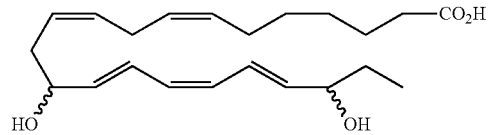 [SMILES: CCC(O)/C=C/C=C\C=C\C(O)C/C=C\C/C=C\CCCCCC(=O)O]
16,17-Dihydroxy DPAn-3 (87)  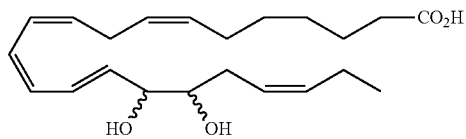 [SMILES: CC/C=C\CC(O)C(O)/C=C/C=C\C=C/C/C=C\CCCCCC(=O)O]

TABLE 1-continued
7,17-Dihydroxy DPAn-3 (88)
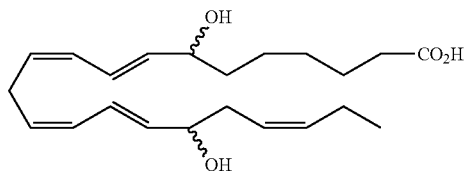 [SMILES: CC/C=C\CC(O)/C=C/C=C\C/C=C\C=C\C(O)CCCCCC(=O)O]
7-Hydroxy DPAn-3 (89)
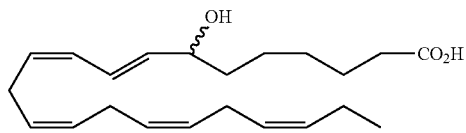
10-Hydroxy-DPAn-3 (90)
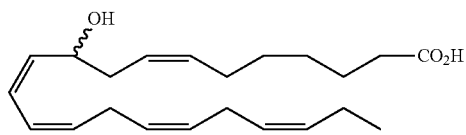
13-Hydroxy DPAn-3 (91)
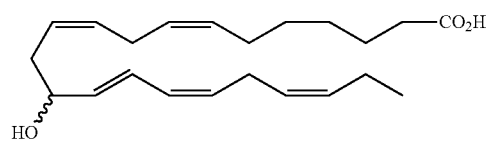 [SMILES: CC/C=C\C/C=C\C=C\C(O)C/C=C\C/C=C\CCCCCC(=O)O]
17-Hydroxy DPAn-3 (92)
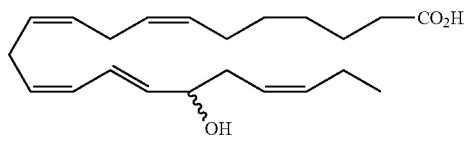 [SMILES: CC/C=C\CC(O)/C=C/C=C\C/C=C\C/C=C\CCCCCC(=O)O]
7,16,17-Trihydroxy DPAn-3 (93)
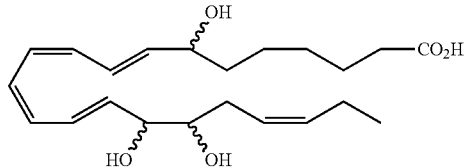 [SMILES: CC/C=C\CC(O)C(O)/C=C/C=C\C=C/C=C/C(O)CCCCCC(=O)O]
16-Hydroxy DPAn-3 (94)
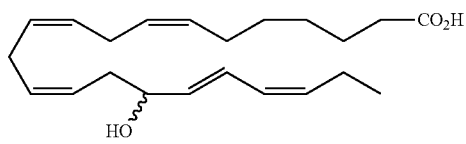 [SMILES: CC/C=C\C=C\C(O)C/C=C\C/C=C\C/C=C\CCCCCC(=O)O]
11-Hydroxy DPAn-3 (95)
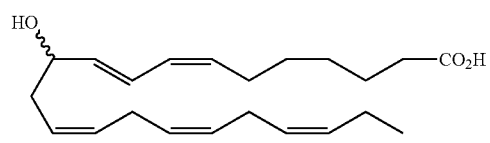 [SMILES: CC/C=C\C/C=C\C/C=C\CC(O)/C=C/C=C\CCCCCC(=O)O]
14-Hydroxy DPAn-3 (96)
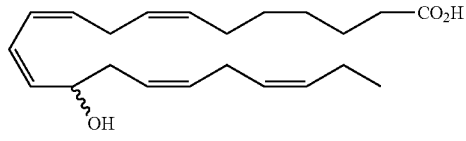 [SMILES: CC/C=C\C/C=C\CC(O)/C=C\C=C/C/C=C\CCCCCC(=O)O]
8,14-Dihydroxy DPAn-3 (97)
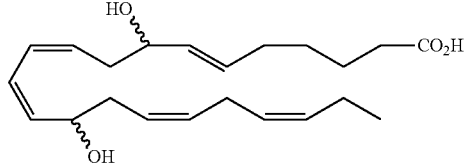 [SMILES: CC/C=C\C/C=C\CC(O)/C=C\C=C/CC(O)/C=C/CCCCC(=O)O]

TABLE 1-continued
10,11-Epoxy DHA (98) 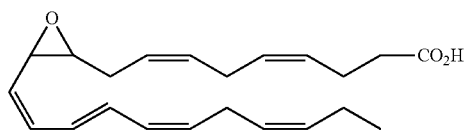 [SMILES: CC/C=C\C\C=C/C=C/C=C\C1OC1C/C=C\C/C=C\CCC(=O)O]
13,14-Dihydroxy DHA (99) 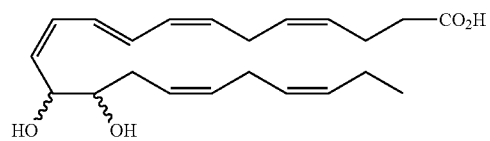 [SMILES: CC/C=C\C/C=C\CC(O)C(O)\C=C/C=C/C=C\C/C=C\CCC(=O)O]
13,14-Epoxy DHA (100) 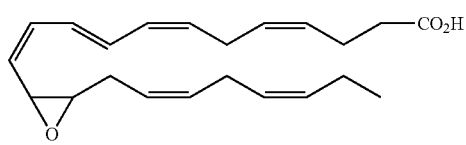 [SMILES: CC/C=C\C/C=C\CC1OC1\C=C/C=C/C=C\C/C=C\CCC(=O)O]
19,20-Epoxy DHA (101) 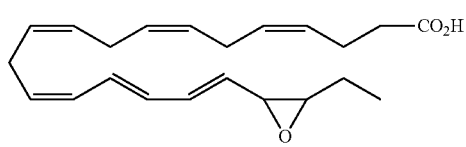 [SMILES: CCC1OC1/C=C/C=C/C=C\C/C=C\C/C=C\C/C=C\CCC(=O)O]
7,8-Epoxy DHA (102) 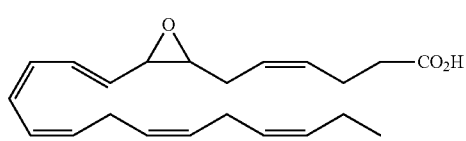
4,5-Epoxy-17-OH DPA (103) 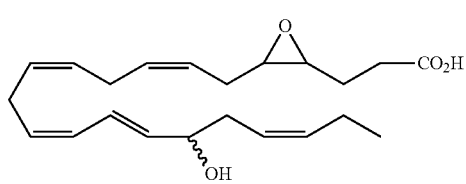 [SMILES: CC/C=C\CC(O)/C=C/C=C\C/C=C\C/C=C\CC1OC1CCC(=O)O]
7,16,17-Trihydroxy DTAn-3 (104) 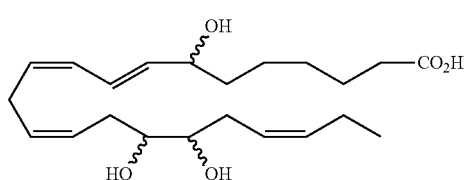 [SMILES: CC/C=C\CC(O)C(O)C/C=C\C/C=C\C=C\C(O)CCCCCC(=O)O]
16,17-Dihidroxy DTAn-3 (105) 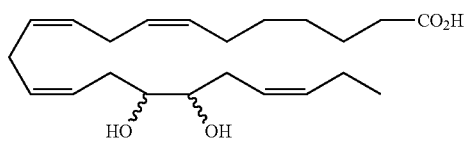 [SMILES: CC/C=C\CC(O)C(O)C/C=C\C/C=C\C/C=C\CCCCCC(=O)O]
10,16,17-Trihydroxy DTRAn-6 (106) 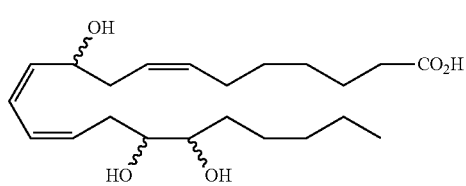 [SMILES: CCCCCC(O)C(O)C/C=C\C=C/C(O)C/C=C\CCCCCC(=O)O]

TABLE 1-continued
16,17-Dihydroxy DTRAn-6 (107)
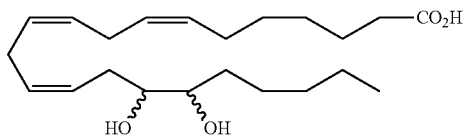 [SMILES: CCCCCC(O)C(O)C/C=C\C/C=C\C/C=C\CCCCCC(=O)O]
7,16,17-Trihydroxy DTRAn-6 (108)
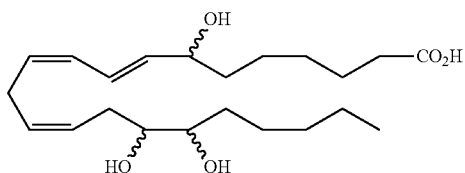 [SMILES: CCCCCC(O)C(O)C/C=C\C/C=C\C=C\C(O)CCCCCC(=O)O]
15-epi-lipoxin A4 (109)
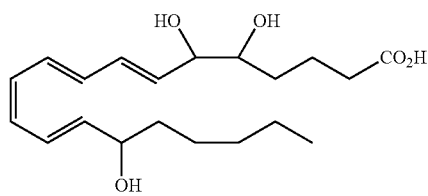 [SMILES: CCCCCC(O)/C=C/C=C\C=C\C=C\C(O)C(O)CCCC(=O)O]
16,17-epoxy DHA (110)
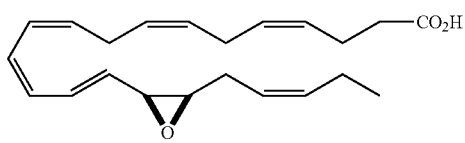
7,8-epoxy DPA (111)
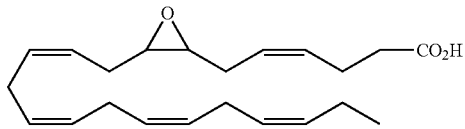 [SMILES: CC/C=C\C/C=C\C/C=C\C/C=C\CC1OC1C/C=C\CCC(=O)O]
10,11 epoxy DPA (112)
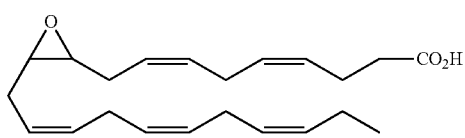
19,20 epoxy DPA (113)
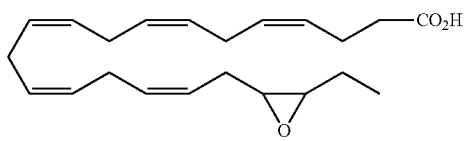 [SMILES: CCC1OC1C/C=C\C/C=C\C/C=C\C/C=C\C/C=C\CCC(=O)O]
7-hydroxy DHA (114)
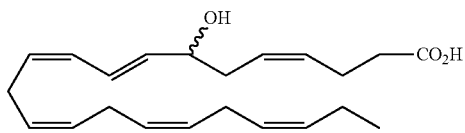 [SMILES: CC/C=C\C/C=C\C/C=C\C/C=C\C=C\C(O)C/C=C\CCC(=O)O]
13,14 epoxy DPA (115)
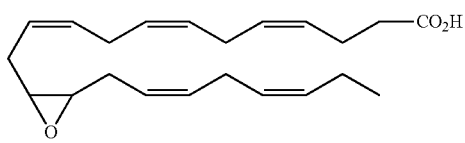 [SMILES: CC/C=C\C/C=C\CC1OC1C/C=C\C/C=C\C/C=C\CCC(=O)O]

TABLE 1-continued
6-hydroxy GLA (116) 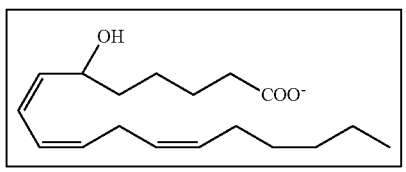
10-hydroxy GLA (117) 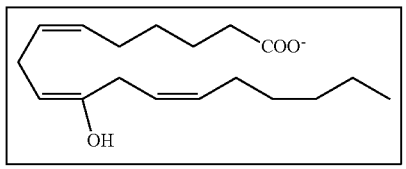
7-hydroxy GLA (118) 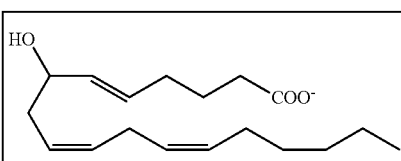
12-hydroxy GLA (119) 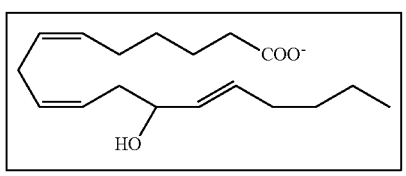
9-hydroxy GLA (120) 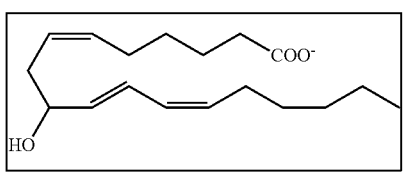
13-hydroxy GLA (121) 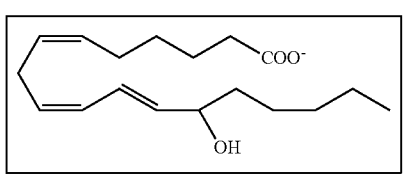
6,13 dihydroxy GLA (122) 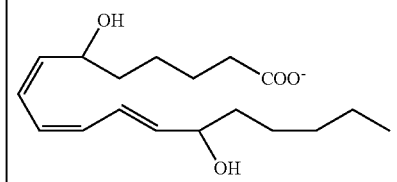
6-hydroxy SDA (123) 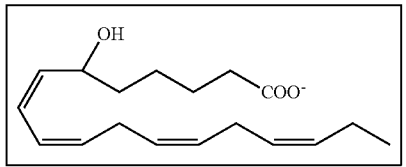

TABLE 1-continued
10-hydroxy SDA (124)
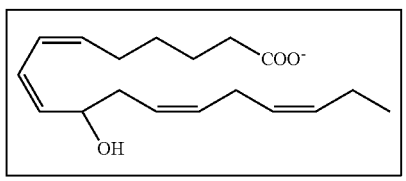
7-hydroxy SDA (125)
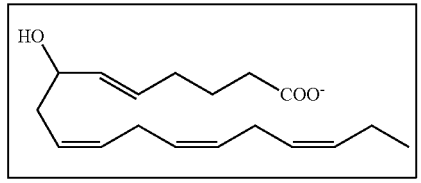
12-hydroxy SDA (126)
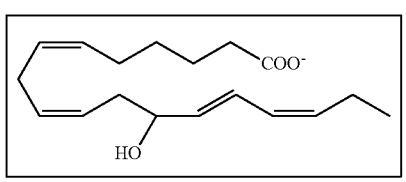
9-hydroxy SDA (127)
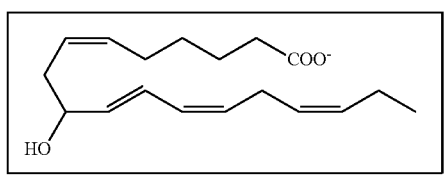
13-hydroxy SDA (128)
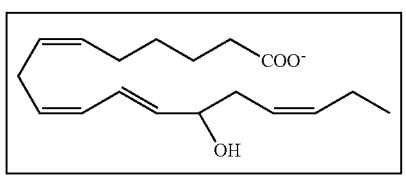
15-hydroxy SDA (129)
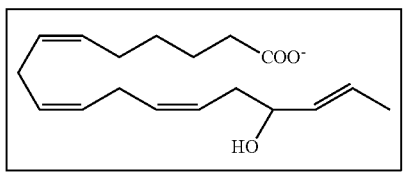
16-hydroxy SDA (130)
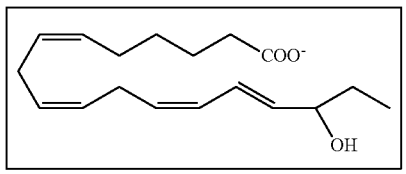
6,13 dihydroxy SDA (131)
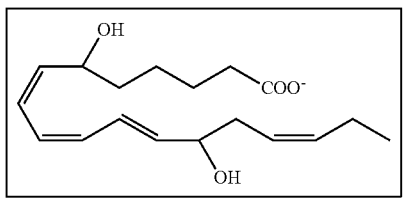

TABLE 1-continued 6,16 dihydroxy SDA (132)

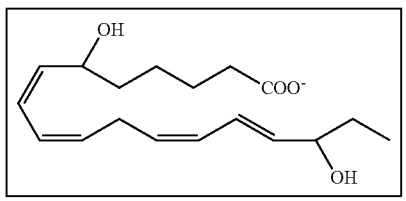

Other oxylipin compounds that are suitable for use as active agents include analogs of the compounds shown in Table 1. Such compounds include but are not limited to those analogs wherein one or more double bonds are replaced by triple bonds, those wherein one or more carboxy groups are derivatized to form esters, amides or salts, those wherein the hydroxyl-bearing carbons are further derivatized (with, for example, a substituted or unsubstituted, branched or unbranched alkyl, alkenyl, or alkynyl group, substituted or unsubstituted aryl group, substituted or unsubstituted, branched or unbranched alkylaryl group, halogen atom) to form tertiary alcohols (or ethers, esters, or other derivatives thereof), those wherein one or more hydroxyl groups are derivatized to form esters or protected alcohols, or those having combinations of any of the foregoing modifications.

Further oxylipin compounds suitable for use as active agents include the following: isolated docosanoids of docosapentaenoic acid (DPAn-6); monohydroxy, dihydroxy, and trihydroxy derivatives of DPAn-6; isolated docosanoids of docosapentaenoic acid (DPAn-3); monohydroxy, dihydroxy, and trihydroxy derivatives of DPAn-3; isolated docosanoids of docosapentaenoic acid (DTAn-6); or monohydroxy, dihydroxy, and trihydroxy derivatives of DTAn-6.

Other compounds suitable for use as active agents include compounds of formula I,

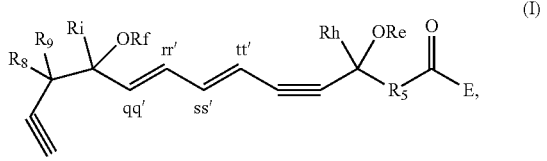

(I)

and pharmaceutically acceptable salts thereof, wherein:
the stereochemistry of the carbon qq' to carbon rr' double bond is cis or trans;
the stereochemistry of the carbon ss' to carbon tt' double bond is cis or trans;
Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl, preferably from hydrogen, acyl (e.g., alkoxyacyl, aminoacyl), aminocarbonyl, and alkoxycarbonyl, most preferably hydrogen;
E is a branched alkoxy such as isopropoxy, isobutoxyt, sec-butoxy, tert-butoxy, 3-methylbutoxy, 2,2-dimethylpropoxy, or 1,1,2-trimethylpropoxy, preferably isopropoxy;
Rh and Ri are independently selected from hydrogen, alkyl, alkenyl, alkynyl, perfluoroalkyl, aryl or heteroaryl, preferably hydrogen or alkyl, most preferably hydrogen;

$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, $CH_2$, or $CH_2CH_2$; or iv) $R_5$ is a carbocyclic, heterocyclic, aryl or heteroaryl ring, preferably $(CH_2)_3$; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring, preferably from hydrogen and alkyl, most preferably hydrogen.

For example, an active agent may be a compound of formula Ia,

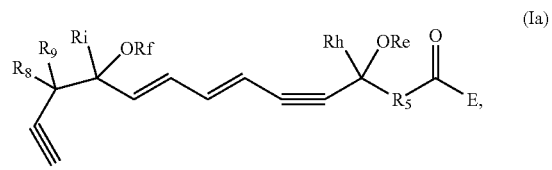

(Ia)

and pharmaceutically acceptable salts thereof, wherein:
Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl, preferably from hydrogen, acyl (e.g., alkoxyacyl, aminoacyl), aminocarbonyl, and alkoxycarbonyl, most preferably hydrogen;
E is a branched alkoxy such as isopropoxy, isobutoxyt, sec-butoxy, tert-butoxy, 3-methylbutoxy, 2,2-dimethylpropoxy, or 1,1,2-trimethylpropoxy, preferably isopropoxy;
Rh and Ri are independently selected from hydrogen, alkyl, alkenyl, alkynyl, perfluoroalkyl, aryl or heteroaryl, preferably hydrogen or alkyl, most preferably hydrogen;
$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, $CH_2$, or $CH_2CH_2$; or iv) $R_5$ is a carbocyclic, heterocyclic, aryl or heteroaryl ring, preferably $(CH_2)_3$; and
$R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring, preferably from hydrogen and alkyl, most preferably hydrogen.

In certain preferred embodiments of formula Ia, the stereochemistry of the carbons bearing —ORf and —ORe are as shown in formula Ia',

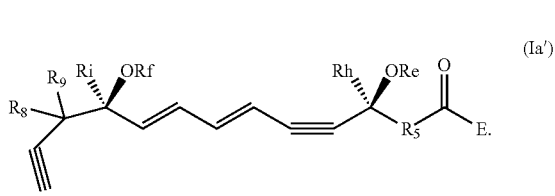

In certain embodiments, a compound of formula I is represented by formula II,

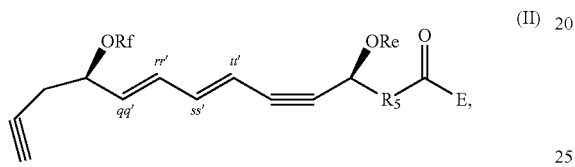

and pharmaceutically acceptable salts thereof, wherein:
the stereochemistry of the carbon qq' to carbon rr' double bond is cis or trans;
the stereochemistry of the carbon ss' to carbon tt' double bond is cis or trans;
Re, Rf, $R_5$, and E are as defined above.

For example, an active agent may be a compound of formula IIa,

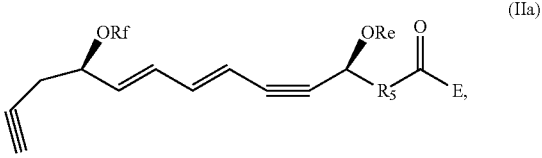

and pharmaceutically acceptable salts thereof, wherein:
Re, Rf, $R_5$, and E are as defined above.

In certain embodiments, a compound of formula I or II is represented by formula III,

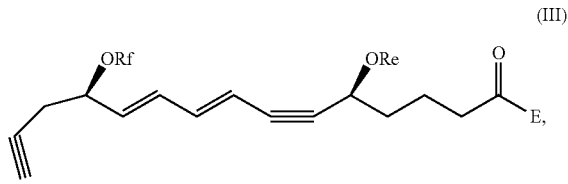

and pharmaceutically acceptable salts thereof, wherein:
Re, Rf, and E are as defined above.

In certain embodiments of Formulae I-III, E represents O—R, where R represents an alkyl group, preferably a lower alkyl group, that is branched at the position bonded to the oxygen atom. Exemplary such R moieties include —CH$(CH_3)_2$ (isopropyl), —CH$(CH_2CH_3)_2$, —CH$(CH_3)$$(CH_2CH_3)$ (sec-butyl), and —C$(CH_3)_3$ (tert-butyl).

Exemplary compounds of formulae I, II, and III include compound 1001

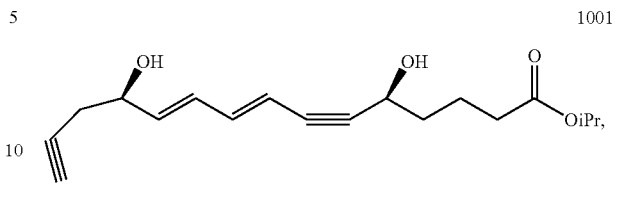

and pharmaceutically acceptable salts thereof.

In some embodiments an active agent may be a compound of formula IV,

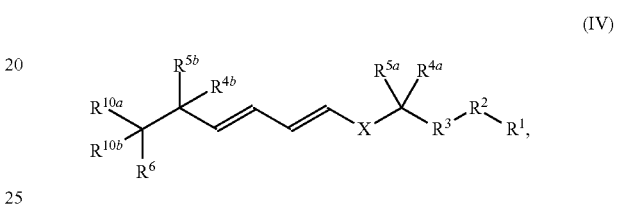

or a pharmaceutically acceptable salt thereof, wherein:
X is selected from —C≡C—, —C($R^7$)=C($R^7$)—, -(cyclopropyl)-, -(cyclobutyl)-, -(cyclopentyl)-, and -(cyclohexyl)-;
$R^1$ is selected from —O$R^a$, —N($R^a$)—SO$_2$—$R^c$ and —N($R^a$)($R^b$), wherein each of $R^a$ and $R^b$ is independently selected from H, $C_1$-$C_6$-alkyl, aryl, aralkyl, heteroaryl, and heteroaralkyl, and $R^c$ is selected from $C_1$-$C_6$-alkyl, aryl, aralkyl, heteroaryl, and heteroaralkyl;
$R^2$ is selected from —CH$_2$—, —C(O)—, —SO$_2$—, —PO(OR)—, and tetrazole;
R is selected from hydrogen and alkyl;
$R^3$ is selected from a carbocyclic ring, a heterocyclic ring, —(CH$_2$)$_n$—, CH$_2$C(O)CH$_2$, and —CH$_2$—O—CH$_2$, wherein:
n is an integer from 1 to 3;
any hydrogen atom in $R^3$ is optionally and independently replaced by halo, ($C_1$-$C_5$)-alkyl, perfluoroalkyl, aryl, heteroaryl, hydroxy, or O—($C_1$-$C_5$)-alkyl; and
any two hydrogen atoms bound to a common carbon atom in $R^3$ are optionally taken together with the carbon atom to which they are bound to form a carbocyclic or heterocyclic ring;
each of $R^{4a}$ and $R^{4b}$ is independently selected from hydrogen, halo, —OH, —O—($C_1$-$C_5$)-alkyl, —O-aryl, O-heteroaryl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro;
each of $R^{5a}$ and $R^{5b}$ is independently selected from hydrogen, halo, ($C_1$-$C_5$)-alkyl, perfluoroalkyl, aryl, and heteroaryl, preferably hydrogen, halo and ($C_1$-$C_5$)-alkyl;

R$^6$ is selected from -phenyl, —(C$_1$-C$_5$)-alkyl-, —(C$_3$-C$_7$)-cycloalkyl, —C≡C-phenyl, —C≡C—(C$_3$-C$_7$)-cycloalkyl, —C≡C—(C$_1$-C$_5$)-alkyl, and —O-phenyl, wherein phenyl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro, and R$^6$ is additionally selected from —C≡CH when:
a) X is —C(R$^7$)=C(R$^7$)— or -(cyclopropyl)-; or
b) each of R$^{4a}$ and R$^{4b}$ is hydrogen or halo; or
c) each of R$^{5a}$ and R$^{5b}$ is halo; or
d) R$^2$ is —CH$_2$—;
each R$^7$ is independently selected from hydrogen and (C$_1$-C$_5$)-alkyl, or two occurrences of R$^7$ may optionally be taken together with the carbons to which they are attached to form a 5- or 6-membered ring;
each of R$^{10a}$ and R$^{10b}$ is independently selected from hydrogen, (C$_1$-C$_5$)-alkyl, perfluoroalkyl, O—(C$_1$-C$_5$)-alkyl, aryl and heteroaryl, or
R$^{10a}$ and R$^{10b}$ are taken together with the carbon atom to which they are bound to form a carbocyclic or heterocyclic ring;
and each double bond is independently in an E- or a Z-configuration.

In certain embodiments, R$^1$ is —OM, where M is a cation selected from ammonium, tetra-alkyl ammonium, Na, K, Mg, and Zn.

In certain embodiments, R$^2$ and R$^1$ together are

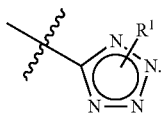

In certain embodiments, X is —C≡C—. In certain embodiments, X is —C(R$^7$)=C(R$^7$)—, -(cyclopropyl)-, -(cyclobutyl)-, -(cyclopentyl)-, or -(cyclohexyl)-. In certain embodiments, X is —C(R$^7$)=C(R$^7$)—. In certain embodiments, X is —C≡C—, -(cyclopropyl)-, -(cyclobutyl)-, -(cyclopentyl)-, or -(cyclohexyl)-. In certain embodiments, X is -(cyclopropyl)-. In certain embodiments, X is —C≡C— or —C(R$^7$)=C(R$^7$)—. In certain embodiments wherein X is -(cyclopropyl)-, -(cyclobutyl)-, -(cyclopentyl)-, or -(cyclohexyl)-, the olefin and the carbon bearing R$^{4a}$ are attached to adjacent carbons on the -(cyclopropyl)-, -(cyclobutyl)-, -(cyclopentyl)-, or -(cyclohexyl)-ring system.

In certain embodiments, R$^{4b}$ is hydrogen. In certain embodiments, R$^{4b}$ is halo, —OH, —O—(C$_1$-C$_5$)-alkyl, —O-aryl, O-heteroaryl, —O—C(O)—(C$_1$-C$_5$)-alkyl, —O—C(O)-aryl, —O—C(O)-heteroaryl, —O—C(O)—O—(C$_1$-C$_5$)-alkyl, —O—C(O)—O-aryl, —O—C(O)—O-heteroaryl, or —O—C(O)—N(R$^a$)(R$^b$), wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4b}$ is fluoro. In certain embodiments, R$^{4b}$ is hydrogen, —OH, —O—(C$_1$-C$_5$)-alkyl, —O-aryl, O-heteroaryl, —O—C(O)—(C$_1$-C$_5$)-alkyl, —O—C(O)-aryl, —O—C(O)-heteroaryl, —O—C(O)—O—(C$_1$-C$_5$)-alkyl, —O—C(O)—O-aryl, —O—C(O)—O-heteroaryl, or —O—C(O)—N(R$^a$)(R$^b$), wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4b}$ is selected from —OH, —O—(C$_1$-C$_5$)-alkyl, O-aryl, O-heteroaryl, —O—C(O)—(C$_1$-C$_5$)-alkyl, O—C(O)-aryl, O—C(O)-heteroaryl, and —O—C(O)—N(R$^a$)(R$^b$). In certain embodiments, R$^{4b}$ is hydrogen, halo, —O—C(O)—O—(C$_1$-C$_5$)-alkyl, —O—C(O)—O-aryl, or —O—C(O)—O-heteroaryl, wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4b}$ is selected from hydrogen, halo, —OH, or —O—(C$_1$-C$_5$)-alkyl. In certain embodiments, R$^{4b}$ is —O-aryl, O-heteroaryl, —O—C(O)—(C$_1$-C$_5$)-alkyl, —O—C(O)-aryl, —O—C(O)-heteroaryl, —O—C(O)—O—(C$_1$-C$_5$)-alkyl, —O—C(O)—O-aryl, —O—C(O)—O-heteroaryl, or —O—C(O)—N(R$^a$)(R$^b$), wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4b}$ is selected from —OH, —O—(C$_1$-C$_5$)-alkyl, —O-aryl, O-heteroaryl, —O—C(O)—(C$_1$-C$_5$)-alkyl, —O—C(O)-aryl, —O—C(O)-heteroaryl, —O—C(O)—O—(C$_1$-C$_5$)-alkyl, —O—C(O)—O-aryl, —O—C(O)—O-heteroaryl, and —O—C(O)—N(R$^a$)(R$^b$), wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4b}$ is selected from hydrogen or halo.

In certain embodiments, R$^{4b}$ is in an (R) configuration. In certain embodiments, R$^{4b}$ is in an (S) configuration.

In certain embodiments, R$^{4a}$ is hydrogen. In certain embodiments, R$^{4a}$ is halo, —OH, —O—(C$_1$-C$_5$)-alkyl, —O-aryl, O-heteroaryl, —O—C(O)—(C$_1$-C$_5$)-alkyl, —O—C(O)-aryl, —O—C(O)-heteroaryl, —O—C(O)—O—(C$_1$-C$_5$)-alkyl, —O—C(O)—O-aryl, —O—C(O)—O-heteroaryl, or —O—C(O)—N(R$^a$)(R$^b$), wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4a}$ is fluoro. In certain embodiments, R$^{4a}$ is hydrogen, —OH, —O—(C$_1$-C$_5$)-alkyl, —O-aryl, O-heteroaryl, —O—C(O)—(C$_1$-C$_5$)-alkyl, —O—C(O)-aryl, —O—C(O)-heteroaryl, —O—C(O)—O—(C$_1$-C$_5$)-alkyl, —O—C(O)—O-aryl, —O—C(O)—O-heteroaryl, or —O—C(O)—N(R$^a$)(R$^b$), wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, R$^{4a}$ is selected from —OH, —O—(C$_1$-C$_5$)-alkyl, O-aryl, O-heteroaryl, —O—C(O)—(C$_1$-C$_5$)-alkyl, O—C(O)-aryl, O—C(O)-heteroaryl, and —O—C(O)—N(R$^a$)(R$^b$). In certain embodiments, R$^{4a}$ is hydrogen, halo, —O—C(O)—O—(C$_1$-C$_5$)-alkyl, —O—C(O)—O-aryl, or —O—C(O)—O-heteroaryl, wherein any alkyl, aryl or heteroaryl is optionally substituted with up to 3 substituents independently selected from halo, (C$_1$-C$_5$)-alkyl, O—(C$_1$-C$_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from hydrogen, halo, —OH, or —O—($C_1$-$C_5$)-alkyl. In certain embodiments, $R^{4a}$ is —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, or —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from hydrogen or halo.

In certain embodiments, $R^{4a}$ is in an (S) configuration. In certain embodiments, $R^{4a}$ is in an (R) configuration.

In certain embodiments wherein $R^{4a}$ is —OH, $R^{5a}$ is selected from hydrogen or ($C_1$-$C_5$)-alkyl. In certain embodiments wherein $R^{4a}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), $R^{5a}$ is selected from hydrogen or ($C_1$-$C_5$)-alkyl. In certain embodiments, $R^{5a}$ is fluoro. In certain embodiments, $R^{5a}$ is selected from hydrogen and ($C_1$-$C_5$)-alkyl.

In certain embodiments wherein $R^{4b}$ is —OH, $R^{5b}$ is selected from hydrogen or ($C_1$-$C_5$)-alkyl. In certain embodiments wherein $R^{4b}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), $R^{5b}$ is selected from hydrogen or ($C_1$-$C_5$)-alkyl. In certain embodiments, $R^{5b}$ is fluoro. In certain embodiments, $R^{5b}$ is selected from hydrogen and ($C_1$-$C_5$)-alkyl.

In certain embodiments, $R^2$ is —$CH_2$—. In certain embodiments, $R^2$ is —C(O)—.

In certain embodiments, $R^a$ is selected from H and $C_1$-$C_6$-alkyl. In certain embodiments, $R^a$ is selected from aryl, aralkyl, heteroaryl, and heteroaralkyl.

In certain embodiments, $R^b$ is selected from H and $C_1$-$C_6$-alkyl. In certain embodiments, $R^b$ is selected from aryl, aralkyl, heteroaryl, and heteroaralkyl.

In certain embodiments, $R^c$ is $C_1$-$C_6$-alkyl, aryl, or heteroaryl. In certain embodiments, $R^c$ is selected from aryl, aralkyl, heteroaryl, and heteroaralkyl.

In certain embodiments wherein $R^3$ is selected from a carbocyclic ring, a heterocyclic ring, —$(CH_2)_n$—, and $CH_2C(O)CH_2$, any hydrogen atom in $R^3$ is optionally and independently replaced by halo, ($C_1$-$C_5$)-alkyl, perfluoroalkyl, aryl, heteroaryl, hydroxy, or O—($C_1$-$C_5$)-alkyl. In certain embodiments wherein $R^3$ is —$CH_2$—O—$CH_2$, any hydrogen atom in $R^3$ is optionally and independently replaced by halo, ($C_1$-$C_5$)-alkyl, perfluoroalkyl, aryl, heteroaryl, or O—($C_1$-$C_5$)-alkyl. In certain embodiments, $R^3$ is selected from —$(CH_2)_n$— and —$CH_2$—O—$CH_2$, wherein n is an integer from 1 to 3, and up to two hydrogen atoms in $R^3$ are optionally and independently replaced by ($C_1$-$C_5$)-alkyl. In certain embodiments, $R^3$ is selected from a carbocyclic ring, a heterocyclic ring, and $CH_2C(O)CH_2$, wherein n is an integer from 1 to 3; any hydrogen atom in $R^3$ is optionally and independently replaced by halo, ($C_1$-$C_5$)-alkyl, perfluoroalkyl, aryl, heteroaryl, hydroxy, or O—($C_1$-$C_5$)-alkyl; and any two hydrogen atoms bound to a common carbon atom in $R^3$ are optionally taken together with the carbon atom to which they are bound to form a carbocyclic or heterocyclic ring.

In certain embodiments, $R^{10a}$ is hydrogen. In certain embodiments, $R^{10a}$ is selected from ($C_1$-$C_5$)-alkyl, perfluoroalkyl, O—($C_1$-$C_5$)-alkyl, aryl and heteroaryl, or $R^{10a}$ is taken together with $R^{10b}$ and the carbon atom to which they are bound to form a carbocyclic or heterocyclic ring.

In certain embodiments, $R^{10b}$ is hydrogen. In certain embodiments, $R^{10b}$ is selected from ($C_1$-$C_5$)-alkyl, perfluoroalkyl, O—($C_1$-$C_5$)-alkyl, aryl and heteroaryl, or $R^{10b}$ is taken together with $R^{10a}$ and the carbon atom to which they are bound to form a carbocyclic or heterocyclic ring.

In certain embodiments, $R^1$ is —$OR^a$. In certain embodiments, $R^1$ is selected from —N($R^a$)—$SO_2$—$R^c$ and —N($R^a$)($R^b$). In certain embodiments, $R^1$ is —N($R^a$)—$SO_2$—$R^c$. In certain embodiments, $R^1$ is selected from —$OR^a$ and —N($R^a$)($R^b$). In certain embodiments, $R^1$ is —N($R^a$)($R^b$). In certain embodiments, $R^1$ is selected from —$OR^a$, and —N($R^a$)—$SO_2$—$R^c$.

In certain embodiments, $R^7$ is hydrogen. In certain embodiments, $R^7$ is ($C_1$-$C_5$)-alkyl or two occurrences of $R^7$ may optionally be taken together with the carbons to which they are attached to form a 5- or 6-membered ring.

In certain embodiments, X is —C≡C— and $R^{4b}$ is hydrogen.

In certain embodiments, X is —C≡C— and $R^{4a}$ is hydrogen.

In certain embodiments, X is —C≡C—, $R^{4a}$ is fluoro, and $R^{5a}$ is fluoro.

In certain embodiments, X is —C≡C—, $R^{4b}$ is fluoro, and $R^{5b}$ is fluoro.

In certain embodiments, X is —C≡C—, and each of $R^{4a}$ and $R^{4b}$ is independently selected from —OH, —O—($C_1$-$C_5$)-alkyl, O-aryl, O-heteroaryl, —O—C(O)—$C_1$-$C_5$)-alkyl, O—C(O)-aryl, O—C(O)-heteroaryl, and —O—C(O)—N($R^a$)($R^b$).

In certain embodiments, X is —C≡C— and $R^2$ is —$CH_2$—.

In certain embodiments, X is -(cyclopropyl)-, -(cyclobutyl)-, -(cyclopentyl)-, and -(cyclohexyl)-. In certain embodiments, X is -(cyclopropyl)-.

In certain embodiments, X is —C($R^7$)=C($R^7$)—.

In certain embodiments, each of $R^a$ and $R^b$ is independently selected from H and $C_1$-$C_6$-alkyl; $R^c$ is $C_1$-$C_6$-alkyl; $R^3$ is selected from —$(CH_2)_n$— and —$CH_2$—O—$CH_2$, wherein n is an integer from 1 to 3, and up to two hydrogen atoms in $R^3$ are optionally and independently replaced by ($C_1$-$C_5$)-alkyl; each of $R^{4a}$ and $R^{4b}$ is independently selected from hydrogen, halo, —OH, —O—($C_1$-$C_5$)-alkyl; and each of $R^{10a}$ and $R^{10b}$ is hydrogen.

In certain embodiments, each double bond is in an E-configuration. In certain embodiments, each double bond is in a Z-configuration. In certain embodiments, one double bond is in an E-configuration and one double bond is in a Z-configuration.

In certain embodiments, the any combination of the foregoing is contemplated herein. Those skilled in the art will recognize that all specific combinations of the individual possible residues of the variable regions of the compounds as disclosed herein, e.g., $R^1$, $R^2$, $R^3$, $R^{4a}$, $R^{4b}$, $R^{5a}$, $R^{5b}$, $R^6$, $R^7$, $R^{10a}$, $R^{10b}$, $R^a$, $R^b$, $R^c$, n and X, are within the scope of the invention. As an example, any of the various particular recited embodiments for $R^{4a}$ may be combined with any of the various particular recited embodiments of X.

In certain embodiments, the compound is selected from any one of:

(301)

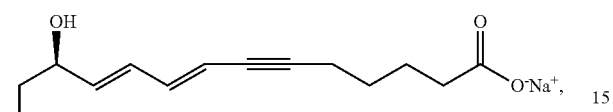

(302)

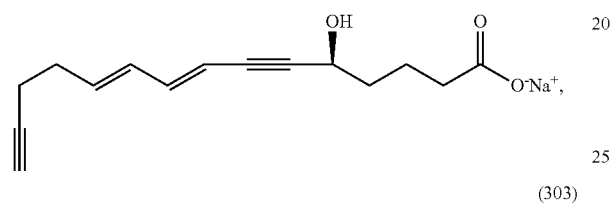

(303)

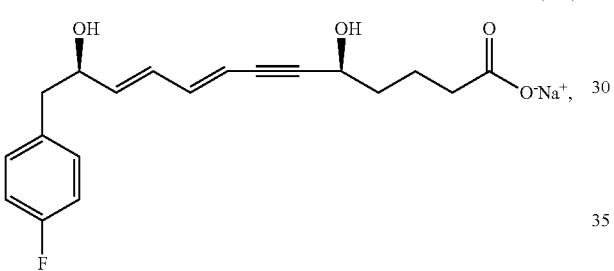

(304)

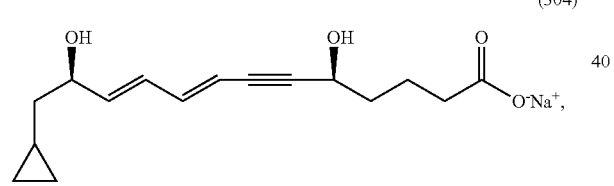

(305)

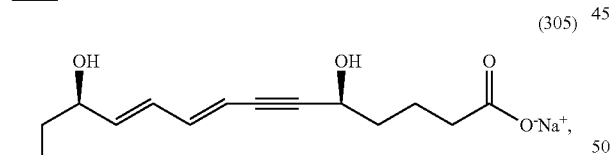

(306)

(307)

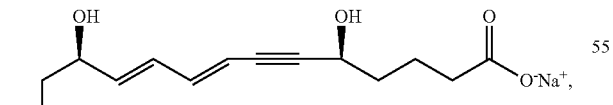

(308)

(309)

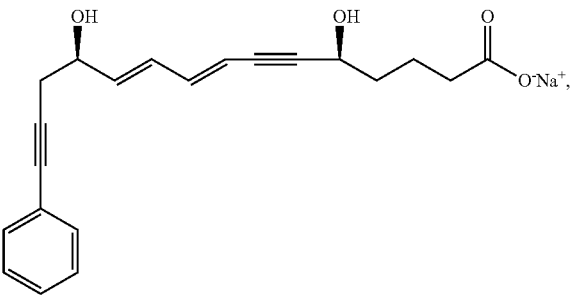

(310)

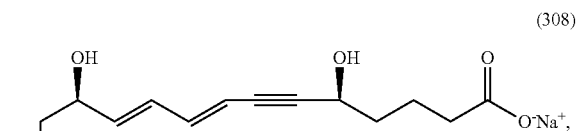

(311)

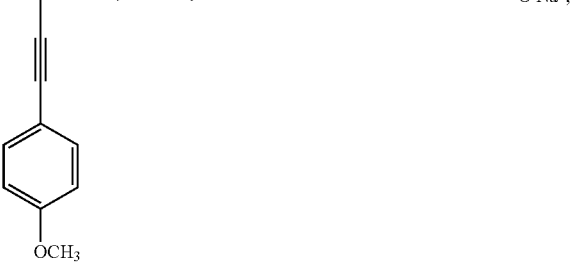

(312)

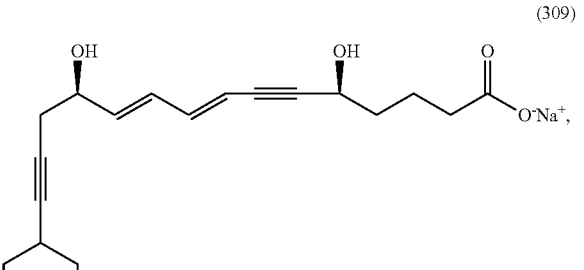

(312) 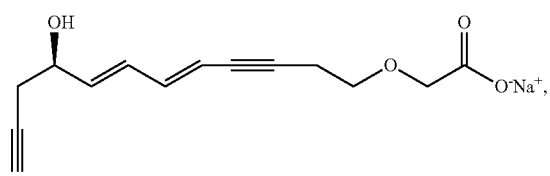
(313) 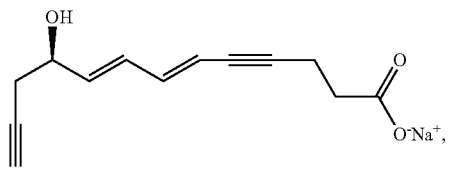
(314) 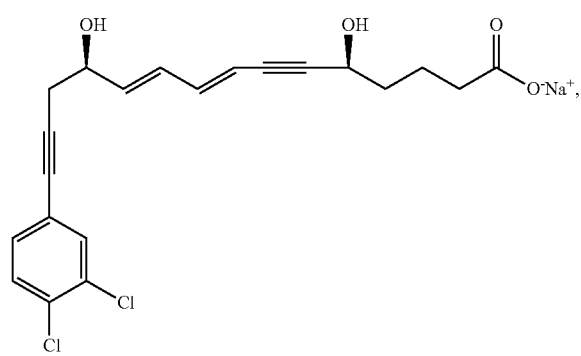
(315) 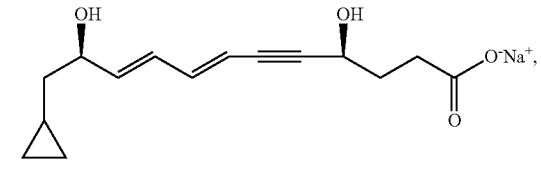
(316) 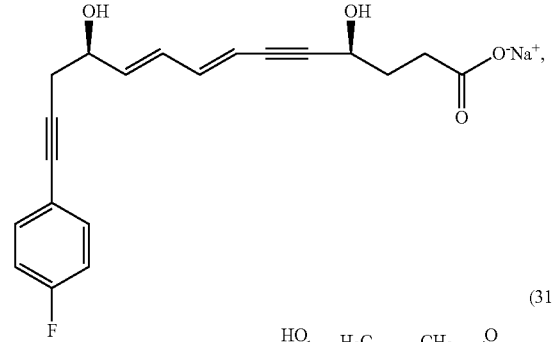
(317) 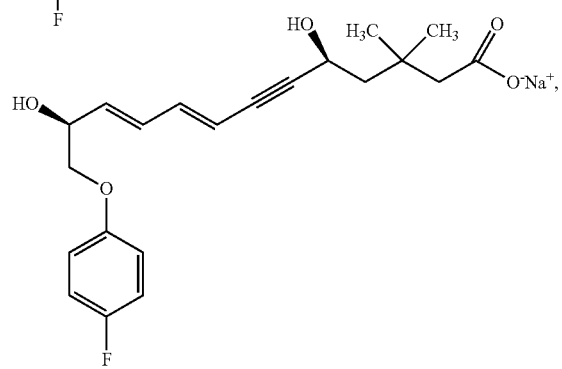
(318) 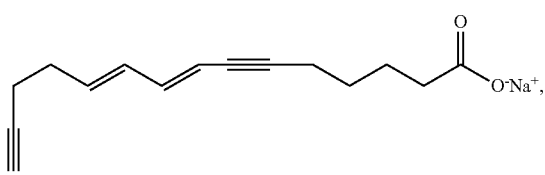
(319) 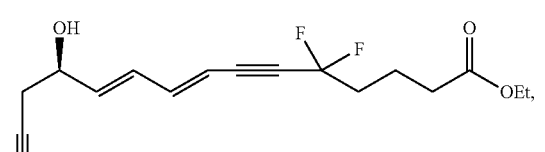
(320) 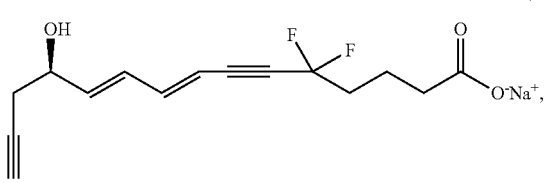
(321) 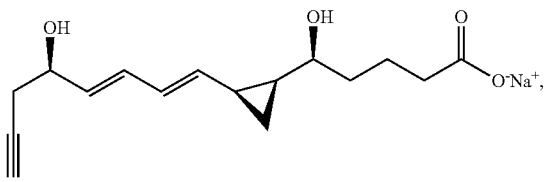
(322) 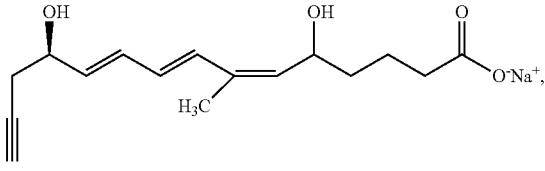
(326) 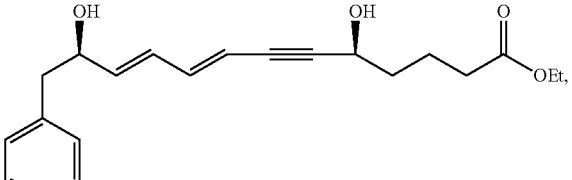
(327) 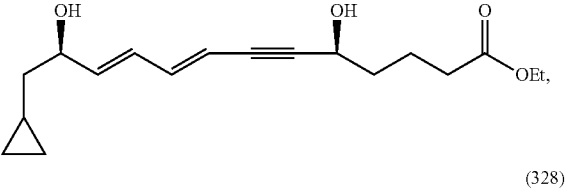
(328) 

(329) 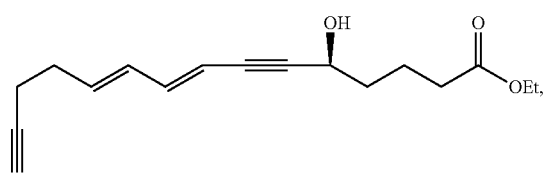
(330) 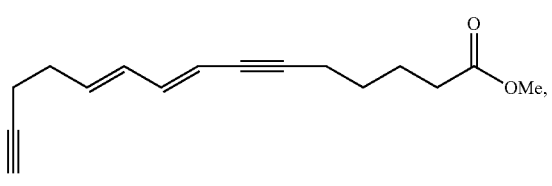
(331) 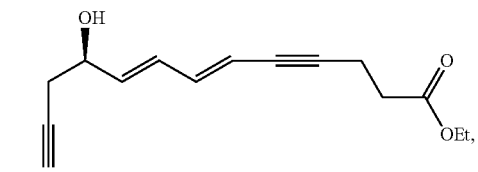
(332) 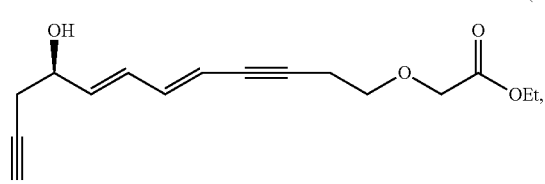
(333) 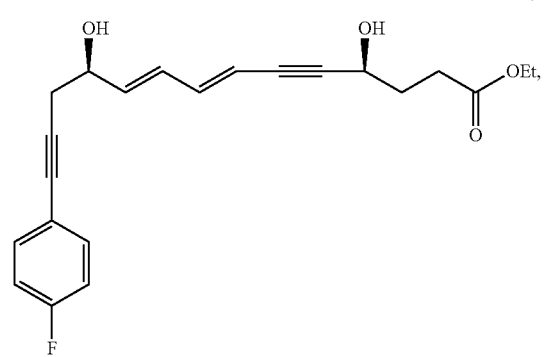
(334) 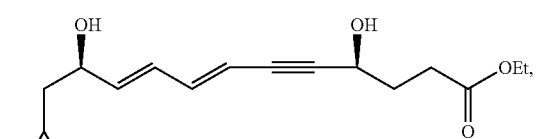
(336) 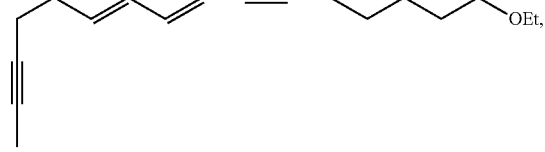
(337) 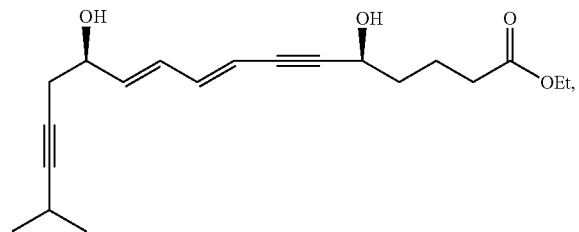
(338) 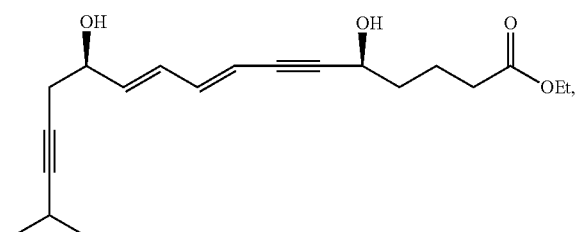
(339) 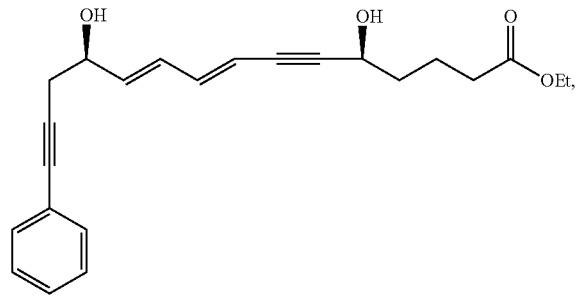
(340) 
(341) 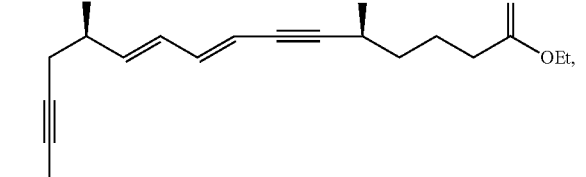

-continued (342)
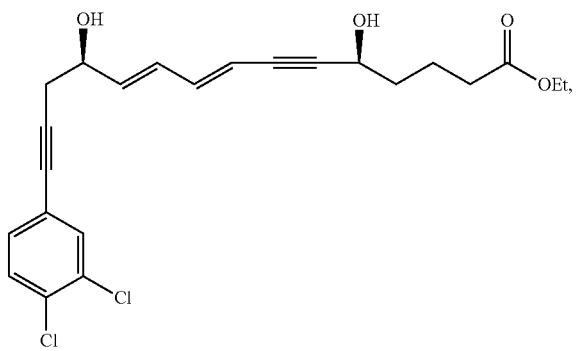

(343)
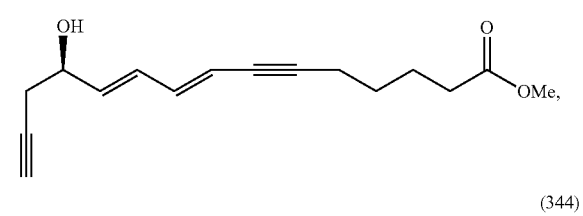

(344)
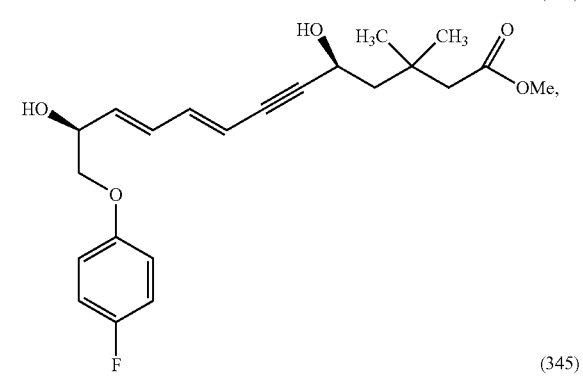

(345)
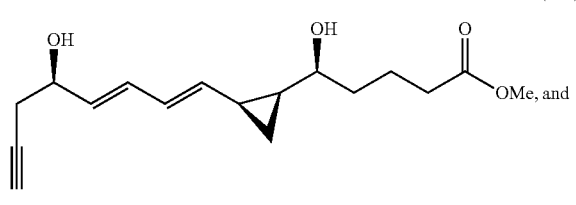

(346)
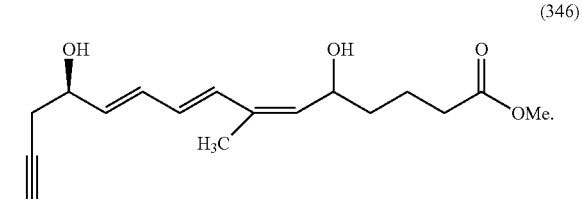 [SMILES: C#CC[C@@H](O)/C=C/C=C/C(C)=C\C(O)CCCC(=O)OC]

In some embodiments an active agent may be a compound of the formula V, (V)
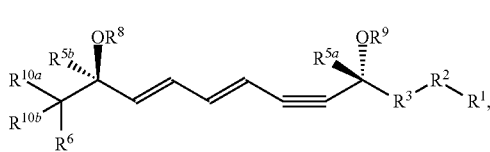

or formula VI, (VI)
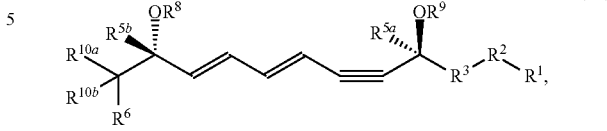

or a pharmaceutically acceptable salt of either of the foregoing, wherein:

$R^1$ is selected from —$OR^a$, —$N(R^a)$—$SO_2$—$R^c$ and —$N(R^a)(R^b)$, wherein each of $R^a$ and $R^b$ is independently selected from H, $C_1$-$C_6$-alkyl, aryl, aralkyl, heteroaryl, and heteroaralkyl, and $R^c$ is selected from $C_1$-$C_6$-alkyl, aryl, aralkyl, heteroaryl, and heteroaralkyl;

$R^2$ is selected from —C(O)—, —$SO_2$—, —PO(OR)—, and tetrazole;

R is selected from hydrogen and alkyl;

$R^3$ is selected from —$(CH_2)_n$— and —$CH_2$—O—$CH_2$, wherein n is an integer from 1 to 3; and optionally up to two hydrogen atoms in $R^3$ are independently replaced by halo, ($C_1$-$C_5$)-alkyl, or O—($C_1$-$C_5$)-alkyl;

each of $R^{5a}$ and $R^{5b}$ is independently selected from hydrogen, ($C_1$-$C_5$)-alkyl, perfluoroalkyl, aryl, and heteroaryl, preferably hydrogen and ($C_1$-$C_5$)-alkyl;

$R^6$ is selected from —C≡CH, -phenyl, —($C_1$-$C_5$)-alkyl-, —($C_3$-$C_7$)-cycloalkyl, —C≡C-phenyl, —C≡C—($C_3$-$C_7$)-cycloalkyl, —C≡C—($C_1$-$C_5$)-alkyl, and —O-phenyl, wherein phenyl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro;

each of $R^8$ and $R^9$ are independently selected from hydrogen, —($C_1$-$C_5$)-alkyl, -aryl, -heteroaryl, —C(O)—($C_1$-$C_5$)-alkyl, —C(O)-aryl, —C(O)-heteroaryl, —C(O)—O—($C_1$-$C_5$)-alkyl, —C(O)—O-aryl, —C(O)—O-heteroaryl, and —C(O)—$N(R^a)(R^b)$, wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro;

each of $R^{10a}$ and $R^{10b}$ is independently selected from hydrogen, ($C_1$-$C_5$)-alkyl, perfluoroalkyl, O—($C_1$-$C_5$)-alkyl, aryl and heteroaryl, or $R^{10a}$ and $R^{10b}$ are taken together with the carbon atom to which they are bound to form a carbocyclic or heterocyclic ring; and wherein each double bond is independently in an E- or a Z-configuration.

In certain embodiments, $R^1$ is —OM, where M is a cation selected from ammonium, tetra-alkyl ammonium, Na, K, Mg, and Zn.

In certain embodiments, $R^2$ and $R^1$ together are

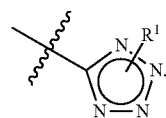

In certain embodiments, $R^2$ is —C(O)—. In certain embodiments, $R^1$ is —$OR^a$, wherein $R^a$ is hydrogen or $C_1$-$C_6$-alkyl. In certain embodiments, $R^3$ is —$(CH_2)_n$—, wherein n is 3. In certain embodiments, $R^6$ is —C≡CH. In certain embodiments, $R^{5a}$ is hydrogen. In certain embodiments, $R^{5b}$ is hydrogen. In certain embodiments, $R^{10a}$ is hydrogen. In certain embodiments, $R^{10b}$ is hydrogen. In certain embodiments, $R^2$ is —C(O)—, $R^1$ is —$OR^a$, wherein $R^a$ is $C_1$-$C_6$-alkyl, $R^3$ is —$(CH_2)_n$—, wherein n is 3, $R^6$ is —C≡CH, $R^{5a}$ is hydrogen, $R^{5b}$ is hydrogen, $R^{10a}$ is hydrogen, and $R^{10b}$ is hydrogen.

In certain embodiments, the compound is selected from any one of:

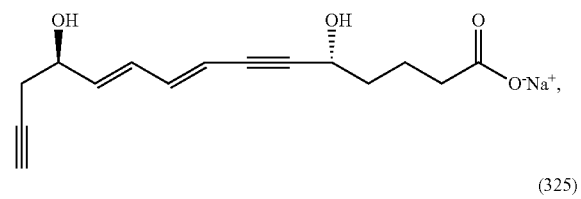

(323)

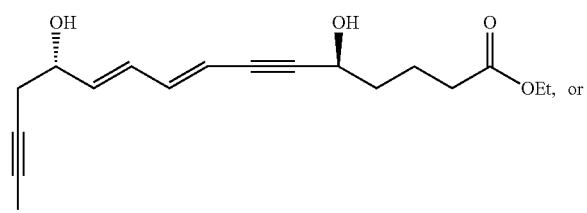

(325)

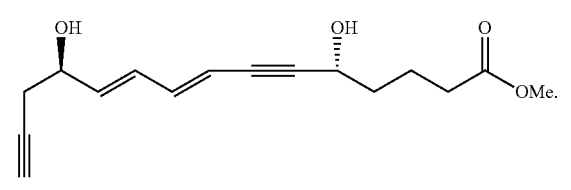

(335)

In some embodiments an active agent may be a compound of formula VII,

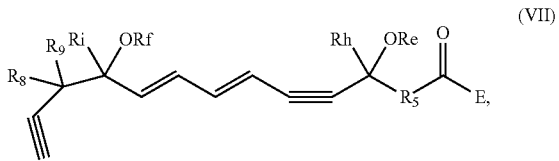

(VII)

and pharmaceutically acceptable salts thereof, wherein:
Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl;
E is a hydroxyl, alkoxy, aryloxy, amino, alkylamino, dialkylamino, or arylamino;
Rh and Ri are independently selected from hydrogen, alkyl, alkenyl, alkynyl, perfluoroalkyl, aryl or heteroaryl;
$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, or $CH_2CH_2$; or iv) $R_5$ is a carbocyclic, heterocyclic, aryl or heteroaryl ring; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring.

In certain embodiments, a compound of formula VII is represented by formula VIII,

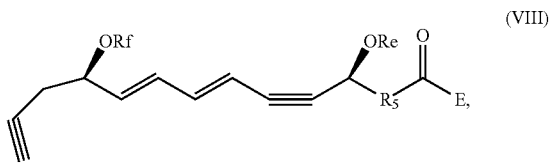

(VIII)

and pharmaceutically acceptable salts thereof, wherein:
Re, Rf, $R_5$, and E are as defined above.

In certain embodiments, a compound of formula VII or VIII is represented by formula IX,

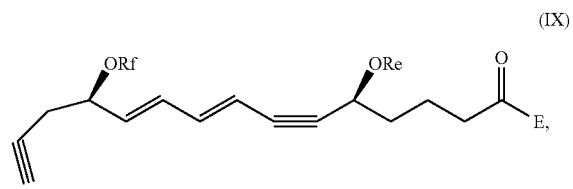

(IX)

and pharmaceutically acceptable salts thereof, wherein:
Re, Rf, and E are as defined above.

Ocular Diseases

In various aspects and embodiments the formulations as disclosed herein may be used to treat or prevent an ocular disease or disorder. Ocular diseases and disorders contemplated herein include anterior segment diseases and posterior segment diseases. Exemplary ocular diseases that may in certain embodiments be treated with formulations as disclosed herein include the following.

Dry eye syndrome (DES, Chronic dry eye, Keratitis sicca; Xerophthalmia; Keratoconjunctivitis sicca) can be defined as a condition that includes a variety of disorders that result in a loss of, or altered composition of, the natural tear film, which maintains the surface of the eye. Without this tear film, vision is impaired and patients may suffer severe ocular discomfort. DES can be caused by excessive tear evaporation or by a reduction of tear production in the lacrimal gland, which is the site of tear production. Though the exact causes of this condition are unknown, there is evidence supporting the link between reduced tear production and inflammation of one or more components of the lacrimal apparatus. Currently available medications for DES are leaving substantial room for more effective and better tolerated products.

DES may also be a manifestation of Sjogren's syndrome which is an autoimmune disorder in which the glands that produce tears and saliva are destroyed. This leads to dry mouth, decreased tearing, and other dry mucous membranes.

Noninfectious uveitis is a chronic inflammatory, putative Th1/Th17-mediated autoimmune disease associated with substantial visual morbidity and is potentially blinding. Blindness from uveitis usually does not occur from a single inflammatory episode; rather, cumulative damage results from recurrent episodes of inflammation. The inflammatory sequelae resulting in vision loss may include one or more of cystoid macular edema, cataracts, vitreous debris, glaucoma, macular pathology (scarring and atrophy), optic neuropathy, and retinal detachment.

Anterior uveitis (iritis) occurs in the front of the eye and is the most common form of uveitis. Par planitis is an inflammation of the pars plana, a narrow area between the iris and the choroid. This condition occurs more frequently in young men, but is usually not associated with another disease. Posterior uveitis (chondroitis) affects primarily the choroid; the back portion of the uveal tract. If the retina is also involved, it is called chorioretinitis. Posterior uveitis may occur in association with an autoimmune disease, or follow a systemic infection. In posterior uveitis, inflammation can last from months to years and may cause permanent vision damage, even with treatment.

Uveitis can cause vision impairment, ocular pain, and loss of vision. It is estimated that about 10% of new cases of blindness in the U.S. are caused by uveitis. Approximately 300,000 people suffer from uveitis in the U.S. alone, the majority of whom are affected by anterior uveitis. The only therapeutic class approved by the FDA for treatment of uveitis is corticosteroids, which are noted for multiple side effects, such as hypertension, hyperglycemia, and hypercholesterolemia, and in the eye, glaucoma and cataract formation.

Conjunctivitis (pink eye) describes a group of diseases that cause swelling, itching, burning, and redness of the conjunctiva, the protective membrane that lines the eyelids and covers exposed areas of the sclera, or white of the eye.

Keratitis is an inflammation of the cornea (clear portion in the front of the eye). Keratitis can be caused by an infection (bacterial, fungal, viral, parasite, etc.) or a non-infectious agent (e.g., certain types of auto-immune diseases are associated with a variety of non-infectious keratitises).

Keratoconjunctivitis refers to an inflammation of the cornea and conjunctiva.

Vernal keratoconjunctivitis (VKC) is a recurrent ocular inflammatory disease characterized by hard, elevated, cobblestone like bumps on the upper eyelid. There may also be swellings and thickening of the conjunctiva. The conjunctiva is the outermost membrane which lines the eyelids as well as the exposed parts of the eye, except for the cornea.

Atopic keratoconjunctivitis is the result of a condition called atopy. Atopy is a genetic condition whereby the immune system produces higher than normal antibodies in response to a given allergen.

Systemic immune mediated diseases such as cicatrizing conjunctivitis and other autoimmune disorders of the ocular surface represent a clinically heterogeneous group of conditions where acute and chronic autoreactive mechanisms can cause significant damage to the eye. When severe and affecting the epithelium and substantia propria of the conjunctiva, cicatrization can ensue, leading to significant mechanical alterations as a result of the fibrosis. These conditions, though generally infrequent, can be the cause of profound pathology and visual disability.

Blepharitis is a common condition that causes inflammation of the eyelids.

Scleritis is a serious inflammatory disease that affects the white outer coating of the eye, known as the sclera.

Age-related macular degeneration (AMD) is a disease associated with aging that gradually destroys sharp, central vision. AMD affects the macula, which is located at the center of the retina. AMD occurs in two forms: wet and dry. Wet AMD occurs when abnormal blood vessels behind the retina start to grow under the macula. These new blood vessels tend to be very fragile and often leak blood and fluid. The blood and fluid raise the macula from its normal place at the back of the eye. Damage to the macula occurs rapidly. Dry AMD occurs when the light-sensitive cells in the macula slowly break down, gradually blurring central vision in the affected eye.

Diabetes can affect the eye in a number of ways. Diabetic retinopathy (DR) is a complication of diabetes that results from damage to the blood vessels of the light-sensitive tissue at the back of the eye (the retina). At first, diabetic retinopathy may cause no symptoms or only mild vision problems. Eventually, however, diabetic retinopathy can result in blindness. Diabetic macular edema (DME) is the swelling of the retina in diabetes mellitus due to leaking of fluid from blood vessels within the macula.

Ocular neovascularization is the abnormal or excessive formation of blood vessels in the eye. Ocular neovascularization has been shown in diabetic retinopathy and age-related macular degeneration (AMD).

Proliferative vitreoretinopathy (PVR) is scar tissue formation within the eye. "Proliferative" because cells proliferate and "vitreoretinopathy" because the problems involve the vitreous and retina. In PVR scar tissue forms in sheets on the retina which contract. This marked contraction pulls the retina toward the center of the eye and detaches and distorts the retina severely. PVR can occur both posteriorly and anteriorly with folding of the retina both anteriorly and circumferentially.

The cytomegalovirus (CMV) is related to the herpes virus and is present in almost everyone. When a person's immune system is suppressed because of disease (HIV), organ or bone marrow transplant, or chemotherapy, the CMV virus can cause damage and disease to the eye and the rest of the body. CMV affects the eye in about 30% of the cases by causing damage to the retina. This is called CMV retinitis.

Optic neuritis occurs when the optic nerve becomes inflamed and the myelin sheath becomes damaged or is destroyed. Nerve damage that occurs in the section of the optic nerve located behind the eye, is called retrobulbar neuritis, which is another term sometimes used for optic neuritis.

Also known as macular pucker, epiretinal membrane is a scar-tissue like membrane that forms over the macula. It typically progresses slowly and affects central vision by causing blurring and distortion. As it progresses, the pulling of the membrane on the macula may cause swelling.

In an embodiment, the compositions can be used for preventing transplant rejection of, for example, corneal allografts following transplantation. It is well known that in inflammation T-lymphocytes play a critical role in mediating rejection of foreign tissues. Prevention of rejection is of paramount importance in maintaining the health of transplanted corneas. Rejection may occur in any of the layers comprising the cornea, for example, the corneal epithelium, the corneal stroma or the corneal endothelium. The functioning of the cornea can be compromised following endothelial rejection. The endothelial layer serves to maintain the cornea in a compact state, acting as a pump by removing water from the corneal stroma. If the function of the endothelial layer is compromised, disorientation of collagen fibers can ensue, and transparency of the cornea can be lost. Human endothelial cells are non-replicative, and as a consequence, donor cell loss in the setting of rejection is irreversible and may lead to diminished graft function and survival. Thus, the goal of either prevention or treatment of rejection in corneal transplant recipients is to minimize endothelial cell loss. The compositions of the present disclosure can be used for the prevention of rejection following corneal allograft transplantation.

Additional Formulation Ingredients

The compositions of the present disclosure may also contain other components such as, but not limited to, additives, adjuvants, buffers, tonicity agents, bioadhesive polymers, and preservatives. In any of the compositions of this disclosure for topical to the eye, the mixtures are preferably formulated at about pH 5 to about pH 8. This pH range may be achieved by the addition of buffers to the composition as described in the examples. In an embodiment, the pH range in the composition in a formulation is about pH 6.6 to about pH 7.0. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The mixed micellar compositions of the present disclosure are stable in buffered aqueous solution. That is, there is no adverse interaction between the buffer and any other component that would cause the compositions to be unstable.

Tonicity agents include, for example, mannitol, sodium chloride, xylitol, etc. These tonicity agents may be used to adjust the osmolality of the compositions. In one aspect, the osmolality of the formulation is adjusted to be in the range of about 250 to about 350 mOsmol/kg. In a preferred aspect, the osmolality of the formulation is adjusted to between about 280 to about 300 mOsmol/kg.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the calcineurin inhibitor or mTOR inhibitor, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose. In an embodiment, the sugars can be incorporated into a composition prior to hydrating the thin film (i.e., internally). In another embodiment, the sugars can be incorporated into a composition during the hydration step (i.e., externally) (see Example 17). In an embodiment, an aqueous, clear, mixed micellar solution of the present disclosure includes additives such as sugars.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight. Bioadhesion systems have been used in dentistry, orthopedics, ophthalmology, and in surgical applications. However, there has recently emerged significant interest in the use of bioadhesive materials in other areas such as soft tissue-based artificial replacements, and controlled release systems for local release of bioactive agents. Such applications include systems for release of drugs in the buccal or nasal cavity, and for intestinal or rectal administration.

In an embodiment, a composition of the present disclosure includes at least one bioadhesive polymer. The bioadhesive polymer can enhance the viscosity of the composition and thereby increase residence time in the eye. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil. In an embodiment, the polymer excipient is selected from PVP-K-90, PVP-K-30 or HPMC. In an embodiment, the polymer excipient is selected from PVP-K-90 or PVP-K-30.

In an embodiment, if a preservative is desired, the compositions may optionally be preserved with any of many well-known preservatives, including benzyl alcohol with/without EDTA, benzalkonium chloride, chlorhexidine, Cosmocil® CQ, or Dowicil® 200. In certain embodiments, it may be desirable for a formulation as described herein to not include any preservatives. In this regard, preservatives may in some embodiments not be necessary or desirable in formulations included in single use containers. In other embodiments it may be advantageous to include preservatives, such as in certain embodiments in which the formulations are included in a multiuse container.

The ophthalmic compositions can be administered topically to the eye as biocompatible, aqueous, clear mixed micellar solutions. The compositions have the drugs incorporated and/or encapsulated in micelles which are dispersed in an aqueous medium.

Non-Limiting List of Exemplary Embodiments

In addition to the aspects and embodiments described and provided elsewhere in this disclosure, the following non-limiting list of particular embodiments are specifically contemplated.

1. An ophthalmic formulation, comprising an active agent, a polyoxyl lipid or fatty acid and a polyalkoxylated alcohol.

2. An ophthalmic formulation, comprising an active agent, and a 40 polyoxyl lipid or fatty acid.

3. An ophthalmic formulation, comprising an active ingredient and a polyoxyl lipid or fatty acid; wherein said polyoxyl lipid or fatty acid is present in an amount equal to or greater than 1% of said formulation.

4. An ophthalmic formulation, comprising an active agent and a polyoxyl lipid or fatty acid; wherein said formulation comprises nanomicelles.

5. An ophthalmic formulation, comprising an active agent, 1-5% of one or more selected from the group consisting of HCO-40, HCO-60, HCO-80 and HCO-100; and about 0.01-0.1% octoxynol-40.

6. An ophthalmic formulation, comprising an active agent, 1-5% of one or more selected from the group consisting of HCO-40, HCO-60, HCO-80 and HCO-100; and about 0.01-0.1% octoxynol-40.

7. An ophthalmic formulation, comprising greater than 0.2% of an active agent, 1-5% of one or more selected from the group consisting of HCO-40, HCO-60, HCO-80 and HCO-100; and about 0.01-0.1% octoxynol-40.

8. An ophthalmic formulation, comprising an active agent, 1.5-4% of one or more polyoxl lipids selected from the group consisting of HCO-40, HCO-60, HCO-80 and HCO-100; and about 0.01-0.1% octoxynol-40.

9. An ophthalmic formulation, comprising an active agent, 1.5-4% of polyoxl lipids or fatty acids; and about 0.01-0.1% octoxynol-40.

10. An ophthalmic formulation, comprising an active agent, 1.5-4% of polyoxl lipids or fatty acids; and about 0.01-0.1% octoxynol-40; wherein the formulation comprises nanomicelles.

11. An ophthalmic formulation, comprising a hydrophobic active agent, 1.5-4% of polyoxl lipids or fatty acids; and about 0.01-0.1% octoxynol-40; wherein the formulation comprises nanomicelles.

12. An ophthalmic formulation, comprising an active agent, about 4% of one or more selected from the group consisting of HCO-40, HCO-60, HCO-80 and HCO-100; and about 0.01-0.1% octoxynol-40.

13. An ophthalmic formulation, comprising an active agent, about 4% of HCO-60 and about 0.01-0.1% octoxynol-40.

14. An ophthalmic formulation, comprising an active agent, 1-5% of one or more selected from the group consisting of HCO-40, HCO-60, HCO-80 and HCO-100; and about 0.01% octoxynol-40.

15. An ophthalmic formulation, comprising an active agent, 1-5% of one or more selected from the group consisting of HCO-40, HCO-60, HCO-80 and HCO-100; and about 0.01% octoxynol-40.

16. An ophthalmic formulation, comprising greater than 0.2% of an active agent, 1-5% of one or more selected from the group consisting of HCO-40, HCO-60, HCO-80 and HCO-100; and about 0.01% octoxynol-40.

17. An ophthalmic formulation, comprising an active agent, 1.5-4% of one or more polyoxl lipids selected from the group consisting of HCO-40, HCO-60, HCO-80 and HCO-100; and about 0.01% octoxynol-40.

18. An ophthalmic formulation, comprising an active agent, 1.5-4% of polyoxl lipids or fatty acids; and about 0.01% octoxynol-40.

19. An ophthalmic formulation, comprising an active agent, 1.5-4% of polyoxl lipids or fatty acids; and about 0.01% octoxynol-40; wherein the formulation comprises nanomicelles.

20. An ophthalmic formulation, comprising a hydrophobic active agent, 1.5-4% of polyoxl lipids or fatty acids; and about 0.01% octoxynol-40; wherein the formulation comprises nanomicelles.

21. An ophthalmic formulation, comprising an active agent, about 4% of one or more selected from the group consisting of HCO-40, HCO-60, HCO-80 and HCO-100; and about 0.01% octoxynol-40.

22. An ophthalmic formulation, comprising an active agent, about 4% of HCO-60 and about 0.01% octoxynol-40.

23. The formulation of any of the preceding embodiments, wherein said polyoxyl lipid or fatty acid is between 0.5 and 6% by weight of said formulation.

24. The formulation of any of the preceding embodiments, wherein said polyoxyl lipid or fatty acid is between 0.5 and 2% by weight of said formulation.

25. The formulation of any of the preceding embodiments, wherein said polyoxyl lipid or fatty acid is between 0.5 and 3% by weight of said formulation.

26. The formulation of any of the preceding embodiments, wherein said polyoxyl lipid or fatty acid is between 0.5 and 4% by weight of said formulation.

27. The formulation of any of the preceding embodiments, wherein said polyoxyl lipid or fatty acid is between 0.5 and 5% by weight of said formulation.

28. The formulation of any of the preceding embodiments, wherein said polyoxyl lipid or fatty acid is between 1 and 6% by weight of said formulation.

29. The formulation of any of the preceding embodiments, wherein said polyoxyl lipid or fatty acid is between 1 and 2% by weight of said formulation.

30. The formulation of any of the preceding embodiments, wherein said polyoxyl lipid or fatty acid is between 1 and 3% by weight of said formulation.

31. The formulation of any of the preceding embodiments, wherein said polyoxyl lipid or fatty acid is between 1 and 4% by weight of said formulation.

32. The formulation of any of the preceding embodiments, wherein said polyoxyl lipid or fatty acid is between 1 and 5% by weight of said formulation.

33. The formulation of any of the preceding embodiments, wherein said polyoxyl lipid or fatty acid is between 1 and 6% by weight of said formulation.

34. The formulation of any of the preceding embodiments, wherein said polyoxyl lipid or fatty acid is between 2 and 6% by weight of said formulation.

35. The formulation of any of the preceding embodiments, wherein said polyoxyl lipid or fatty acid is between 3 and 6% by weight of said formulation.

36. The formulation of any of the preceding embodiments, wherein said polyoxyl lipid or fatty acid is between 4 and 6% by weight of said formulation.

37. The formulation of any of the preceding embodiments, wherein said polyoxyl lipid or fatty acid is between 2 and 5% by weight of said formulation.

38. The formulation of any of the preceding embodiments, wherein said polyoxyl lipid or fatty acid is between 3 and 5% by weight of said formulation.

39. The formulation of any of the preceding embodiments, wherein said polyoxyl lipid or fatty acid is about 4% by weight of said formulation.

40. The formulation of any of the preceding embodiments, wherein said polyoxyl lipid or fatty acid is greater than about 0.7% by weight of said formulation.

41. The formulation of any of the preceding embodiments, wherein said polyoxyl lipid or fatty acid is greater than about 1% by weight of said formulation.

42. The formulation of any of the preceding embodiments, wherein said polyoxyl lipid or fatty acid is greater than about 1.5% by weight of said formulation.

43. The formulation of any of the preceding embodiments, wherein said polyoxyl lipid or fatty acid is greater than about 2% by weight of said formulation.

44. The formulation of any of the preceding embodiments, wherein said polyoxyl lipid or fatty acid is greater than about 3% by weight of said formulation.

45. The formulation of any of the preceding embodiments, wherein said polyalkoxylated alcohol if present is between 0.002 and 4% by weight of said formulation.

46. The formulation of any of the preceding embodiments, wherein said polyalkoxylated alcohol if present is between 0.005 and 3% by weight of said formulation.

47. The formulation of any of the preceding embodiments, wherein said polyalkoxylated alcohol if present is between 0.005 and 2% by weight of said formulation.

48. The formulation of any of the preceding embodiments, wherein said polyalkoxylated alcohol if present is between 0.005 and 1% by weight of said formulation.

49. The formulation of any of the preceding embodiments, wherein said polyalkoxylated alcohol if present is between 0.005 and 0.5% by weight of said formulation.

50. The formulation of any of the preceding embodiments, wherein said polyalkoxylated alcohol if present is between 0.005 and 0.1% by weight of said formulation.

51. The formulation of any of the preceding embodiments, wherein said polyalkoxylated alcohol if present is between 0.005 and 0.05% by weight of said formulation.

52. The formulation of any of the preceding embodiments, wherein said polyalkoxylated alcohol if present is between 0.008 and 0.02% by weight of said formulation.

53. The formulation of any of the preceding embodiments, wherein said polyalkoxylated alcohol if present is about 0.01% by weight of said formulation.

54. The formulation of any of the preceding embodiments, wherein said active agent is a resolvin or a resolvin-like compound.

55. The formulation of any of the preceding embodiments, wherein said active agent is a resolvin.

56. The formulation of any of the preceding embodiments, wherein said active ingredient is present in said formulation in an amount greater than 0.2%.

57. The formulation of any of the preceding embodiments, wherein said active ingredient is present in said formulation in an amount greater than 0.3%.

58. The formulation of any of the preceding embodiments, wherein said active ingredient is present in said formulation in an amount greater than 0.4%.

59. The formulation of any of the preceding embodiments, wherein said active ingredient is present in said formulation in an amount greater than 0.5%.

60. The formulation of any of the preceding embodiments, wherein said active ingredient is present in said formulation in an amount greater than 0.6%.

61. The formulation of any of the preceding embodiments, wherein said active ingredient is present in said formulation in an amount greater than 0.7%.

62. The formulation of any of the preceding embodiments, wherein said active ingredient is present in said formulation in an amount greater than 0.8%.

63. The formulation of any of the preceding embodiments, wherein said active ingredient is present in said formulation in an amount greater than 0.9%.

64. The formulation of any of the preceding embodiments, wherein said active ingredient is present in said formulation in an amount greater than 1%.

65. The formulation of any of the preceding embodiments, wherein said active ingredient is present in said formulation in an amount greater than 1.5%.

66. The formulation of any of the preceding embodiments, wherein said active ingredient is present in said formulation in an amount greater than 2%.

67. The formulation of any of the preceding embodiments, wherein said active ingredient is present in said formulation in an amount greater than 3%.

68. The formulation of any of the preceding embodiments, wherein said active ingredient is present in said formulation in an amount greater than 4%.

69. The formulation of any of the preceding embodiments, wherein said polyoxyl lipid or fatty acid is a polyoxyl castor oil.

70. The formulation of any of the preceding embodiments, wherein said polyoxyl lipid or fatty acid is one or more selected from HCO-60, HCO-80 or HCO-100.

71. The formulation of any of the preceding embodiments, wherein said polyoxyl lipid or fatty acid is HCO-60.

72. The formulation of any of the preceding embodiments, wherein said polyalkoxylated alcohol, if present is octoxynol-40.

73. The formulation of any of the preceding embodiments, wherein said active agent is one or more selected from the group consisting of calcineurin inhibitors, mTOR inhibitors, peptides, eicosanoids (e.g. prostacyclins and prostaglandins), anti-inflammatory drugs (such as NSAIDS), autonomic drugs (e.g. beta-blockers, alpha-blockers, beta-agonists, and alpha-agonists), biologics, gene therapy agents (e.g. viral vectors), anti-infectives (e.g. anti-fungals, antibiotics, and antivirals), retinoids, RNAi, photo sensitizers, steroids (e.g., estrogens and derivatives thereof, and corticosteriods), mixture drugs, immuno-modulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists, resolvins (or resolvin-like compounds), lipoxins, and oxylipins.

74. The formulation of any of the preceding embodiments, wherein said active agent is one or more selected from the group consisting of cyclosporine A, voclosporin, ascomycin, tacrolimus, pimecrolimus, an analog thereof, or a pharmaceutically acceptable salt thereof.

75. The formulation of any of the preceding embodiments, wherein said active agent is cyclosporine A.

76. The formulation of any of the preceding embodiments, wherein said active agent is voclosporin.

77. The formulation of any of the preceding embodiments, wherein said active agent is one or more selected from the group consisting of sirolimus (rapamycin), temsirolimus, everolimus, an analog thereof, or a pharmaceutically acceptable salt thereof.

78. The formulation of any of the preceding embodiments, wherein said active agent is a compound of formula A, a compound of any one of formulae 1-49, formulae I-IX, a lipoxin compound, an oxylipin compound, a prodrug of any of the foregoing, or a pharmaceutically acceptable salt of any of the foregoing.

79. The formulation of any of the preceding embodiments, wherein said active agent is a compound of formula A, a compound of any one of formulae 1-49, formulae I-IX, a lipoxin compound, an oxylipin compound, a prodrug of any of the foregoing, or a pharmaceutically acceptable salt of any of the foregoing.

80. The formulation of any of the preceding embodiments, wherein said active agent comprises a combination of two different agents.

81. The formulation of any of the preceding embodiments, wherein the active agent comprises two or more active agents selected from the group consisting of a resolvin or resolvin-like compound, a steroid (such as a corticosteroid), cyclosporine A, and voclosporin.

82. The formulation of any of the preceding embodiments, wherein the active agent comprises a resolvin and a corticosteroid.

83. The formulation of any of the preceding embodiments, wherein the active agent comprises cyclosporine A and a corticosteroid.

84. The formulation of any of the preceding embodiments, wherein the active agent comprises a resolvin, cyclosporine A and a corticosteroid.

85. The formulation of any of the preceding embodiments, wherein said active agent is a compound of formula I,

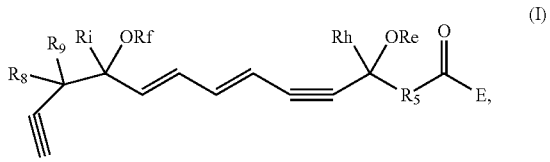

or a pharmaceutically acceptable salt thereof, wherein:
Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl;
E is a branched alkoxy;
Rh and Ri are independently selected from hydrogen, alkyl, alkenyl, alkynyl, perfluoroalkyl, aryl or heteroaryl;
$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, or $CH_2CH_2$; or iv) $R_5$ is a carbocyclic, heterocyclic, aryl or heteroaryl ring; and
$R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring.

86. The formulation of any of the preceding embodiments, wherein said active agent is a compound of formula I, wherein
Re, Rf, Rh, Ri, $R_8$ and $R_9$ are hydrogen;
E is branched alkoxy (such as isopropyl); and
$R_5$ is $CH_2CH_2CH_2$.

87. The formulation of any of the preceding embodiments, wherein said resolvin, if present, is a compound of Formula I.

88. The formulation of any of the preceding embodiments, wherein said resolvin, if present, is compound 1001.

89. The formulation of any of the preceding embodiments, wherein said formulation comprises a preservative.

90. The formulation of any of the preceding embodiments, wherein said formulation comprises one or more preservatives selected from the group consisting of benzyl alcohol with/without EDTA, benzalkonium chloride, chlorhexidine, Cosmocil® CQ, and Dowicil® 200.

91. The formulation of any of the preceding embodiments, wherein said formulation does not include preservatives.

92. The formulation of any of the preceding embodiments, wherein said formulation does not include benzyl alcohol with/without EDTA, benzalkonium chloride, chlorhexidine, Cosmocil® CQ, or Dowicil® 200.

93. A method of treating or preventing an ocular disease or condition, said method comprising topically administering a formulation of any of the preceding embodiments.

94. A method of treating or preventing an ocular disease or condition, said method comprising topically administering a formulation of any of the preceding embodiments; wherein said disease is an anterior segment disease.

95. A method of treating or preventing an ocular disease or condition, said method comprising topically administering a formulation of any of the preceding embodiments; wherein said disease is an posterior segment disease.

96. A method of treating or preventing an ocular disease or condition, said method comprising topically administering a formulation of any of the preceding embodiments; wherein said disease is one or more selected from the group consisting of dry eye syndrome, Sjogren's syndrome, uveitis, anterior uveitis (iritis), chorioretinitis, posterior uveitis, conjunctivitis, allergic conjunctivitis, keratitis, keratoconjunctivitis, vernal keratoconjunctivitis (VKC), atopic keratoconjunctivitis, systemic immune mediated diseases such as cicatrizing conjunctivitis and other autoimmune disorders of the ocular surface, blepharitis, scleritis, age-related macular degeneration (AMD), diabetic retinopathy (DR), diabetic macular edema (DME), ocular neovascularization, age-related macular degeneration (ARMD), proliferative vitreoretinopathy (PVR), cytomegalovirus (CMV) retinitis, optic neuritis, retrobulbar neuritis, and macular pucker.

97. A method of treating or preventing an ocular disease or condition, said method comprising topically administering a formulation of any of the preceding embodiments; wherein said disease is dry eye syndrome.

98. A method of treating or preventing an ocular disease or condition, said method comprising topically administering a formulation of any of the preceding embodiments; wherein said disease is allergic conjunctivitis.

99. A method of treating or preventing an ocular disease or condition, said method comprising topically administering a formulation of any of the preceding embodiments; wherein said disease is age-related macular degeneration (AMD).

The following examples are provided to further illustrate aspects of the invention. These examples are non-limiting and should not be construed as limiting any aspect of the invention.

Example 1

Preparation of Mixed Nanomicellar Resolvin Formulation Using Dialysis Method

Mixed nanomicellar formulation of compound 1001 was prepared by dialysis method with varying ratio of polymers and the drug. Experimental design software, JMP 9.0 was used to design the experiments and analyze the results. Accurately weighted quantities of two polymers namely polyoxyl hydrogenated castor-60 (HCO-60) and octoxynol- 40 (Oc-40) were dissolved in 300 microliter volume of propylene glycol. Eighty microliter (or 80 mg of compound 1001 in PG) of propylene glycol containing compound 1001 was added to this polymer mixture and vortex mixed to get a clear homogenous solution. The volume of the mixture was made up (500 microliters) with propylene glycol. The solution was vortex mixed to get a homogenous solution. A volume of 500 microliter distilled deionized water was added to this mixture to obtain a total volume of 1000 microliter (1 milliliter). Addition of water to the drug polymer mixture in organic solvent should spontaneously generate micelles thereby entrapping the pharmaceutical active agent in the hydrophobic core of mixed nanomicelles. The mixture was transferred to a dialysis bag (molecular weight cut off 1000) and transferred to a beaker containing one liter of distilled deionized water. Beaker and the contents were protected from sunlight by covering with aluminum foil and were kept under slow constant stirring at room temperature. Dialysis of the mixture was carried over a period of 24 h to remove the water soluble organic solvent, propylene glycol, from the mixture. Water in the dialysis chamber was changed at predetermined time points: 1 h, 2 h, 4 h, 6 h, 12 h and 24 h. At the end of dialysis (24 h), the contents of the dialysis bag were carefully transferred to a 15-mL centrifuge tube and formulations were subjected to sonication in water bath (time range from 0 min to 5 min). The final volume was made up with 2× phosphate buffer saline and adjusted pH of the formulation to 6.5±0.1. The resultant formulation was filtered with 0.22 micrometer nylon filter to remove any foreign particulate matter.

The prepared formulations were subjected to various tests such as entrapment efficiency, loading efficiency, mixed nanomicellar size and polydispersity index.

Mixed Nanomicellar Size and Polydispersity Index:

The formulation size and polydispersity index were determined with Zetasizer, Malvern Instruments, NJ. In brief, approximately 1 ml of each formulation was transferred to a cuvette and placed in the instrument. A laser beam of light was used to determine the mixed nanomicellar size. The results of the size are summarized in Table 2.

Entrapment Efficiency:

To determine the entrapment efficiency of the formulation, all the prepared formulations were subjected to entrapment efficiency test. Briefly, formulations were vortex mixed for homogeneity and 1 mL was transferred to a fresh (1.5 mL) eppendorf tube. Each formulation was lyophilized to obtain a solid at the bottom of eppendorf tube. The obtained solid was suspended in 1 mL of organic solvent (diethyl ether) to generate reverse micelles and release the drug into the external organic solvent. The organic solvent was evaporated overnight in speed vacuum. The resultant reversed micelles were resuspended in 1 mL of 2-propanol (dilution factor was taken into account) and further diluted to determine the concentration of compound 1001 entrapped in each micellar preparation with HPLC. The entrapment efficiency of the formulation was calculated with the following formula (wherein MNF=Mixed Nanomicellar Formulation):

$$\text{Entrapment efficiency} = \frac{\text{(amount of drug quantified in } MNF)}{\text{Amount of drug added in the } MNF} \times 100$$

Drug Quantification by an HPLC Method:

In vitro analysis of compound 1001 was performed by a reversed phase high performance liquid chromatography (RP-HPLC) method with a Shimadzu HPLC pump (Shimadzu, Shimadzu Scientific instruments, Columbia, Md.), Alcott autosampler (model 718 AL), Shimadzu UV/Visible detector (Shimadzu, SPD-20A/20AV, USA), ODS column (5 μm, 150×4.6 mm) thermostated at 40°±1 C and Hewlett Packard HPLC integrator (Hewlett Packard, Palo Alto, Calif.). The mobile phase was comprised of methanol (MeOH), water and trifluoroacetic acid (TFA) (70:30:0.05% v/v) which was set at a flow rate of 0.5 mL/min. Detection wavelength was set at 272 nm. The sample tray temperature was maintained at 4° C. Calibration curve (0.5 to 5 μg/mL) for compound 1001 was prepared by making appropriate dilutions from the stock solution in 2-propanol. An injection volume of 10 μl was injected into the HPLC column for analysis. All the standards and samples prepared were stored at 4° C. before and during the analysis.

Example 2

Preparation of Mixed Nanomicellar Resolvin Formulation Using Ethyl Acetate Solvent Evaporation Method Mixed nanomicellar formulation encapsulating compound 1001 was prepared by solvent evaporation method in two steps: 1) Preparation of basic formulation and 2) rehydration. In step one, compound 1001, HCO-60 and octoxynol-40 were dissolved separately in 0.3 mL of ethyl acetate. These three solutions were mixed together in 15-mL centrifuge tube. The resultant mixture was vortexed to obtain a homogenous solution. Ethyl acetate solvent was removed with speed vacuum to obtain a solid thin film. The residue was kept overnight under high vacuum at room temperature to remove residual organic solvent. In step two, the resultant thin film was hydrated with 1 mL of double distilled deionized water by vortexing the solution. The rehydrated formulation was suspended in 2× phosphate buffer solution, (pH 6.5). It was filtered through 0.2 μm nylon filter membrane to remove the unentrapped drug aggregates and other foreign particulates. The entrapment of compound 1001 was determined by RP-HPLC following disruption of the micelles and solubilization of 1001 in the diluent (2-propanol) as described below The prepared formulations were subjected to various tests such as entrapment efficiency, loading efficiency, mixed nanomicellar size and polydispersity index according to the methods described in Example 1.

Weight percent of drug loaded into MNF was determined following the method for entrapment efficiency. Size and polydispersity index of the formulations was determined with Malvern zetasizer as described above. The results obtained are summarized in Table 2 below. The formulations appear clear and have small size and narrow size distribution.

TABLE 2

Characterization of the mixed nanomicellar formulation encapsulating compound 1001 with solvent evaporation method

| HCO-60 (wt %) | Octoxynol-40 (wt %) | 1001 (initially added) wt % | 1001 (loaded in mixed micelles) wt % | Mixed nanomicellar size (nm) | Polydispersity Index | Result |
|---|---|---|---|---|---|---|
| 4 | 0.01 | 0.035 | 0.033 | 24.90 | 0.442 | Clear/transparent solution before and after filtration |
| 4 | 0.01 | 0.070 | 0.065 | 25.01 | 0.414 | Clear/transparent solution before and after filtration |
| 4 | 0.01 | 0.095 | 0.084 | 24.79 | 0.415 | Clear/transparent solution before and after filtration |
| 4 | 0.01 | 0.120 | 0.11 | 18.28 | 0.320 | Pale yellow color transparent solution before and after filtration |
| 4 | 0.01 | 0.250 | 0.26 | 18.37 | 0.331 | Yellow color solution before and after filtration |
| 4 | 0.01 | 0.300 | 0.32 | 18.29 | 0.345 | Yellow color solution before and after filtration |
| 4 | 0.01 | 0.400 | 0.45 | 18.2 | 0.333 | |

Example 3

Preparation of Mixed Nanomicellar Resolvin Formulation Using Melt Method

Two hundred milligrams of hydrogenated castor oil-60 (HCO-60) (4 wt %) was weighed and transferred to a 10 mL round bottom flask (RBF). The neck of the round bottom flask was closed with an aluminum foil, sealed with parafilm and transferred to water bath set at 40 C. The round bottom flask was left overnight in water bath to liquefy/melt the HCO-60. On the next day, ten micro liters of octoxynol-40 was diluted 100 folds and allowed to equilibrate at 40 C for 1 h in water bath. Similarly, compound 1001 (neat oil) was allowed to equilibrate at 40 C in the water bath for 1 h. To the HCO-60 melt, 50 μL of 100 fold diluted octoxynol-40 (0.01 wt %) was added at 40 C. To the above mixture, ~20 μL of compound 1001 at 40 C was added and was stirred. To this mixture distilled deionized water, approx. 2 mL, equilibrated at 40 C was slowly added and stirred. The neck of the round bottom flask was closed with aluminum foil and sealed with parafilm. The solution was stirred in water bath set at 40 C overnight protected from light (covering with aluminum foil). On the next day, the above obtained solution at 40 C was removed from water bath and allowed to cool to room temperature and observed for clarity. Two milliliters phosphate buffer (2×) was added to the above prepared solution (phosphate buffer was previously prepared and the pH was adjusted to 5.5). The volume of the formulation was made up to 5 mL with the 2× phosphate buffer saline. The prepared formulation was filtered with 0.2 μm nylon filter and stored at 4 C.

The prepared formulations were subjected to various tests such as entrapment efficiency, loading efficiency, mixed nanomicellar size and polydispersity index according to the methods described in Example 1.

Example 4

Preparation of Mixed Nanomicellar Resolvin Formulation Using Second Melt Method

The preparation of MNF encapsulating compound 1001 (neat oil) can be divided into two steps. As an example for the development of 3.0 wt % HCO-40 or HCO-60 MNF encapsulating 0.4% compound 1001 is described below. In step 1, HCO-40 or HCO-60, 150 mg, was thermostated at 40° C. in water bath to melt and result in a clear thick viscous liquid. To this melt polymer compound 1001 (~20 mg), thermostated at 40° C., was added and mixed for homogenous distribution. The mixture was allowed to reach room temperature, which resulted in a pale yellow color viscous liquid with HCO-40 and waxy solid with HCO-60. Further, to solidify the viscous liquid of HCO-40, the mixture was stored at 4° C. (in refrigerator).

In step 2, the pellet and/or viscous liquid was allowed to reach room temperatures under natural conditions. The pellet and/or viscous liquid was thermostated in water bath at 40° C. and resuspended in 2.0 mL of distilled water (thermostated at 40° C.) under constant stirring. This resulted in spontaneous development of a clear aqueous solution of 0.4% compound 1001 MNF. This aqueous solution was allowed to reach room temperature, under natural conditions. The pH of the solution was adjusted to 5.5 and the volume was made up with 2× phosphate buffer saline (pH 5.5) containing octoxynol-40 (0.01 wt %) and PVP-K-90 (1.2 wt %). The formulation was filtered through 0.2 μm nylon filter to remove any foreign material and obtain a clear homogenous aqueous RX-1001 formulation.

$^1$H NMR Qualitative Studies:

To determine the absence of free drug in the outer aqueous environment, qualitative studies were conducted. Qualitative proton nuclear magnetic resonance (NMR) studies were conducted with Varian 400 MHz NMR. Deuterated chloroform and water as solvent systems were used to resuspend the formulation and NMR studies were performed.

Results:

Compound added to HCO-40 or HCO-60 at 40° C. can be used to entrap the compound 1001. At higher temperatures the polymer and the drug mixture remains in viscous liquid state. When allowed to reach room temperature, under natural conditions, HCO-60 mixture solidifies and develops a waxy solid. This waxy solid when thermostated at 40° C., helps in resuspending the formulation in distilled water to spontaneously develop compound 1001 MNF. Similar observation and results were obtained with HCO-40 viscous liquid. The viscosity of the mixture appears to be improved at lower temperatures (4° C.). Therefore, it appears to stick to the walls of the container as thick viscous liquid. Upon allowing to reach back to room temperature the viscosity appears to be reduced and the mixture retains its flow back.

The waxy solid developed with HCO-60 and compound 1001 mixture may be helpful to protect the drug and prevent the drug degradation with a surface blanket of an inert gas. The other polymer (HCO-40) did not result in development of waxy solid at room temperature or at low refrigerated conditions (4° C.) when used up to approx. 3.0 wt %.

Qualitative proton NMR studies show that resuspending the formulation in the aqueous phase ($D_2O$) spontaneously generated mixed nanomicelles and no free drug peaks were evident in the aqueous solution. If the drug was not entrapped in the core of mixed nanomicelles then the oil would be floating at the surface as a separate oil phase. While on the otherhand, resuspending the same formulation in organic solvent such as deuterated chloroform ($CDCl_3$) showed distinct peaks corresponding to drug along with polymer peaks. This indicates that the drug was not encapsulated in the micelle core and freely available when present in organic solvent.

The results obtained for physical appearance of the mixture, different phases, at different temperatures and appearance of final formulation are summarized in Tables 3a-3c.

TABLE 3a

Physical appearance of melt mixture of HCO-60 and Compound 1001 at 25° C., resuspending in water at 40° C. and final formulation of mixed nanomicellar formulation encapsulating compound 1001 (HCO-60 was melted and compound 1001 was added to melt, then allowed to cool to room temperature and the physical appearance was noted)

| HCO-60 (wt %) | 1001 (wt %) | Physical appearance at room temperature (25° C.) | Resuspend in water | Final formulation (make up with 2X buffer containing 0.01% Oc-40) |
|---|---|---|---|---|
| 1.0 | 4 | Pale yellow half solid and half viscous liquid | Emulsion | Emulsion |
| 2.0 | 4 | Pale yellow viscous solid (with waxy and viscous liquid) | Forms pale emulsion | Pale yellow clear solution |
| 2.25 | 4 | Pale yellow waxy solid | Forms pale emulsion | Pale yellow clear solution |
| 2.5 | 4 | Pale yellow waxy solid | Forms very pale emulsion | Pale yellow clear solution |
| 2.75 | 4 | Pale yellow waxy solid | Forms very pale emulsion | Clear solution |
| 3.0 | 4 | Pale yellow waxy solid | Clear solution | Clear solution |
| 3.5 | 4 | Pale yellow waxy solid | Clear solution | Clear solution |
| 4.0 | 4 | Pale yellow waxy solid | Clear solution | Clear solution |

TABLE 3b

Physical appearance for HCO-40 and compound 1001 melt mixture at 25° C., resuspending in water and final formulation of mixed nanomicellar formulation encapsulating compound 1001 (HCO-40 was melted and compound 1001 was added to melt at 40° C. Then allowed to cool to room temperature and the physical appearance was noted)

| HCO-40 (wt %) | 1001 (wt %) | Mixture physical appearance at room temperature (25° C.) | Resuspend in water | Final formulation |
|---|---|---|---|---|
| 0.5 | 4 | Viscous yellow liquid | Emulsion | Emulsion |
| 0.75 | 4 | Viscous yellow liquid | Emulsion | Emulsion |
| 1.0 | 4 | Viscous yellow liquid | Emulsion | Emulsion |
| 1.25 | 4 | Viscous yellow liquid | Emulsion | Emulsion |
| 1.5 | 4 | Viscous yellow liquid | Emulsion | Emulsion |
| 1.75 | 4 | Viscous yellow liquid | Emulsion | Emulsion |
| 2.0 | 4 | Viscous yellow liquid | Emulsion | Emulsion |
| 2.25 | 4 | Viscous yellow liquid | Emulsion | Emulsion |
| 2.5 | 4 | Viscous yellow liquid | Yellow solution | Yellow color solution |
| 2.75 | 4 | Viscous yellow liquid | Pale yellow solution | Pale yellow color solution |
| 3.0 | 4 | Viscous yellow liquid | Clear solution | Clear solution |
| 4.0 | 4 | Viscous yellow liquid | Clear solution | Clear solution |

TABLE 3c

Physical appearance of HCO-40 and compound 1001 melt mixture at 25° C. and 4° C., mixture resuspended in water at 40° C. and final formulation. (HCO-40 was melted and compound 1001 was added to melt at 40° C. Then allowed to cool to room temperature, placed at 4° C. and brought back to room temperature. Physical appearance of mixture was noted at all temperatures)

| HCO-40 (wt %) | 1001 (wt %) | Mixture physical appearance at room temperature (25° C.) | Mixture physical appearance at room temperature (4° C.) | Allow to reach room temperature (25° C.) | Resuspend in water | Final formulation |
|---|---|---|---|---|---|---|
| 0.5 | 4 | Viscous yellow liquid | Viscous liquid | Viscous liquid | Emulsion | Emulsion |
| 0.75 | 4 | Viscous yellow liquid | Viscous liquid | Viscous liquid | Emulsion | Emulsion |

TABLE 3c-continued

Physical appearance of HCO-40 and compound 1001 melt mixture at 25° C. and 4° C., mixture resuspended in water at 40° C. and final formulation. (HCO-40 was melted and compound 1001 was added to melt at 40° C. Then allowed to cool to room temperature, placed at 4° C. and brought back to room temperature. Physical appearance of mixture was noted at all temperatures)

| HCO-40 (wt %) | 1001 (wt %) | Mixture physical appearance at room temperature (25° C.) | Mixture physical appearance at room temperature (4° C.) | Allow to reach room temperature (25° C.) | Resuspend in water | Final formulation |
|---|---|---|---|---|---|---|
| 1.0 | 4 | Viscous yellow liquid | Viscous liquid | Viscous liquid | Emulsion | Emulsion |
| 1.25 | 4 | Viscous yellow liquid | Viscous liquid | Viscous liquid | Emulsion | Emulsion |
| 1.5 | 4 | Viscous yellow liquid | Yellow waxy solid | Viscous liquid | Emulsion | Emulsion |
| 1.75 | 4 | Viscous yellow liquid | Yellow waxy solid | Viscous liquid | Emulsion | Emulsion |
| 2.0 | 4 | Viscous yellow liquid | Yellow waxy solid | Viscous liquid | Emulsion | Emulsion |
| 2.25 | 4 | Viscous yellow liquid | Yellow waxy solid | Viscous liquid | Emulsion | Emulsion |
| 2.5 | 4 | Viscous yellow liquid | Yellow waxy solid | Viscous liquid | Yellow solution | Yellow color solution |
| 2.75 | 4 | Viscous yellow liquid | Pale yellow waxy solid | Viscous liquid | Pale yellow solution | Very pale yellow color solution |
| 3.0 | 4 | Viscous yellow liquid | Pale yellow solid | Viscous liquid (half solid half viscous liquid) | Clear solution | Clear solution |
| 4.0 | 4 | Viscous yellow liquid | Pale yellow waxy solid | Pale yellow waxy solid | Clear solution | Clear solution |

Conclusions. These studies show that the polymer HCO-60 can be used to entrap compound 1001 with Hot Melt method. HCO-40 did not develop waxy solid at higher weight percent (3.0%) under the conditions of this study. On the otherhand, HCO-60 developed waxy solid at 2.0 wt %. This method has unique advantages of being an easy and fast method that avoids the use of organic solvent in the preparation of MNF. Also, the method of preparation is easy and fast. The waxy solid developed in stage 1 may be helpful in preventing the drug degradation and help the drug to stay in waxy solid state at room temperatures with a blanket of inert gas. Qualitative proton NMR studies show that drug is not freely available when resuspended in aqueous solution. On the otherhand, when the same formulation was resuspended in organic solvent, $CDCl_3$, drug peaks were clearly evident indicating the presence of drug in the outer organic solvent environment due to the formation.

Example 5

Preparation of Mixed Nanomicellar Cyclosporine Formulation

MNF formulation of cyclosporineA (Cys-A) was prepared by solvent evaporation method in two steps: 1. Preparation of basic formulation and 2. rehydration. In step one, cyclosporine, HCO-40 and octoxynol-40 were dissolved separately in 0.5 mL of ethanol aliquots. These three solutions were mixed together in a round bottom flask. The resultant mixture was stirred to obtain a homogenous solution. Ethanol solvent was removed by high speed vacuum evaporation overnight to obtain a solid thin film. In step two, the resultant thin film was hydrated with 2.0 mL of double distilled deionized water and resuspended with stirring overnight. The rehydrated formulation was pH adjusted and volume was made up with 2× phosphate buffer solution, (pH 6.8). Further the formulation was filtered through 0.2 μm nylon filter membrane to remove the unentrapped drug aggregates and other foreign particulates.

Different polymer weight percent combination than were used for the above resolvin examples were used to develop aqueous MNF entrapping 0.2 wt % cyclosporine-A. Formulations were characterized for their appearance, size and polydispersity indices. The formulations were found to be clear (FIG. 5) and have very small size with narrow polydispersity index. The results are summarized in tables 4a and 4b.

TABLE 4a

Cyclosporine mixed nanomicellar formulations at lower polymer concentrations.

| HCO-40 wt % | Octoxynol-40 wt % | Visual appearance | Size (nm) | Polydispersity index |
|---|---|---|---|---|
| 0.5 | 0.1 | Emulsion | N.D | N.D |
| 0.75 | 0.1 | Emulsion | N.D | N.D |
| 1 | 0.1 | Emulsion | N.D | N.D |
| 1.25 | 0.1 | Emulsion | N.D | N.D |
| 1.5 | 0.1 | Emulsion | N.D | N.D |
| 1.75 | 0.1 | Clear solution | 14.86 | 0.062 |
| 2.00 | 0.1 | Clear solution | 36.14 | 0.884 |
| 0.5 | 0.5 | Emulsion | N.D | N.D |
| 0.75 | 0.5 | Emulsion | N.D | N.D |
| 1 | 0.5 | Emulsion | N.D | N.D |
| 1.25 | 0.5 | Emulsion | N.D | N.D |
| 1.5 | 0.5 | Emulsion | N.D | N.D |
| 1.75 | 0.5 | Clear solution | 14.81 | 0.075 |
| 2.00 | 0.5 | Clear solution | 21.27 | 0.295 |

N.D—Not Determined.

TABLE 4b

Cyclosporine mixed nanomicellar formulations at higher polymer concentrations.

| HCO-40 wt % | Octoxynol-40 wt % | Visual appearance | Size (nm) | Polydispersity index |
|---|---|---|---|---|
| 0.5 | 1.0025 | Clear solution | 12.9 | 0.069 |
| 0.5 | 2 | Clear solution | 18.1 | 0.069 |
| 2.5 | 0.005 | Clear solution | 15.65 | 0.064 |
| 2.5 | 1.0025 | Clear solution | 14.56 | 0.096 |
| 2.5 | 1.0025 | Clear solution | 14.81 | 0.078 |
| 2.5 | 1.0025 | Clear solution | 14.80 | 0.098 |
| 2.5 | 1.0025 | Clear solution | 14.45 | 0.102 |
| 2.5 | 2 | Clear solution | 13.92 | 0.108 |
| 4.5 | 0.005 | Clear solution | 20.59 | 0.271 |
| 4.5 | 1.0025 | Clear solution | 15.08 | 0.087 |
| 4.5 | 2 | Clear solution | 15.37 | 0.079 |

Water Method.

MNF formulation of cyclosporinA (CsA) was prepared by the water method. One mL of double distilled deionized water was heated to 60° C. in a round bottom flask. This heated water was kept under stirring. HCO-40 was added to the heated water and allowed to dissolve under constant stirring. Octoxynol-40 was then added to this mixture and allowed to dissolve. In a separate container, phosphates, sodium chloride and CsA were blended by hand shaking for a few minutes. Under stirring conditions, the phosphates/CsA/sodium chloride blend was added to the solution of HCO-40 and octoxynol-40 to disperse the drug. This mixture was allowed to cool to room temperature while stirring and check for complete dissolution of drug. PVP K 90 solution was separately prepared using the remaining 1 mL double distilled deionized water. This PVP K 90 solution was added to the solution of polymer/surfactant/drug/phosphate/sodium chloride. Water was added to make up the final volume. Then the formulation was filtered through 0.2 μm nylon membrane to remove the drug aggregates and other foreign particulates.

Example 6

Local Tolerability in Rabbits of Formulations

Healthy young adult New Zealand albino rabbits (3-4 Kg) used for the study the local tolerability of the instant formulations, for example a formulation of Examples 1-5. One drop (approximately 30 .mu·L) of saline is placed in one eye and a drop of formulation is placed in the other eye of the rabbit. Both eyes of each animal are examined by a veterinary ophthalmologist using a hand-held slit lamp and indirect ophthalmoscope. Both control and test eyes are graded according to conjunctival congestion, swelling, and discharge, aqueous flare, iris light reflex and involvement, corneal cloudiness severity and area, pannus, fluorescein examination and lens opacity using the Hackett/McDonald scoring system (see, for example, Hackett, R. B. and McDonald, T. O. Ophthalmic Toxicology and Assessing Ocular Irritation. Dermatoxicology, 5.sup.th Edition. Ed. F. N. Marzulli and H. I. Maibach. Washington, D.C.: Hemisphere Publishing Corporation. 1996; 299-305 and 557-566.). In the fluorescein examination, approximately one drop of 0.9% sodium chloride, USP, is applied to the end of a fluorescein impregnated strip and then applied to the superior sclera of the left and right eyes (one fluorescein impregnated strip is used for each animal). After an approximate 15 second exposure, the fluorescein dye is gently rinsed from each eye with 0.9% sodium chloride, USP. The eyes are then examined using a slit lamp with a cobalt blue filtered light source. For the lenticular examination approximately one drop of a short-acting mydriatic solution is instilled onto each eye in order to dilate the pupil. After acceptable dilation has occurred, the lens of each eye is examined using a slit-lamp biomicroscope.

The crystalline lens is observed with the aid of the slit-lamp biomicroscope, and the location of lenticular opacity is discerned by direct and retro illumination. The location of lenticular opacities are arbitrarily divided into the following lenticular regions beginning with the anterior capsule: Anterior subcapsular, Anterior cortical Nuclear Posterior cortical, Posterior subcapsular, Posterior capsular. The lens is evaluated routinely during ocular evaluations and graded as either 0 (normal) or 1 (abnormal). The presence of lenticular opacities are described and the location noted.

Example 7

Ocular Tissue Distribution of Formulations of 0.05 wt %, 0.2 wt % and 0.5 wt % in Mixed Micellar Formulations of the Present Disclosure The temporal distribution and potential accumulation with repeat dosing, gender difference, and potential melanin binding of (ophthalmic solution) of the present disclosure (for example the formulations of Examples 1-5) after ocular application is assessed by determining concentration of active ingredients in ocular tissues, tears, and blood in New Zealand White (NZW) and Dutch Belted (DB) rabbits.

NZW rabbits are used in a single dose (SD) and 7-day repeat dose (RD) studies. DB rabbits will be used in a single dose study). Animals are either untreated (controls) or given a single or a daily topical ocular dose for 7 days (0.05 wt %, 0.2 wt % or 0.5 wt % in a mixed micellar formulation to one or both eyes). Blood and ocular tissue concentrations are assessed.

The concentration of drug is in tissues in the front of the eye (cornea, conjunctiva, sclera) and at the back of the eye (retina, optic nerve) but minimal in the middle of the eye (aqueous and vitreous humor), suggesting transport of the drug by a mechanism other than passive transport through the eye. The high drug levels achieved at the back of the eye make topical administration of the compositions of the present disclosure feasible for the treatment of diseases of the back-of-the-eye (e.g., retinal, diseases involving optic nerve such as glaucoma). Very high levels, especially in target tissues such as lachrymal gland, will be shown with the compositions of the present disclosure.

Example 8

Use of Resolvin Mixed Nanomicellar Formulations for Treating Dry Eye

Mixed nanomicellar formulations according to Examples 1-5 are administered to an patient having dry eye at a concentration of between 0.05% and 0.2% b.i.d. over a period of 1 month to 1 year or more.

Example 9

Use of Resolvin Mixed Nanomicellar Formulations for Treating Diabetic Retinopathy Mixed nanomicellar formulations according to Examples 1-5 are administered to an patient having proliferative diabetic retinopathy at a concentration of between 0.2 wt % to 0.5 wt % b.i.d. over a period of 1 month to 1 year or more.

Example 10

Tolerance and Ocular Tissue Distribution of Cyclosporine Mixed Nanomicellar Formulations A study was conducted in rabbits to test the tolerance and ocular tissue distribution of a nanomicellar formulation of cyclosporine against its placebo and balanced saline solution (BSS). Healthy New Zealand female white rabbits (2-3 kg) were used for this study. Cyclosporine study drug was prepared having 0.1% cyclosporine essentially as described in the examples herein. The below table shows the formulation composition of the CsA formulation and the Placebo.

TABLE 5

Formulation Composition:

| Components | CsA 0.1% formulation | Placebo |
|---|---|---|
| Cyclosporine | 0.1% | 0 |
| Hydrogenated castor oil-40 | 1.0% | 1.0% |
| Octoxynol-40 | 0.05% | 0.05% |
| Sodium chloride | 0.10% | 0.10% |
| PVP-K90 | 0.60% | 0.60% |
| Disodium EDTA | 0.05% | 0.05% |
| Benzalkonium chloride | 0.003% | 0.003% |
| Sodium Phosphate buffer | ~0.4% | ~0.4% |
| pH | 7 | 7 |

One drop (approximately 35 μL) of study drug was applied o.d. 4×/day at two hour intervals for 5 days. One drop of BSS was applied to the contralateral eye.

The tolerance parameters evaluated were: physical examination (acclimation study release); viability (daily); clinical observations (daily); Hackett-McDonald Ocular Irritation scores (pre-dose baseline data for each rabbit and then a pre-dose [prior to first daily dose] each day and then 30 min after last dose daily, intraocular pressure (IOP) pre-dose baseline data for each rabbit and then 30 minutes after the evening examinations each day, electroretinography (ERG) pre-dose-(pre-study) baseline data for each rabbit and then one hour after the last treatment, and ocular histopathology at euthanasia.

Mean cumulative Hackett-McDonald ocular irritation scores demonstrated very minimal scores for both BSS-treated left eyes and cyclosporine treated right eyes throughout the study, both for pre-treatment and post-treatment examination times. Mean cumulative inflammatory scores of less than 2 were observed in eyes treated with the TA, placebo, and BSS. These clinical scores represented mild conjunctival hyperemia (redness) and swelling. However, there were no significant differences in mean cumulative Hackett-McDonald ocular irritation scores between the groups, suggesting no difference in irritation from topical application of 0.1% CsA in HCO-40, the HCO-40 placebo, and BSS.

No changes in IOP were noted in eyes treated with BSS, HCO-40, or CsA. No toxicologic changes in retinal function were noted on ERG after 5 days of treatment with the test articles. No toxicologic or inflammatory changes were observed histologically in the anterior (conjunctiva/cornea/iris) or posterior segments (vitreous/retina) of the eye of any groups.

Samples of selected ocular tissues (aqueous humor, vitreous humor, conjunctiva, cornea, iris-ciliary body, lens, retina/choroid, and sclera) were collected 1 hour following the last dose on Day 5 from all two rabbits that received 0.1% CsA with HCO-40 (OD), and BSS (OS), and from one rabbit (No. 21) that received placebo HCO-40 formulation (OD) and BSS (OS). The samples were assayed for cyclosporine (CsA) by liquid chromatography-tandem mass spectrometry (LC-MS/MS). The internal standard was $d_4$-cyclosporine. The established analytical ranges for CsA were 0.100-100 ng/mL for whole blood, and 2.00-2000 ng/mL for aqueous humor and vitreous humor. The analytical ranges for the solid tissues were 0.125-30 ng (low range) and 1.00-2500 ng (high range). The results of the solid tissue analyses were converted to ng/g by correcting for the amount of tissue analyzed.

Concentrations of CsA in ocular tissues collected 1 hour following the last dose on Day-5 are summarized in Table 6. Following repeated administration of the 0.1% CsA HCO-40 formulation, the highest average CsA concentrations in the treated eye were observed in cornea (7805 ng/g), followed by conjunctiva (2125 ng/g), sclera (720 ng/g), iris-ciliary body (204 ng/g), and aqueous humor (134 ng/mL). The lowest CsA concentrations were observed in the lens (68.6 ng/g), retina/choroid (54 ng/g), and vitreous humor (~8 ng/mL). CsA concentrations in the collateral eye treated with BSS were quite low suggesting minimal systemic transfer of drug.

The ocular tissue concentrations for the 0.1% CsA formulation observed in this study were generally higher than the $C_{max}$ values following repeat dose administration (bid for 7 days) of an Allergan 0.2% 3H cyclosporine A formulation to rabbits (see Acheampong A A, Shackleton M, Tang-Liu D, Ding S, Stern M E, Decker R Distribution of cyclosporin A in ocular tissues after topical administration to albino rabbits and beagle dogs; Current Eye Research 18(2); 1999; pp 91-103).

TABLE 6

| Matrix | Nanomicellar 0.1% CsA | Allergan 0.2% CsA |
|---|---|---|
| Aqueous Humor | 134. 5 ng/mL | 19.3 ng-eq/mL |
| Vitreous Humor | 8.37 ng/mL | 0.810 ng-eq/mL |
| Sclera | 720.5 ng/g | 35.2 ng-eq/g |
| Conjunctiva | 2125 ng/g | ND ng-eq/g |
| Cornea | 7805 ng/g | 6011 ng-eq/g |
| Iris-Ciliary Body | 204 ng/g | 109 ng-eq/g |
| Lens | 68.6 ng/g | 39.6 ng-eq/g |
| Retina/Choroid | 53.7 ng/g | 4.62 ng-eq/g |

Example 11

Tolerance and Ocular Tissue Distribution of Compound 1001 Mixed Nanomicellar Formulations A study was conducted in rabbits to test the tolerance and ocular tissue distribution of two nanomicellar formulations of compound 1001 (RX10045) against matching placebos (Table 7a and 7b) and balanced saline solution (BSS). Healthy New Zealand female white rabbits (2-3 kg) were used for this study. One drop (approximately 35 μL) of study drug was applied o.d. 4×/day at two hour intervals for 5 days. One drop of BSS was applied to the contralateral eye.

The tolerance parameters evaluated were: physical examination (acclimation study release); viability (daily); clinical observations (daily); Hackett-McDonald Ocular Irritation scores (pre-dose baseline data for each rabbit and then a pre-dose [prior to first daily dose] each day and then 30 min after last dose daily, intraocular pressure (IOP) pre-dose baseline data for each rabbit and then 30 minutes after the evening examinations each day, electroretinography (ERG) pre-dose-(pre-study) baseline data for each rabbit and then one hour after the last treatment, and ocular histopathology at euthanasia.

TABLE 7a

Formulation Composition: RX-10045 0.15%

| Components | RX-10045 (0.1%) in HCO-40 percentage | Placebo percentage |
|---|---|---|
| RX-10045 | 0.1% | 0 |
| Hydrogenated Castor Oil-40 | 1.0% | 1.0% |
| Octoxynol-40 | 0.05% | 0.05% |
| Sodium chloride | 0.10% | 0.10% |
| PVP-K90 | 0.60% | 0.60% |
| Disodium EDTA | 0.05% | 0.05% |
| Benzalkonium chloride | 0.003% | 0.003% |
| Sodium Phosphate buffer | ~0.4% | ~0.4% |
| pH | 5.5 | 5.5 |

TABLE 7b

Formulation Composition: RX-10045 0.1%

| Components | RX-10045 (0.15%) in HCO-60 percentage | Placebo Percentage |
|---|---|---|
| RX-10045 | 0.15% | 0 |
| Hydrogenated Castor Oil-60 | 1.0% | 1.0% |
| Octoxynol-40 | 0.05% | 0.05% |
| Sodium chloride | 0.10% | 0.10% |
| PVP-K90 | 0.60% | 0.60% |
| Disodium EDTA | 0.05% | 0.05% |
| Beuzalkonium chloride | 0.003% | 0.003% |
| Sodium Phosphate buffer | ~0.4% | ~0.4% |
| pH | 5.5 | 5.5 |

Cumulative Hackett-McDonald ocular irritation scores demonstrated very minimal mean values for both BSS-treated left eyes and test-article treated right eyes throughout the study, both for pre-treatment and post-treatment examination times. There were no significant differences in mean cumulative Hackett-McDonald ocular irritation scores between the groups (Table 8). The observed ocular irritation was interpreted as minimal and transient in all groups.

TABLE 8

Hackett-McDonald Composite Scores (mean ± s.d.)

| | HCO-40 Placebo[a] | RX-10045 0.1%[b] | HCO-60 placebo[a] | RX-10045 0.15%[b] |
|---|---|---|---|---|
| Day 1 Predose | 0.0-0.0 | 0.0-0.0 | 0.0-0.0 | 0.0-0.0 |
| Day 1 Postdose | 1.7-1.5 | 0.5-0.1 | 0.0-0.0 | 0.5-0.1 |
| Day 2 Predose | 0.0-0.0 | 0.0-0.0 | 0.0-0.0 | 1.0-1.2 |
| Day 2 Postdose | 2.0-0.0 | 0.0-0.0 | 0.7-1.1 | 0.5-1.0 |
| Day 3 Predose | 0.0-0.0 | 0.0-0.0 | 0.0-0.0 | 0.5-1.0 |
| Day 3 Postdose | 1.3-1.2 | 0.0-0.0 | 0.0-0.0 | 1.0-1.2 |
| Day 4 Predose | 1.3-1.2 | 0.0-0.0 | 0.3-0.6 | 0.5-1.0 |

TABLE 8-continued

Hackett-McDonald Composite Scores (mean ± s.d.)

| | HCO-40 Placebo[a] | RX-10045 0.1%[b] | HCO-60 placebo[a] | RX-10045 0.15%[b] |
|---|---|---|---|---|
| Day 4 Postdose | 1.3-1.2 | 0.0-0.0 | 0.7-1.2 | 0.8-1.0 |
| Day 5 Predose | 0.0-0.0 | 0.5-1.0 | 1.0-1.0 | 0.0-0.0 |
| Day 5 Postdose | 1.3-2.3 | 0.0-0.0 | 0.3-0.6 | 0.8-1.1 |

No changes in TOP were noted in eyes treated with BSS or test articles. No toxicologic changes in retinal function were noted on ERG after 5 days of treatment with the test articles. No toxicologic or inflammatory changes were observed histologically in the anterior (conjunctiva/cornea/iris) or posterior segments (vitreous/retina) of the eye of any groups.

Selected ocular fluids/tissues (aqueous humor, vitreous humor, conjunctiva, cornea, iris-ciliary body, lens, retina/choroid, and sclera) collected from two rabbits each in the RX-10045 (0.15% in HCO-60, 0.1% in HCO-40) treatment groups, and from one rabbit in each of the matching placebo groups, were assayed for compound 1001 and another resolvin by liquid chromatography-tandem mass spectrometry (LC-MS/MS). Warfarin-$d_5$ and 5-HDA were used as internal standards for the analysis of RX-10045 and its active metabolite, RX-10008, respectively, in aqueous humor and vitreous humor. For the other ocular tissues (solid tissues), warfarin-d5 and phenyl acetic acid-d5 (PAA-$d_5$) were used as the internal standards for compound 1001 and RX-10008, respectively. The analytical range for the solid tissues were 0.125-100 ng. The results of the solid tissue analyses were converted to ng/g by correcting for the amount of tissue analyzed.

Only sporadic, relatively low, concentrations of the compound 1001 ester prodrug were observed in the sclera and conjunctiva. Compound 1001 was either not detected or was below the quantitation limit of the assay in the majority of ocular tissues. These data suggest that RX-10045 was rapidly hydrolyzed to its active metabolite, RX-10008.

A summary of the parent compound (RX-10008) tissue concentrations are presented in Table 9. The highest concentrations of RX-10008 were found in the cornea, followed by the iris-ciliary body, conjunctiva, and sclera. There were also relatively high concentrations of RX-10008 in the aqueous humor. Lower amounts were found in the retina/choroid and lens. The lowest levels of RX-10008 were found in the vitreous humor.

TABLE 9

Comparison of mean (n = 2) RX-10008 ocular tissue concentrations following topical ocular administration of RX-10045 (0.15% in HCO-60, 0.1% in HCO-40) formulations to the eye four times a day at 2 hour intervals for five days to New Zealand White Rabbits

| | Treatment Group 4 0.15% RX-10045 in HCO-60 | Treatment Group 5 0.1% RX-10045 in HCO-40 |
|---|---|---|
| | RX-1008 (ng/g or ng/mL) | |
| Sclera | 9.90[a] | 701 |
| Cornea | 15700[a] | 9650[a] |
| Conjunctiva | 1132 | 879 |
| Lens | 136 | 164 |
| Iris-Ciliary Body | 2725 | 2655 |
| Retina/Choroid | 410 | 323 |

TABLE 9-continued

Comparison of mean (n = 2) RX-10008 ocular tissue concentrations following topical ocular administration of RX-10045 (0.15% in HCO-60, 0.1% in HCO-40) formulations to the eye four times a day at 2 hour intervals for five days to New Zealand White Rabbits

| | Treatment Group 4 0.15% RX-10045 in HCO-60 | Treatment Group 5 0.1% RX-10045 in HCO-40 |
|---|---|---|
| | RX-1008 (ng/g or ng/mL) | |
| Vitreous Humor | 18 | 15.7 |
| Aqueous Humor | >2000 | >2000 |

$^a$n = 1

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. An aqueous clear nanomicellar ophthalmic formulation, comprising:
   an active agent,
   0.5-4.5% by weight of a polymer comprising HCO-40, HCO-60, HCO-80, HCO-100, polyoxyl 35 castor oil or combinations thereof; and
   0.02-0.08% of a polyalkoxylated alcohol.

2. The aqueous clear nanomicellar ophthalmic formulation of claim 1, wherein said polymer comprises HCO-40, HCO-60, HCO-80, HCO-100 or combinations thereof.

3. The aqueous clear nanomicellar ophthalmic formulation of claim 1, wherein said polyalkoxylated alcohol is Octoxynol-40.

4. The aqueous clear nanomicellar ophthalmic formulation of claim 2, wherein said polymer is HCO-40.

5. The aqueous clear nanomicellar ophthalmic formulation of claim 2, wherein said polymer is HCO-60.

6. The aqueous clear nanomicellar ophthalmic formulation of claim 1, wherein said polymer is 1-4% by weight.

7. The aqueous clear nanomicellar ophthalmic formulation of claim 3, wherein Octoxynol-40 is 0.05% by weight.

\* \* \* \* \*